(12) United States Patent
Rubin

(10) Patent No.: US 12,734,317 B2
(45) Date of Patent: Sep. 15, 2026

(54) SYSTEMS AND METHODS OF AEROSOL DELIVERY WITH AIRFLOW REGULATION

(71) Applicant: Altria Client Services LLC, Richmond, VA (US)

(72) Inventor: Darren Rubin, Largo, FL (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 1159 days.

(21) Appl. No.: 17/568,578

(22) Filed: Jan. 4, 2022

(65) Prior Publication Data

US 2022/0126036 A1 Apr. 28, 2022

Related U.S. Application Data

(63) Continuation of application No. 16/458,702, filed on Jul. 1, 2019, now Pat. No. 11,247,003, which is a (Continued)

(51) Int. Cl.
*A61M 15/00* (2006.01)
*A24F 40/10* (2020.01)

(Continued)

(52) U.S. Cl.
CPC ....... *A61M 15/0085* (2013.01); *A24F 40/485* (2020.01); *A24F 40/50* (2020.01);

(Continued)

(58) Field of Classification Search
CPC .......... A61M 15/0085; A61M 15/0008; A61M 15/002; A61M 15/0028; A61M 15/0066;

(Continued)

(56) References Cited

U.S. PATENT DOCUMENTS 374,584 A 12/1887 Cook
576,653 A 2/1897 Bowlby (Continued)

FOREIGN PATENT DOCUMENTS

AT 503485 B1 3/2009
CN 1039530 A 2/1990

(Continued)

OTHER PUBLICATIONS

Extended European Search Report received for European Patent Application No. 21171539.6, mailed on Nov. 18, 2021, 9 pages.

(Continued)

*Primary Examiner* — Tu A Vo
*Assistant Examiner* — Kelsey E Baller
(74) *Attorney, Agent, or Firm* — Harness, Dickey & Pierce, P.L.C.

(57) ABSTRACT

An example aerosol delivery device includes a mouthpiece having an airflow outlet, and an airflow passage extending between an airflow inlet and the airflow outlet. The example aerosol delivery device further includes a housing configured to receive a cartridge that includes an aerosolizable substance and a vapor element configured to heat the aerosolizable substance, and an internal power source configured to provide electrical power. The example aerosol delivery device further includes a controller coupled to the internal power source to receive a portion of the electrical power and configured to, when the cartridge is installed at the housing, cause the vapor element of the cartridge to heat the aerosolizable substance to release an aerosol into the airflow passage during an inhalation through the airflow outlet, and a connector configured to receive power from an external source to recharge the internal power source.

29 Claims, 28 Drawing Sheets

Related U.S. Application Data continuation of application No. 15/672,021, filed on Aug. 8, 2017, now abandoned, which is a continuation-in-part of application No. 13/969,847, filed on Aug. 19, 2013, now Pat. No. 9,757,528, which is a continuation-in-part of application No. 12/806,874, filed on Aug. 23, 2010, now abandoned.

(51) Int. Cl.

| | |
|---|---|
| ***A24F 40/485*** | (2020.01) |
| ***A24F 40/50*** | (2020.01) |
| ***A24F 40/60*** | (2020.01) |
| ***A24F 40/90*** | (2020.01) |
| ***A61M 11/00*** | (2006.01) |
| ***A61M 11/04*** | (2006.01) |
| ***A61M 11/06*** | (2006.01) |
| ***A61M 15/06*** | (2006.01) |
| ***A61M 16/00*** | (2006.01) |
| ***A61M 16/08*** | (2006.01) |
| ***A61M 16/10*** | (2006.01) |
| ***A61M 16/14*** | (2006.01) |
| ***A61M 16/20*** | (2006.01) |
| *A61M 15/02* | (2006.01) |

(52) U.S. Cl.

CPC ......... *A61M 11/005* (2013.01); *A61M 11/041* (2013.01); *A61M 11/042* (2014.02); *A61M 11/047* (2014.02); *A61M 11/06* (2013.01); *A61M 15/0008* (2014.02); *A61M 15/002* (2014.02); *A61M 15/0028* (2013.01); *A61M 15/0066* (2014.02); *A61M 15/008* (2014.02); *A61M 15/0091* (2013.01); *A61M 15/0093* (2014.02); *A61M 15/0095* (2014.02); *A61M 15/06* (2013.01); *A61M 16/0093* (2014.02); *A61M 16/0866* (2014.02); *A61M 16/105* (2013.01); *A61M 16/1055* (2013.01); *A61M 16/1065* (2014.02); *A61M 16/14* (2013.01); *A61M 16/204* (2014.02); *A61M 16/209* (2014.02); *A24F 40/10* (2020.01); *A24F 40/60* (2020.01); *A24F 40/90* (2020.01); *A61M 11/007* (2014.02); *A61M 15/02* (2013.01); *A61M 15/025* (2014.02); *A61M 2016/0027* (2013.01); *A61M 2016/0033* (2013.01); *A61M 2016/0039* (2013.01); *A61M 16/101* (2014.02); *A61M 2202/064* (2013.01); *A61M 2202/30* (2013.01); *A61M 2205/13* (2013.01); *A61M 2205/3653* (2013.01); *A61M 2205/505* (2013.01); *A61M 2205/52* (2013.01); *A61M 2205/6018* (2013.01); *A61M 2205/6054* (2013.01); *A61M 2205/6072* (2013.01); *A61M 2205/8206* (2013.01); *A61M 2205/8237* (2013.01); *A61M 2205/8262* (2013.01); *A61M 2205/8268* (2013.01); *A61M 2210/0618* (2013.01); *A61M 2210/065* (2013.01); *A61M 2210/1028* (2013.01); *A61M 2210/1032* (2013.01); *A61M 2210/1035* (2013.01); *A61M 2210/1039* (2013.01)

(58) Field of Classification Search

CPC ............ A61M 15/008; A61M 15/0091; A61M 15/0093; A61M 15/0095; A61M 15/06; A61M 15/02; A61M 15/025; A61M 15/0015; A61M 15/0016; A61M 15/0018; A61M 15/0045; A61M 15/0086; A61M 11/005; A61M 11/041; A61M 11/042; A61M 11/047; A61M 11/06; A61M 11/007; A61M 11/002; A61M 16/0093; A61M 16/0866; A61M 16/105; A61M 16/1055; A61M 16/1065; A61M 16/14; A61M 16/204; A61M 16/209; A61M 16/101; A61M 16/0063; A61M 16/0066; A61M 16/208; A61M 2016/0027; A61M 2016/0033; A61M 2016/0039; A61M 2016/0024; A61M 2202/064; A61M 2202/30; A61M 2202/0208; A61M 2202/0225; A61M 2202/0241; A61M 2202/025; A61M 2202/0266; A61M 2202/0275; A61M 2202/0283; A61M 2205/13; A61M 2205/3653; A61M 2205/505; A61M 2205/52; A61M 2205/6018; A61M 2205/6054; A61M 2205/6072; A61M 2205/8206; A61M 2205/8237; A61M 2205/8262; A61M 2205/8268; A61M 2205/07; A61M 2205/18; A61M 2205/43; A61M 2205/581; A61M 2205/70; A61M 2205/7509; A61M 2205/7518; A61M 2210/0618; A61M 2210/065; A61M 2210/1028; A61M 2210/1032; A61M 2210/1035; A61M 2210/1039; A61M 2209/088; A24F 40/485; A24F 40/50; A24F 40/10; A24F 40/60; A24F 40/90

See application file for complete search history.

(56) References Cited

U.S. PATENT DOCUMENTS

| | | | |
|---|---|---|---|
| 595,070 | A | 12/1897 | Oldenbusch |
| 720,007 | A | 2/1903 | Dexter |
| 799,844 | A | 9/1905 | Dennis |
| 968,160 | A | 8/1910 | Johnson |
| 969,076 | A | 8/1910 | Pender |
| 1,067,531 | A | 7/1913 | Macgregor |
| 1,163,183 | A | 12/1915 | Stoll |
| 1,299,162 | A | 4/1919 | Fisher |
| 1,505,748 | A | 8/1924 | Tamis |
| 1,552,877 | A | 9/1925 | Phillipps et al. |
| 1,632,335 | A | 6/1927 | Hiering |
| 1,706,244 | A | 3/1929 | Meyerson |
| 1,845,340 | A | 2/1932 | Ritz Woller |
| 1,972,118 | A | 9/1934 | Mcdill |
| 1,998,683 | A | 4/1935 | Montgomery |
| 2,031,363 | A | 2/1936 | Erikson |
| 2,039,559 | A | 5/1936 | Segal |
| 2,104,266 | A | 1/1938 | McCormick |
| 2,159,698 | A | 5/1939 | Julius et al. |
| 2,177,636 | A | 10/1939 | Norman et al. |
| 2,195,260 | A | 3/1940 | Rasener |
| 2,231,909 | A | 2/1941 | Hempel |
| 2,327,120 | A | 8/1943 | Mccoon |
| 2,460,427 | A | 2/1949 | Musselman et al. |
| 2,483,304 | A | 9/1949 | Vogel |
| 2,502,561 | A | 4/1950 | Ebert |
| 2,765,949 | A | 10/1956 | Hillman |
| 2,774,346 | A | 12/1956 | Palmer |
| 2,830,597 | A | 4/1958 | Kummli |
| 2,860,638 | A | 11/1958 | Bartolomeo |
| 2,897,958 | A | 8/1959 | Tarleton et al. |
| 2,935,987 | A | 5/1960 | Ackerbauer |
| 3,146,937 | A | 9/1964 | Vesak |
| 3,258,015 | A | 6/1966 | Ellis et al. |
| 3,271,719 | A | 9/1966 | Ovshinsky |
| 3,292,634 | A | 12/1966 | Beucler |
| 3,373,915 | A | 3/1968 | Anderson et al. |
| 3,420,360 | A | 1/1969 | Young |
| 3,443,827 | A | 5/1969 | Boezi et al. |
| 3,456,645 | A | 7/1969 | Brock |
| 3,479,561 | A | 11/1969 | Janning |
| 3,567,014 | A | 3/1971 | Feigelman |

(56) References Cited

U.S. PATENT DOCUMENTS 3,675,661 A 7/1972 Weaver
3,707,017 A 12/1972 Paquette
3,732,864 A 5/1973 Thompson et al.
3,792,704 A 2/1974 Parker
3,815,597 A 6/1974 Goettelman
3,861,523 A 1/1975 Fountain et al.
3,878,850 A 4/1975 Gibson et al.
3,884,245 A 5/1975 Anderson et al.
3,924,644 A 12/1975 Anderson et al.
3,941,300 A 3/1976 Troth
3,949,966 A 4/1976 Fabish
3,989,042 A 11/1976 Mitsui et al.
4,020,853 A 5/1977 Nuttall
4,049,005 A 9/1977 Hernandez et al.
4,066,088 A 1/1978 Ensor
4,094,317 A 6/1978 Wasnich
4,207,976 A 6/1980 Herman
4,215,708 A 8/1980 Bron
4,219,032 A 8/1980 Tabatznik et al.
4,253,468 A 3/1981 Lehmbeck
4,291,688 A 9/1981 Kistler
4,303,083 A 12/1981 Burruss, Jr.
4,312,367 A 1/1982 Seeman
4,444,202 A 4/1984 Rubin et al.
4,446,863 A 5/1984 Rubin et al.
4,452,239 A 6/1984 Malem
4,506,683 A 3/1985 Cantrell et al.
4,519,319 A 5/1985 Howlett
4,520,938 A 6/1985 Finke
4,524,769 A 6/1985 Wetterlin
4,577,517 A 3/1986 Knight
4,579,858 A 4/1986 Ferno et al.
4,592,349 A 6/1986 Bird
4,595,024 A 6/1986 Greene et al.
4,597,961 A 7/1986 Etscorn
4,637,407 A 1/1987 Bonanno et al.
4,648,393 A 3/1987 Landis et al.
4,699,136 A 10/1987 Krauser
4,708,151 A 11/1987 Shelar
4,735,217 A 4/1988 Gerth et al.
4,765,348 A 8/1988 Honeycutt
4,771,796 A 9/1988 Myer
4,793,365 A 12/1988 Sensabaugh, Jr. et al.
4,794,323 A 12/1988 Zhou et al.
4,798,310 A 1/1989 Kasai et al.
4,813,536 A 3/1989 Willis
4,819,665 A 4/1989 Roberts et al.
4,830,028 A 5/1989 Lawson et al.
4,836,224 A 6/1989 Lawson et al.
4,846,199 A 7/1989 Rose
4,848,374 A 7/1989 Chard et al.
4,848,563 A 7/1989 Robbins
4,893,639 A 1/1990 White
4,907,606 A 3/1990 Lilja et al.
4,922,901 A 5/1990 Brooks et al.
4,938,236 A 7/1990 Banerjee et al.
4,941,483 A 7/1990 Ridings et al.
4,944,317 A 7/1990 Thal
4,945,931 A 8/1990 Gori
4,947,874 A 8/1990 Brooks et al.
4,947,875 A 8/1990 Brooks et al.
5,005,759 A 4/1991 Bouche
5,020,548 A 6/1991 Farrier et al.
5,027,836 A 7/1991 Shannon et al.
5,031,646 A 7/1991 Lippiello et al.
5,042,509 A 8/1991 Banerjee et al.
5,050,621 A 9/1991 Creighton et al.
5,054,477 A 10/1991 Terada et al.
5,054,478 A 10/1991 Grychowski et al.
5,060,671 A 10/1991 Counts et al.
5,065,776 A 11/1991 Lawson et al.
5,076,297 A 12/1991 Farrier et al.
5,093,894 A 3/1992 Deevi et al.
5,099,833 A 3/1992 Michaels
5,105,831 A 4/1992 Banerjee et al.
5,105,838 A 4/1992 White et al.
5,123,530 A 6/1992 Lee
5,133,368 A 7/1992 Neumann et al.
5,141,004 A 8/1992 Porenski
5,144,962 A 9/1992 Counts et al.
5,152,456 A 10/1992 Ross et al.
5,161,524 A 11/1992 Evans
5,165,392 A 11/1992 Small
5,170,782 A 12/1992 Kocinski
5,178,138 A 1/1993 Walstrom et al.
5,183,062 A 2/1993 Clearman et al.
5,224,498 A 7/1993 Deevi et al.
5,240,012 A 8/1993 Ehrman et al.
5,241,954 A 9/1993 Glenn
5,249,586 A 10/1993 Morgan et al.
5,261,424 A 11/1993 Sprinkel, Jr.
5,269,237 A 12/1993 Baker et al.
5,269,327 A 12/1993 Counts et al.
5,301,622 A 4/1994 Sakuma
5,301,662 A 4/1994 Bagwell et al.
5,303,720 A 4/1994 Banerjee et al.
5,309,900 A 5/1994 Knoch et al.
5,322,075 A 6/1994 Deevi et al.
5,324,498 A 6/1994 Streusand et al.
5,372,148 A 12/1994 McCafferty et al.
5,388,574 A 2/1995 Ingebrethsen
5,449,078 A 9/1995 Akers
5,456,269 A 10/1995 Kollasch
5,479,920 A 1/1996 Piper et al.
5,479,948 A 1/1996 Counts et al.
5,497,791 A 3/1996 Bowen et al.
5,522,380 A 6/1996 Dwork
5,529,078 A 6/1996 Rehder et al.
5,579,934 A 12/1996 Buono
5,591,368 A 1/1997 Fleischhauer et al.
5,596,982 A 1/1997 Blaha-schnabel
5,605,226 A 2/1997 Hernlein
5,613,504 A 3/1997 Collins et al.
5,617,844 A 4/1997 King
5,626,866 A 5/1997 Ebert et al.
5,641,064 A 6/1997 Goserud
5,649,552 A 7/1997 Cho et al.
5,655,520 A 8/1997 Howe et al.
5,666,977 A * 9/1997 Higgins .................. A24F 40/48 131/194
5,666,978 A 9/1997 Counts et al.
5,708,258 A 1/1998 Counts et al.
5,730,118 A 3/1998 Hermanson
5,730,158 A 3/1998 Collins et al.
5,738,086 A 4/1998 Mcmahon et al.
5,746,587 A 5/1998 Racine et al.
5,750,964 A 5/1998 Counts et al.
5,810,164 A 9/1998 Rennecamp
5,819,756 A 10/1998 Mielordt
5,823,179 A 10/1998 Grychowski et al.
5,845,649 A 12/1998 Saito et al.
5,865,171 A 2/1999 Cinquin
5,865,185 A 2/1999 Collins et al.
5,875,774 A 3/1999 Clementi et al.
5,878,752 A 3/1999 Adams et al.
5,881,716 A 3/1999 Wirch et al.
5,881,884 A 3/1999 Podosek
5,894,841 A 4/1999 Voges
5,906,202 A 5/1999 Schuster et al.
5,931,828 A 8/1999 Durkee
5,934,289 A 8/1999 Watkins et al.
5,938,018 A 8/1999 Keaveney et al.
5,944,025 A 8/1999 Cook et al.
5,954,979 A 9/1999 Counts et al.
5,967,310 A 10/1999 Hill
5,975,415 A 11/1999 Zehnal
5,979,460 A 11/1999 Matsumura
5,994,025 A 11/1999 Iwasa et al.
5,996,589 A 12/1999 St. Charles
6,003,737 A 12/1999 Mascitelli
6,026,660 A 2/2000 Lai
6,026,809 A 2/2000 Abrams et al.
6,044,841 A 4/2000 Verdun et al.
6,053,176 A 4/2000 Adams et al.

(56) References Cited

U.S. PATENT DOCUMENTS 6,067,984 A 5/2000 Piper
6,089,857 A 7/2000 Matsuura et al.
6,095,153 A 8/2000 Kessler et al.
6,102,036 A 8/2000 Slutsky et al.
6,105,929 A 8/2000 Davenport et al.
6,125,853 A 10/2000 Susa et al.
6,131,570 A 10/2000 Schuster et al.
6,155,268 A 12/2000 Takeuchi
6,164,287 A 12/2000 White
6,196,218 B1 3/2001 Voges
6,196,232 B1 3/2001 Chkadua
6,211,194 B1 4/2001 Westman et al.
6,234,167 B1 * 5/2001 Cox ........................ A24F 40/70 128/200.14
6,234,169 B1 5/2001 Bulbrook et al.
6,240,917 B1 6/2001 Andrade
6,250,298 B1 6/2001 Gonda et al.
6,253,766 B1 7/2001 Niles et al.
6,269,966 B1 8/2001 Pallo et al.
6,324,261 B1 11/2001 Merte
6,338,443 B1 1/2002 Piper
6,344,222 B1 2/2002 Cherukuri et al.
6,349,728 B1 2/2002 Pham
6,358,060 B2 3/2002 Pinney et al.
6,363,932 B1 4/2002 Forchione et al.
6,381,739 B1 4/2002 Breternitz, Jr. et al.
6,386,371 B1 5/2002 Parsons
6,408,854 B1 6/2002 Gonda et al.
6,425,393 B1 7/2002 Lurie et al.
6,431,363 B1 8/2002 Hacker
6,446,793 B1 9/2002 Layshock
6,450,163 B1 9/2002 Blacker et al.
6,510,982 B2 1/2003 White et al.
6,513,519 B2 2/2003 Gallem
6,532,965 B1 3/2003 Abhulimen et al.
6,536,442 B2 3/2003 St. Charles et al.
6,539,939 B2 4/2003 Rubin
6,557,549 B2 5/2003 Schmidt et al.
6,557,708 B2 5/2003 Polacco
6,584,971 B1 7/2003 Denyer et al.
6,595,203 B1 7/2003 Bird
6,598,607 B2 7/2003 Adiga et al.
6,603,924 B2 8/2003 Brown et al.
6,606,992 B1 8/2003 Schuler et al.
6,606,998 B1 8/2003 Gold
6,612,303 B1 9/2003 Grychowski et al.
6,612,404 B2 9/2003 Sweet et al.
6,615,824 B2 9/2003 Power
6,615,840 B1 9/2003 Fournier et al.
6,619,284 B2 9/2003 Kong
6,622,867 B2 9/2003 Menceles
6,637,430 B1 10/2003 Voges et al.
6,644,304 B2 11/2003 Grychowski et al.
6,655,379 B2 12/2003 Clark et al.
6,656,129 B2 12/2003 Niles et al.
6,672,762 B1 1/2004 Faircloth et al.
6,679,250 B2 1/2004 Walker et al.
6,684,880 B2 2/2004 Trueba
6,688,313 B2 2/2004 Wrenn et al.
6,701,922 B2 3/2004 Hindle et al.
6,708,688 B1 3/2004 Rubin et al.
6,718,969 B1 4/2004 Rubin et al.
6,726,006 B1 4/2004 Funderburk et al.
6,748,945 B2 6/2004 Grychowski et al.
6,772,756 B2 8/2004 Shayan
6,776,156 B2 8/2004 Lurie et al.
6,799,576 B2 10/2004 Farr
6,803,545 B2 10/2004 Blake et al.
6,805,545 B2 10/2004 Slaboden
6,810,883 B2 11/2004 Felter et al.
6,827,573 B2 12/2004 St. Charles et al.
6,848,443 B2 2/2005 Schmidt et al.
6,854,470 B1 2/2005 Pu
6,874,507 B2 4/2005 Farr
6,893,654 B2 5/2005 Pinney et al.
6,904,906 B2 6/2005 Salter et al.
6,904,908 B2 6/2005 Bruce et al.
6,909,840 B2 6/2005 Harwig et al.
6,929,003 B2 8/2005 Blacker et al.
6,954,979 B2 10/2005 Logan
6,955,169 B2 10/2005 Khan
6,986,349 B2 1/2006 Lurie
6,994,083 B2 2/2006 Foley et al.
7,000,775 B2 2/2006 Gelardi et al.
7,015,796 B2 3/2006 Snyder
7,025,066 B2 4/2006 Lawson et al.
7,059,582 B2 6/2006 Adams et al.
7,073,499 B1 7/2006 Reinhold et al.
7,080,643 B2 7/2006 Grychowski et al.
7,082,947 B2 8/2006 Smaldone
7,131,439 B2 11/2006 Blacker et al.
7,185,651 B2 3/2007 Alston et al.
7,186,958 B1 3/2007 Nelson
7,191,780 B2 3/2007 Faram
7,201,165 B2 4/2007 Bruce et al.
7,204,245 B2 4/2007 Johnson et al.
7,270,123 B2 9/2007 Grychowski et al.
D557,209 S 12/2007 Ahlgren et al.
7,329,348 B2 2/2008 Curello et al.
7,334,577 B2 2/2008 Gumaste et al.
7,347,201 B2 3/2008 Djupesland
7,360,536 B2 4/2008 Patel et al.
7,374,048 B2 5/2008 Mazurek
7,387,788 B1 6/2008 Carrara et al.
7,428,905 B2 9/2008 Mua
7,458,374 B2 * 12/2008 Hale ................... A61M 11/042 128/203.26
7,472,701 B2 1/2009 Pfichner et al.
7,488,171 B2 2/2009 St. Charles et al.
D590,990 S 4/2009 Hon
D590,991 S 4/2009 Hon
7,537,009 B2 5/2009 Hale et al.
7,540,286 B2 6/2009 Cross et al.
7,546,703 B2 6/2009 Johnske et al.
7,559,322 B2 7/2009 Foley et al.
7,559,491 B1 7/2009 Chang
7,562,656 B2 7/2009 Gallem et al.
7,568,480 B2 8/2009 Foley et al.
7,571,722 B2 8/2009 Wuttke et al.
7,581,540 B2 9/2009 Hale et al.
7,597,098 B2 10/2009 Gutsell et al.
7,600,511 B2 10/2009 Power et al.
7,600,512 B2 10/2009 Lee et al.
7,621,266 B2 11/2009 Kladders et al.
7,621,403 B2 11/2009 Althoff et al.
7,624,733 B2 12/2009 Riley et al.
7,628,339 B2 12/2009 Ivri et al.
7,634,995 B2 12/2009 Grychowski et al.
7,644,823 B2 1/2010 Gelardi et al.
7,655,331 B2 2/2010 Adams et al.
7,665,460 B2 2/2010 Lindsay et al.
D611,409 S 3/2010 Green et al.
7,726,320 B2 6/2010 Robinson et al.
7,766,013 B2 8/2010 Wensley et al.
7,767,698 B2 8/2010 Warchol et al.
D624,238 S 9/2010 Turner
7,801,573 B2 9/2010 Yazdi et al.
7,814,901 B2 10/2010 Lieberman et al.
7,815,332 B1 10/2010 Smith
7,832,410 B2 11/2010 Hon
7,841,335 B2 11/2010 Harrington et al.
7,841,336 B2 11/2010 Rivera et al.
7,905,228 B2 3/2011 Blacker et al.
7,921,844 B1 4/2011 Santamarina et al.
7,954,487 B2 6/2011 Grychowski et al.
8,006,693 B2 8/2011 Vecellio-none et al.
8,061,352 B2 11/2011 Grychowski et al.
8,113,194 B2 2/2012 Boehm et al.
8,118,713 B2 2/2012 Foley et al.
8,205,622 B2 6/2012 Pan
8,327,849 B2 12/2012 Foley et al.
8,333,197 B2 12/2012 Cross et al.
8,365,742 B2 2/2013 Hon
8,375,957 B2 2/2013 Hon

(56) References Cited

U.S. PATENT DOCUMENTS 8,393,331 B2 3/2013 Hon
8,402,976 B2 3/2013 Fernando et al.
8,490,628 B2 7/2013 Hon
8,539,959 B1 9/2013 Scatterday
8,596,263 B2 12/2013 Piper
8,689,805 B2 4/2014 Hon
8,746,241 B2 6/2014 Cavendish
8,794,434 B2 8/2014 Scatterday et al.
8,844,520 B2 9/2014 Foley et al.
8,851,068 B2 10/2014 Cohen et al.
8,863,752 B2 10/2014 Hon
8,875,715 B2 11/2014 Scatterday et al.
8,893,726 B2 11/2014 Hon
8,897,628 B2 11/2014 Conley et al.
D719,701 S 12/2014 Scatterday
8,899,239 B2 12/2014 Hon
8,905,040 B2 12/2014 Scatterday et al.
8,910,625 B2 12/2014 Mullinger et al.
D721,577 S 1/2015 Scatterday
8,931,492 B2 1/2015 Scatterday
D725,823 S 3/2015 Scatterday et al.
8,991,402 B2 3/2015 Bowen et al.
9,010,335 B1 4/2015 Scatterday
9,022,023 B2 5/2015 Korneff
9,215,895 B2 12/2015 Bowen et al.
9,308,208 B2 4/2016 Wensley et al.
9,408,416 B2 8/2016 Monsees et al.
9,439,455 B2 9/2016 Alarcon et al.
9,532,604 B2 1/2017 Conley et al.
9,566,397 B2 2/2017 Faram
9,757,528 B2 9/2017 Rubin
9,775,380 B2 10/2017 Fernando et al.
9,993,602 B2 6/2018 Davidson et al.
D825,102 S 8/2018 Bowen et al.
10,104,914 B2 10/2018 Force
10,117,466 B2 11/2018 Monsees et al.
10,172,388 B2 1/2019 Sears et al.
D842,536 S 3/2019 Bowen et al.
10,251,425 B2 4/2019 Schuler et al.
10,334,881 B1 7/2019 Conley et al.
10,531,692 B2 1/2020 Althorpe et al.
10,561,176 B2 2/2020 Conley et al.
10,813,387 B2 10/2020 Conley et al.
11,490,459 B2 11/2022 Conley et al.
11,497,864 B2 11/2022 Conley et al.
2001/0015209 A1 8/2001 Zielke
2001/0032643 A1 10/2001 Hochrainer et al.
2001/0032795 A1 10/2001 Weinstein et al.
2001/0052480 A1 12/2001 Kawaguchi et al.
2002/0002975 A1 1/2002 Power
2002/0043554 A1 4/2002 White et al.
2002/0059939 A1 5/2002 Fox
2002/0073995 A1 6/2002 Rubin
2002/0078951 A1 6/2002 Nichols et al.
2002/0157663 A1 10/2002 Blacker et al.
2002/0175164 A1 11/2002 Dees et al.
2002/0189612 A1 12/2002 Rand
2003/0005926 A1 1/2003 Jones et al.
2003/0015197 A1* 1/2003 Hale .................... A61K 31/235 128/200.14
2003/0089377 A1 5/2003 Hajaligol et al.
2003/0136399 A1 7/2003 Foley et al.
2003/0136404 A1 7/2003 Hindle et al.
2003/0150451 A1 8/2003 Shayan
2003/0154991 A1* 8/2003 Fournier ................. A24F 40/50 131/194
2003/0168057 A1 9/2003 Snyder et al.
2004/0002520 A1 1/2004 Soderlund et al.
2004/0031495 A1 2/2004 Steinberg
2004/0050382 A1 3/2004 Goodchild
2004/0079369 A1 4/2004 Sprinkel
2004/0099266 A1 5/2004 Cross et al.
2004/0149296 A1 8/2004 Rostami et al.
2004/0149624 A1 8/2004 Wischusen et al.
2004/0168950 A1 9/2004 Barker
2004/0173224 A1 9/2004 Burgard et al.
2004/0173229 A1 9/2004 Crooks et al.
2004/0182403 A1 9/2004 Andersson et al.
2004/0191322 A1 9/2004 Hansson
2004/0211418 A1 10/2004 Shayan
2004/0221857 A1 11/2004 Dominguez
2004/0237974 A1 12/2004 Min
2004/0249300 A1 12/2004 Miller
2005/0011514 A1 1/2005 Power et al.
2005/0016549 A1 1/2005 Banerjee et al.
2005/0016550 A1* 1/2005 Katase .................... A24F 40/50 131/194
2005/0034723 A1 2/2005 Bennett et al.
2005/0053665 A1 3/2005 Ek et al.
2005/0061759 A1 3/2005 Doucette
2005/0063686 A1 3/2005 Whittle et al.
2005/0067503 A1 3/2005 Katase
2005/0079166 A1 4/2005 Damani et al.
2005/0118545 A1 6/2005 Wong
2005/0145533 A1 7/2005 Seligson
2005/0150488 A1* 7/2005 Dave ....................... A61P 25/36 128/200.14
2005/0169849 A1 8/2005 Farr
2005/0172976 A1 8/2005 Newman et al.
2005/0192538 A1 9/2005 Voege et al.
2005/0205085 A1 9/2005 Blacker et al.
2005/0211243 A1 9/2005 Esser
2005/0244521 A1 11/2005 Strickland et al.
2005/0247313 A1 11/2005 Niles et al.
2005/0268911 A1 12/2005 Cross et al.
2005/0274377 A1 12/2005 Gonda et al.
2006/0016453 A1 1/2006 Kim
2006/0054676 A1 3/2006 Wischusen
2006/0102175 A1 5/2006 Nelson
2006/0150991 A1 7/2006 Lee
2006/0157072 A1 7/2006 Albino et al.
2006/0191546 A1 8/2006 Takano et al.
2006/0191548 A1 8/2006 Strickland et al.
2006/0196518 A1 9/2006 Hon
2006/0243290 A1 11/2006 Reich et al.
2006/0254948 A1 11/2006 Herbert et al.
2006/0255105 A1 11/2006 Sweet
2006/0283468 A1 12/2006 Lipowicz
2007/0006889 A1 1/2007 Kobal et al.
2007/0023036 A1 2/2007 Grychowski et al.
2007/0045288 A1 3/2007 Nelson
2007/0062548 A1 3/2007 Horstmann et al.
2007/0074734 A1 4/2007 Braunshteyn et al.
2007/0098148 A1 5/2007 Sherman
2007/0102013 A1 5/2007 Adams et al.
2007/0107719 A1 5/2007 Blacker et al.
2007/0126290 A1 6/2007 Jaynes et al.
2007/0144514 A1 6/2007 Yeates et al.
2007/0163610 A1 7/2007 Lindell et al.
2007/0215164 A1 9/2007 Mehio
2007/0227534 A1 10/2007 Nobutani et al.
2007/0227536 A1 10/2007 Rivera et al.
2007/0235046 A1 10/2007 Gedevanishvili
2007/0267031 A1* 11/2007 Hon ..................... H05B 1/0291 131/273
2007/0267033 A1 11/2007 Mishra et al.
2007/0277816 A1 12/2007 Morrison et al.
2007/0280652 A1 12/2007 Williams
2007/0283972 A1 12/2007 Monsees et al.
2008/0000763 A1 1/2008 Cove
2008/0023003 A1 1/2008 Rosenthal
2008/0029095 A1 2/2008 Esser
2008/0078385 A1 4/2008 Xiao et al.
2008/0083407 A1 4/2008 Grychowski et al.
2008/0092912 A1 4/2008 Robinson et al.
2008/0121610 A1 5/2008 Nagata et al.
2008/0138423 A1 6/2008 Gonda
2008/0149118 A1 6/2008 Oglesby et al.
2008/0216828 A1 9/2008 Wensley et al.
2008/0228214 A1 9/2008 Hoan et al.
2008/0241255 A1 10/2008 Rose et al.
2008/0257367 A1* 10/2008 Paterno ................. A61M 15/06 131/194
2008/0276947 A1 11/2008 Martzel

(56) References Cited

U.S. PATENT DOCUMENTS

2008/0283050 A1 11/2008 Faram
2008/0286340 A1 11/2008 Andersson et al.
2008/0302375 A1 12/2008 Andersson et al.
2009/0001085 A1 1/2009 Bartz et al.
2009/0004249 A1 1/2009 Gonda
2009/0020128 A1 1/2009 Metzger et al.
2009/0023819 A1 1/2009 Axelsson
2009/0095287 A1 4/2009 Emarlou
2009/0095311 A1 4/2009 Han
2009/0095312 A1 4/2009 Herbrich et al.
2009/0111287 A1 4/2009 Lindberg et al.
2009/0126745 A1 5/2009 Hon
2009/0130874 A1 5/2009 Englund
2009/0133691 A1* 5/2009 Yamada ............... A61M 11/005 128/200.16
2009/0139533 A1 6/2009 Park et al.
2009/0151717 A1 6/2009 Bowen et al.
2009/0151718 A1 6/2009 Hunter et al.
2009/0188490 A1 7/2009 Han
2009/0230117 A1 9/2009 Fernando et al.
2009/0232710 A1 9/2009 Kinsey
2009/0241945 A1 10/2009 Muellner
2009/0255534 A1 10/2009 Paterno
2009/0260641 A1 10/2009 Monsees et al.
2009/0267252 A1 10/2009 Ikeyama
2009/0272377 A1 11/2009 Piper
2009/0272379 A1 11/2009 Thorens et al.
2009/0272820 A1 11/2009 Foley et al.
2009/0283103 A1* 11/2009 Nielsen .................. A24F 40/60 131/273
2009/0288668 A1 11/2009 Inagaki
2009/0288669 A1 11/2009 Hutchens
2009/0293892 A1 12/2009 Williams et al.
2009/0293895 A1 12/2009 Axelsson et al.
2009/0320863 A1 12/2009 Fernando et al.
2010/0000672 A1 1/2010 Fogle
2010/0006092 A1 1/2010 Hale et al.
2010/0024834 A1 2/2010 Oglesby et al.
2010/0031968 A1* 2/2010 Sheikh .................... A24F 40/46 131/347
2010/0122697 A1 5/2010 Przekwas et al.
2010/0156193 A1 6/2010 Rhodes et al.
2010/0163063 A1 7/2010 Fernando et al.
2010/0186757 A1 7/2010 Crooks et al.
2010/0200006 A1 8/2010 Robinson et al.
2010/0200008 A1 8/2010 Taieb
2010/0236562 A1 9/2010 Hearn et al.
2010/0242974 A1 9/2010 Pan
2010/0242976 A1 9/2010 Katayama et al.
2010/0260688 A1 10/2010 Warchol et al.
2010/0275938 A1 11/2010 Roth et al.
2010/0276333 A1 11/2010 Couture
2010/0307116 A1 12/2010 Fisher
2010/0307518 A1 12/2010 Wang
2010/0326436 A1 12/2010 Kaneko
2011/0036346 A1* 2/2011 Cohen ..................... A24F 40/60 128/200.14
2011/0114090 A1 5/2011 Piper
2011/0168169 A1 7/2011 Blacker et al.
2011/0203580 A1 8/2011 Papania et al.
2011/0226236 A1 9/2011 Buchberger
2011/0253139 A1* 10/2011 Guthrie ............ A61M 15/0005 128/203.14
2011/0265806 A1 11/2011 Alarcon et al.
2011/0278189 A1 11/2011 Terry et al.
2012/0000461 A1 1/2012 Grychowski et al.
2012/0060853 A1 3/2012 Robinson et al.
2012/0174914 A1 7/2012 Pirshafiey et al.
2012/0199146 A1 8/2012 Marangos
2012/0255567 A1 10/2012 Rose et al.
2012/0312313 A1 12/2012 Frija
2012/0318882 A1 12/2012 Abehasera
2013/0032159 A1 2/2013 Capuano
2013/0056013 A1 3/2013 Terry et al.
2013/0081642 A1 4/2013 Safari
2013/0125878 A1 5/2013 Hsieh et al.
2013/0192623 A1 8/2013 Tucker et al.
2013/0220315 A1 8/2013 Conley et al.
2013/0255702 A1 10/2013 Griffith et al.
2013/0276903 A1 10/2013 Arcilla et al.
2013/0327323 A1 12/2013 Rubin
2014/0150785 A1* 6/2014 Malik .................. A61M 11/042 128/202.21
2014/0166004 A1 6/2014 Pierro et al.
2014/0290650 A1 10/2014 Ivey
2015/0157056 A1 6/2015 Bowen et al.
2015/0165137 A1 6/2015 Mullinger et al.
2015/0208729 A1* 7/2015 Monsees ............... A61M 15/06 131/329
2015/0224269 A1 8/2015 Alizoti et al.
2015/0231341 A1 8/2015 Korneff
2016/0199594 A1 7/2016 Finger
2016/0262454 A1 9/2016 Sears et al.
2016/0262459 A1 9/2016 Monsees et al.
2016/0338412 A1 11/2016 Monsees et al.
2017/0028161 A1 2/2017 Meyer et al.
2017/0105451 A1 4/2017 Fornarelli
2017/0368273 A1 12/2017 Rubin
2018/0028993 A1 2/2018 Dubief
2018/0070645 A1 3/2018 Monsees et al.
2018/0098576 A1 4/2018 Hedarchet
2019/0069597 A1 3/2019 Mironov
2019/0321570 A1 10/2019 Rubin
2020/0107586 A1 4/2020 Althorpe et al.

FOREIGN PATENT DOCUMENTS

CN 1122213 A 5/1996
CN 1233436 A 11/1999
CN 1298294 A 6/2001
CN 1530041 A 9/2004
CN 1541577 A 11/2004
CN 1887126 A 1/2007
CN 2889333 Y 4/2007
CN 101053685 A 10/2007
CN 200966824 Y 10/2007
CN 200983833 Y 12/2007
CN 200997909 Y 1/2008
CN 201018927 Y 2/2008
CN 201051862 Y 4/2008
CN 101176805 A 5/2008
CN 201064185 Y 5/2008
CN 201067079 Y 6/2008
CN 201067728 Y 6/2008
CN 201072979 Y 6/2008
CN 101228969 A 7/2008
CN 201085044 Y 7/2008
CN 201088138 Y 7/2008
CN 201104488 Y 8/2008
CN 101366554 A 2/2009
CN 201197839 Y 2/2009
CN 201213951 Y 4/2009
CN 201226775 Y 4/2009
CN 201238609 Y 5/2009
CN 201238610 Y 5/2009
CN 101627837 A 1/2010
CN 201379072 Y 1/2010
CN 201379073 Y 1/2010
CN 1607950 B 4/2010
CN 101742985 A 6/2010
CN 101756352 A 6/2010
CN 201491721 U 6/2010
CN 201509598 U 6/2010
CN 101455447 B 7/2010
CN 101869356 A 10/2010
CN 101731750 B 8/2012
DE 4200639 C2 11/1997
DE 19854005 C2 5/2001
DE 19854012 C2 5/2001
DE 102006004484 A1 8/2007
DE 102006041042 A1 3/2008
DE 102007011120 A1 9/2008
EP 0148749 A2 7/1985

(56) References Cited

FOREIGN PATENT DOCUMENTS

| | | | | |
|---|---|---|---|---|
| EP | 0471323 A1 | 2/1992 | | |
| EP | 0532194 A1 | 3/1993 | | |
| EP | 0535695 A2 | 4/1993 | | |
| EP | 0653218 A1 | 5/1995 | | |
| EP | 0354661 B1 | 4/1997 | | |
| EP | 0845220 B1 | 9/2003 | | |
| EP | 1989946 A1 * | 11/2008 | ............ | A24F 40/60 |
| EP | 1618803 B1 | 12/2008 | | |
| EP | 2022350 A1 | 2/2009 | | |
| EP | 1458388 B1 | 4/2009 | | |
| EP | 2110033 A1 | 10/2009 | | |
| EP | 1625336 B1 | 8/2011 | | |
| EP | 2381805 B1 | 12/2012 | | |
| EP | 2608829 A2 | 7/2013 | | |
| EP | 2022349 B1 | 7/2014 | | |
| EP | 2152313 B1 | 9/2014 | | |
| EP | 2186507 B1 | 4/2015 | | |
| EP | 3153038 A2 * | 4/2017 | ............ | A24F 47/00 |
| ES | 2118034 B1 | 4/1999 | | |
| ES | 1070375 U | 8/2009 | | |
| GB | 1025630 A | 4/1966 | | |
| GB | 1065678 A | 4/1967 | | |
| GB | 1381027 A | 1/1975 | | |
| IE | S20060065 A2 | 10/2006 | | |
| IE | S84603 B2 | 6/2007 | | |
| JP | S61254170 A | 11/1986 | | |
| JP | S62278975 A | 12/1987 | | |
| JP | H02-124082 A | 5/1990 | | |
| JP | H02124081 A | 5/1990 | | |
| JP | H02145179 A | 6/1990 | | |
| JP | H02216611 A | 8/1990 | | |
| JP | H0349671 A | 3/1991 | | |
| JP | H03180166 A | 8/1991 | | |
| JP | H0975058 A | 3/1997 | | |
| JP | H10501999 A | 2/1998 | | |
| JP | H11178563 A | 7/1999 | | |
| JP | 2000203639 A | 7/2000 | | |
| JP | 2000236865 A | 9/2000 | | |
| JP | 2001165437 A | 6/2001 | | |
| JP | 2005034021 A | 2/2005 | | |
| JP | 2006504430 A | 2/2006 | | |
| JP | 2006-524494 A | 11/2006 | | |
| JP | 2009108082 A | 5/2009 | | |
| JP | 2010-531188 A | 9/2010 | | |
| JP | 2010532672 A | 10/2010 | | |
| KR | 100193885 B1 | 6/1999 | | |
| KR | 100694546 B1 | 3/2007 | | |
| KR | 20070065194 A | 6/2007 | | |
| KR | 200443406 Y1 | 2/2009 | | |
| KR | 20090008142 U | 8/2009 | | |
| KR | 20090121957 A | 11/2009 | | |
| KR | 20090122159 A | 11/2009 | | |
| KR | 10-0933516 B1 | 12/2009 | | |
| KR | 20100008811 A | 1/2010 | | |
| KR | 20100002123 U | 3/2010 | | |
| KR | 20100028182 A | 3/2010 | | |
| KR | 20100034029 A | 3/2010 | | |
| KR | 20100004364 U | 4/2010 | | |
| KR | 20100006995 U | 7/2010 | | |
| KR | 20100007300 U | 7/2010 | | |
| KR | 20100088626 A | 8/2010 | | |
| RU | 94815 U1 | 6/2010 | | |
| WO | 1995001137 A1 | 1/1995 | | |
| WO | 1997/012639 A1 | 4/1997 | | |
| WO | 9729799 A2 | 8/1997 | | |
| WO | 2000005976 A1 | 2/2000 | | |
| WO | 2000028842 A1 | 5/2000 | | |
| WO | 02074370 A2 | 9/2002 | | |
| WO | 03/037412 A2 | 5/2003 | | |
| WO | 03047763 A1 | 6/2003 | | |
| WO | 03053500 A1 | 7/2003 | | |
| WO | 2003055486 A1 | 7/2003 | | |
| WO | 2003056948 A1 | 7/2003 | | |
| WO | 2003082031 A1 | 10/2003 | | |
| WO | 2003/094900 A1 | 11/2003 | | |
| WO | 2003103387 A2 | 12/2003 | | |
| WO | 2004002446 A1 | 1/2004 | | |
| WO | 2004064548 A1 | 8/2004 | | |
| WO | 2004/080216 A1 | 9/2004 | | |
| WO | 2004076289 A2 | 9/2004 | | |
| WO | 2004/095955 A1 | 11/2004 | | |
| WO | 2005020726 A1 | 3/2005 | | |
| WO | 2006/004646 A1 | 1/2006 | | |
| WO | 2006015070 A1 | 2/2006 | | |
| WO | 2006053082 A2 | 5/2006 | | |
| WO | 2006/082571 A1 | 8/2006 | | |
| WO | 2006133101 A2 | 12/2006 | | |
| WO | 2007026131 A1 | 3/2007 | | |
| WO | 2007/078273 A1 | 7/2007 | | |
| WO | 2007131449 A1 | 11/2007 | | |
| WO | 2008048234 A2 | 4/2008 | | |
| WO | 2008077271 A1 | 7/2008 | | |
| WO | 2008/121610 A1 | 10/2008 | | |
| WO | 2009/001085 A2 | 12/2008 | | |
| WO | 2009/079641 A2 | 6/2009 | | |
| WO | 2009069519 A1 | 6/2009 | | |
| WO | 2010023561 A1 | 3/2010 | | |
| WO | 2010/045671 A1 | 4/2010 | | |
| WO | 2010140841 A2 | 12/2010 | | |
| WO | 2012026963 A2 | 3/2012 | | |
| WO | 2012026963 A3 | 5/2012 | | |
| WO | 2013083636 A1 | 6/2013 | | |
| WO | 2015198015 A1 | 12/2015 | | |
| WO | 2016012774 A1 | 1/2016 | | |
| WO | 2016075436 A1 | 5/2016 | | |
| WO | 2016079152 A1 | 5/2016 | | |
| WO | 2018172429 A1 | 9/2018 | | |

OTHER PUBLICATIONS

International Preliminary Report on Patentability received for International Application No. PCT/US2011/001438, mailed on Nov. 4, 2012, 8 pages.

International Search Report received for International Application No. PCT/US2011/001438 issued on Mar. 28, 2012, 4 pages.

Notice of Allowance issued for CA Application No. 2,808,836, issued on Dec. 27, 2019, 1 page.

Written Opinion received for International Application No. PCT/US2011/001438, mailed on Mar. 28, 2012, 4 pages.

"European Extended Search Report for Application No. 11820272.0", dated May 8, 2015, 7 pages.

Bhatnagar, et al., "Electronic Cigarettes A Policy Statement From the American Heart Association", Electronic Cigarettes, Mar. 16, 2015, pp. 1419-1436.

Brown, et al., "Electronic Cigarettes:product characterisation and design considerations", Tob Control; vol. 23, 2014, pp. ii4-ii10.

Smaldone, "Assessing New Technologies: Patient—Device Interactions and Deposition", Respiratory Care; vol. 50, No. 9, Sep. 2005, pp. 1151-1160.

European Notice of Opposition received for European Patent Application No. 21171539.6, mailed on May 12, 2025.

European Summons to Attend Oral Proceedings Corresponding to Application No. 21171539.6, mailed Dec. 23, 2025.

Thomas A. Perfetti. (1978). Investigation of Nicotine Transfer to Mainstream Smoke. I. Synthesis of Nicotine Salts. Chemical Research RDM, No. 34, No. of Pages: 17.

Thomas Eissenberg. (2010). Electronic nicotine delivery devices: ineffective nicotine delivery and craving suppression after acute administration. NIH, Tob Control. 19(1): 87-88.

Kevin Hatch et al. (2006). Preliminary Evaluation of a Commercially Available Electric Aerosol Inhaler From China. RJ Reynolds Records; Master Settlement Agreement. https://www.industrydocuments.ucsf.edu/all-industries/documents/viewer/?iid=nyvy0228&id=nyvy0228&db-set=documents&industry=all-industries&rtool=metadata.

William Oldendorf, M.D. et al. (1979). pH Dependence of Blood-Brain Barrier Permeability to Lactate and Nicotine. Stroke vol. 10, No. 5.

Jeffrey I. Seeman et al. (2004). On the Deposition of Volatiles and Semivolatiles from Cigarette Smoke Aerosols: Relative Rates of

(56) References Cited

OTHER PUBLICATIONS

Transfer of Nicotine and Ammonia from Particles to the Gas Phase. Chem. Res. Toxicol., 17, 1020-1037.
Michael Dixon et al. (2000). Mini-Review On the Transfer of Nicotine from Tobacco to the Smoker. A Brief Review of Ammonia and "pH" Factors. Contributions to Tobacco Research. vol. 19, No. 2.
James F. Pankow. (2001). A Consideration of the Role of Gas/Particle Partitioning in the Deposition of Nicotine and Other Tobacco Smoke Compounds in the Respiratory Tract. Chemical Research in Toxicology. vol. 14, No. 11.
Joyce Mccann et al. (1975). Detection of carcinogens as mutagens in the *Salmonella*/microsome test: Assay of 300 chemicals. Proc. Nat. Acad. Set. USA vol. 72, No. 12, pp. 5135-5139.
William H. Oldendorf et al. (1993). Blood-brain barrier penetration abolished by N-methyl quaternization of nicotine. Proc. Natl. Acad. Sci. USA vol. 90, pp. 307-311.
Scott L Tomar et al. (1997). Review of the evidence that pH is a determinant of nicotine dosage from oral use of smokeless tobacco. Tobacco Control;6:219-225.
Kuo-Mei Chang et al. (1995). The Application of A Physiologically-Based Pharmaco-kinetic (PBPK) Nicotine Model to Estimate Nicotine Uptake in Smokers. 14 pages.
John Robinson. (2008). Considering the Absorption of Nicotine From Tobacco and Smoke: Pulmonary vs Oral Absorption. 44 pages.
R. J. Robinson et al. (2001). Deposition of Cigarette Smoke Particles in the Human Respiratory Tract. Aerosol Science and Technology 34: 202-215.
T. A. Perfetti et al. The Transfer of Nicotine From Nicotine Sal ts to Mainstream Smoke. R. J. Reynolds Tobacco Company. 36 pages.
Richard J. Bastin et al. (2000). Salt Selection and Optimisation Procedures for Pharmaceutical New Chemical Entities. Organic Process Research & Development, 4, 427-435.
SCENIHR (Scientific Committee on Emerging and Newly Identified Health Risks). (2010). Addictiveness and Attractiveness of Tobacco Additives, Pre-consultation opinion.
Dr. James M.MacDougall Ph.D. et al. (2010). Selective Cardiovascular Effects of Stress and Cigarette Smoking. 10 pages.
Judith K. Ockene et al. (1990). The Relationship of Smoking Cessation to Coronary Heart Disease and Lung Cancer in the Multiple Risk Factor Intervention Trial (MRFIT). Am J Public Health; 80:954-958.
Igor Gonda et al. (2009). Smoking Cessation Approach Via Deep Lung Delivery of 'Clean' Nicotine. Respiratory Drug Delivery Europe. p. 57-62.
Thomas A. Perfetti. (1983). Structural Study of Nicotine Salts. Beitrage zur Tabakforschung International. vol. 12, No. 2.
1988). American Society for Clinical Pharmacology and Therapeutics. p. 186.
Alan Rodgman et al. (2009). The Chemical Components of Tobacco and Tobacco Smoke. 407 pages.
George B. Weiss. (1966). The Effect of pH on Nicotine-Induced Contracture and Ca45 Movements in Frog Sartorius Muscle. The Journal of Pharamcology and Experimental Therapeutics. vol. 154, No. 3.
Richard R. Baker et al. (2004). The effect of tobacco ingredients on smoke chemistry. Part II: Casing ingredients. Food and ChemicalToxicology 42S S39-S52.
Jeffrey I. Seeman et al. (1999). The Form of Nicotine in Tobacco. Thermal Transfer of Nicotine and Nicotine Acid Salts to Nicotine in the Gas Phase. J. Agric. Food Chem., 47, 5133-5145.
Richard M. Effros et al. (1969). The In Vivo pH of the Extravascular Space of the Lung. The Journal of Clinical Investigation vol. 48.
Janet Travell. (1940). The Influence of the Hydrogen Ion Concentration on the Absorption of Alkaloids From the Stomach. From the Department of Pharmacology, Cornell University Medical College, New York. 21-33.
Jeffrey I. Seeman et al. (2008). The possible role of ammonia toxicity on the exposure, deposition, retention, and the bioavailability of nicotine during smoking. Food and Chemical Toxicology 46; 1863-1881.
Charlene H. Callicutt et al. (2006). The role of ammonia in the transfer of nicotine from tobacco to mainstream smoke. Regulatory Toxicology and Pharmacology 46; 1-17.
(2008). United States International Trade Commision Rulings And Harmonized Tariff Schedule. 1 page.
Richard R. Baker et al. (2004). The pyrolysis of tobacco ingredients. J. Anal. Appl. Pyrolysis 71; 223-311.
R.A. Blevins, Jr. et al. (1973). Implications and Activities Arising From Correlation of Smoke pH With Nicotine Impact, Other Smoke Qualities, and Cigarette Sales. 31 pages.
A. J. Sensabaugh, Jr. et al. (1967). A New Technique For Determining The pH Of Whole Tobacco Smoke. Research Department, R. J. Reynolds Tobacco Company. p. 25-30.
John C. Leffingwell et al. (1972). Tobacco Flavoring for Smoking Products. R. J. Reynolds Tobacco Company. p. 1-72.
Scott L. Tomar et al. (1997). Review Article: Review of the Evidence That pH Is a Determinant of Nicotine Dosage from Oral Use of Smokeless Tobacco. Tobacco Control , Autumn, vol. 6, No. 3, pp. 219-225.
Anna Trtchounian, M.S. et al. (2010). Conventional and electronic cigarettes (e-cigarettes) have different smoking characteristics. Nicotine & Tobacco Research, vol. 12, No. 9, 905-912.
Jeffrey I. Seeman (2005). Using "Basic Principles" To Understand Complex Science: Nicotine Smoke Chemistry and Literature Analogies. Journal of Chemical Education. vol. 82 No. 10.
David Horowitz. (2002). Letter from The Compounding Pharmacy, Department of Health & Human Services. 3 pages.
Charlene H. Callicutt et al. (2005). The Ability of the FTC Method to Quantify Nicotine as a Function of Ammonia in Mainstream Smoke. p. 1-21.
Stefania Nicoli et al. (2007). Mammalian Tumor Xenografts Induce Neovascularization in Zebrafish Embryos. Cancer Res; 67: (7).
Specification and Drawings for U.S. Appl. No. 12/843,917, filed Jul. 27, 2010.
Specification and Drawings for U.S. Appl. No. 61/271,819, filed Jul. 27, 2009.
Specification for U.S. Appl. No. 61/273,097, filed Jul. 31, 2009.
Perfetti, T. A. (1983). Structural Study of Nicotine Salts. Beiträge Zur Tabakforschung / Contributions to Tobacco Research, 12(2).
Fournier, J. A. et al. (2001) Thermal Pathways for the Transfer of Amines, Including Nicotine, to the Gas Phase and Aerosols. Heterocycles, 55 (1).
Kalman, D. et al. (2005). Does nicotine do what we think it does? A meta-analytic review of the subjective effects of nicotine in nasal spray and intravenous studies with smokers and nonsmokers. Nicotine & Tobacco Research, 7(3), 317-333.
Judasburrito. (Nov. 26, 2008). Sailebao liquid component list. E-Cigarette Forum. https://www.e-cigarette-forum.com/threads/sailebao-liquid-component-list.3867/.
Vansickel, A. R. et al. (2010). A Clinical Laboratory Model for Evaluating the Acute Effects of Electronic "Cigarettes": Nicotine Delivery Profile and Cardiovascular and Subjective Effects. Cancer Epidemiology, Biomarkers & Prevention, 19(8).
Lauterbach, J. (2000). A critical assessment of recent work on the application of gas/particle partitioning theories to cigarette smoke. Beiträge Zur Tabakforschung International/Contributions to Tobacco Research, 19(2), 65-83.
Ji-Zhou Dong, J. et al. (2000). A Simple Technique for Determining the pH of Whole Cigarette Smoke. Beiträge Zur Tabakforschung International/Contributions to Tobacco Research, 19(1), 33-48.
Burn J.H. et al. (1958) Action of Nicotine on the Heart. British Medical Journal. 137-139.
Lee, L.-Y. et al. (2007). Airway irritation and cough evoked by inhaled cigarette smoke: Role of neuronal nicotinic acetylcholine receptors. Pulmonary Pharmacology & Therapeutics, 20, 355-364.
Heyder, J. (1982). Alveolar deposition of inhaled particles in humans. American Industrial Hygiene Association Journal, 43(11), 864-866.

(56) References Cited

OTHER PUBLICATIONS

Bao, M. et al. (2010). An improved headspace solid-phase microextraction method for the analysis of free-base nicotine in particulate phase of mainstream cigarette smoke. Analytica Chimica Acta, 663, 49-54.
Baker, R.R. et al. (2004). An overview of the effects of tobacco ingredients on smoke chemistry and toxicity. Food and Chemical Toxicology, 42S, S53-S83.
Bates, Clive et al. (1999). Tabacco Additives, Cigarette Engineering and Nicotine Addiction. Imperial Cancer Research Fund. 36 pages.
Benowitz, N. L. (2009). Pharmacology of Nicotine: Addiction, Smoking-Induced Disease, and Therapeutics. Annual Review of Pharmacology and Toxicology, 49, 57-71.
Wayne GF et al. Brand differences of free-base nicotine delivery in cigarette smoke: the view of the tobacco industry documents. Tobacco Control. 2006; 15:189-198.
Buchhalter, A. R. et al. (2001). Withdrawal-suppressing effects of a novel smoking system: comparison with own brand, not own brand, and de-nicotinized cigarettes. Nicotine & Tobacco Research, 3, 111-118.
Brown, C. R. et al. (1989). Caffeine and Cigarette Smoking: Behavioral, Cardiovascular, and Metabolic Interactions. Pharmacology Biochemistry & Behavior, 34, 565-570. Pergamon Press plc.
D. W. Bombick et al. (1998) Chemical and Biological Studies of a New Cigarette that Primarily Heats Tobacco. Part 3. In Vitro Toxicity of Whole Smoke. Food and Chemical Toxicology 36, 191-197.
B. Reed Bombick et al. (1997) Chemical and Biological Studies of a New Cigarette that Primarily Heats Tobacco. Part 2. In Vitro Toxicology of Mainstream Smoke Condensate. Food and Chemical Toxicology. 36, 183-190.
M. F. Borgerding et al. (1997) Chemical and Biological Studies of a New Cigarette that Primarily Heats Tobacco. Part 1. Chemical Composition of Mainstream Smoke. Food and Chemical Toxicology. 36, 169-182.
James F. Pankow et al. (1997). Conversion of Nicotine in Tobacco Smoke to Its Volatile and Available Free-Base Form through the Action of Gaseous Ammonia. Environ. Sci. Technol. 31, 2428-2433.
M. Dezelic et al. (1967). Determination of structure of some salts of nicotine, pyridine and N-methylpyrrolidine on the basis of their infra-red spectra. Spectrochimica Acta, 1967. vol. 23A, pp. 1149 to 1158.
C. Bullen et al. (2010). Effect of an electronic nicotine delivery device (e cigarette) on desire to smoke and withdrawal, user preferences and nicotine delivery: randomised cross-over trial. Tobacco Control. 19:98-103.
S.G. Burch et al. (1993). Effect of pH on Nicotine Absorption and Side Effects Produced by Aerosolized Nicotine. Journal of Aerosol Medicine vol. 6, No. 1, 45-52.
K. Torikai et al. (2004). Effects of temperature, atmosphere and pH on the generation of smoke compounds during tobacco pyrolysis. Food and Chemical Toxicology 42, 1409-1417.
Thilo Paschke et al. (2002). Effects of Ingredients on Cigarette Smoke Composition and Biological Activity: A Literature Overview. Beiträge zur Tabakforschung International/Contributions to Tobacco Research. vol. 20, 3.
Jack E Henningfield et al. (1995). Estimation of available nicotine content of six smokeless tobacco products. Tobacco Control; 4:57-61.
Richard C Frecker et al. (1988). Generation of a submicrometre nicotine aerosol for inhalation. Medical & Biological Engineering & Computing. 4 pages.
F.V. Wells. Glycerin As A Constituent of Cosmetics and Toilet Preparations. SCC Media Library & Resource Center. 19-25.
Neha Gowadia et al. (2010). A transport model for nicotine in the tracheobronchial and pulmonary region of the lung. Inhalation Toxicology; 22(1): 42-48.
D. Layten Davis et al. (1999). Tobacco Production, Chemistry and Technology. Blackwell Science Ltd. 10 pages.
Franjo Grotenhermen et al. (2007). Developing limits for driving under cannabis. The Authors. Journal compilation, Society for the Study of Addiction. 1-8.
Dr. K. Rothwell et al. (1999). Health Effects of Interactions between Tobacco Use and Exposure to other Agents. World Health Organization. https://www.inchem.org/documents/ehc/ehc/ehc211.htm.
Regina Benjamin et al. (2010). How Tobacco Smoke Causes Disease: The Biology and Behavioral Basis for Smoking-Attributable Disease. A Report of the Surgeon General. 727 pages.
Richard D. Hurt et al. (1998). Prying Open the Door to the Tobacco Industry's Secrets About Nicotine. Health Law and Ethics. vol. 280, No. 13; 1173-1181.
Peter Boyle (ed.) et al. (2010). Tobacco: Science, policy and public health (2nd edn). Chapter 5. 41 pages.
Lois Keithly et al. (2005). Industry research on the use and effects of levulinic acid: A case study in cigarette additives. Nicotine & Tobacco Research; vol. 7, No. 5, 761-771.
Janet Travell. (1940). Influence of pH on Absorption of Nicotine from Urinary Bladder and Subcutaneous Tissues. The Department of Pharmacology, Cornell University Medical College, New York City. 552-556.
Thomas Adam et al. (2009). Investigation of Tobacco Pyrolysis Gases and Puff-by-puff Resolved Cigarette Smoke by Single Photon Ionisation (SPI)—Time-of-flight Mass Spectrometry (TOFMS). Beiträge zur Tabakforschung International/Contributions to Tobacco Research. vol. 23, No. 4.
Richard M. Effros et al. (1983). The In Vivo pH of the Extravascular Space of the Lung. The Journal of Clinical Investigation vol. 48, 1983-1996.
(2005). Summary of Evaluations Performed by the Joint FAO/WHO Expert Committee on Food Additives. JECFA Evaluations—Benzoic Acid. https://www.inchem.org/documents/jecfa/jeceval/jec_184.htm.
(2003). Summary of Evaluations Performed by the Joint FAO/WHO Expert Committee on Food Additives. JECFA Evaluations—Levulinic Acid. https://www.inchem.org/documents/jecfa/jeceval/jec_1266.htm.
(2003). Summary of Evaluations Performed by the Joint FAO/WHO Expert Committee on Food Additives. JECFA Evaluations—Pyruvic Acid. https://www.inchem.org/documents/jecfa/jeceval/jec_2072.htm.
(2005). Summary of Evaluations Performed by the Joint FAO/WHO Expert Committee on Food Additives. JECFA Evaluations—Sorbic Acid. https://www.inchem.org/documents/jecfa/jeceval/jec_2181.htm.
(2010). Comment on Gas/Particle Partitioning of Two Acid-Base Active Compounds in Mainstream Tobacco Smoke: Nicotine and Ammonia. J. Agric. Food Chem., 58, 9287-9288.
Eun M. Lee et al. (2004). Quantitative comparisons between a nicotine delivery device (Eclipse) and conventional cigarette smoking. Nicotine & Tobacco Research vol. 6, No. 1, 95-102.
J.C. Leffingwell. (1999). Chapter 8, Leaf Chemistry BA Basic Chemical Constituents of Tobacco Leaf and Differences among Tobacco Types. 21 pages.
Patrick M. Lippiello et al. (1989). Enhancement of Nicotine Binding to Nicotinic Receptors by Nicotine Levulinate and Levulinic Acid. Biochemical/Biobehavioral R&D, R&DM, No. 267.
(/Terms/view/S06027) (/terms/view/S06025) stoichiometry. 2005-2021 International Union of Pure and Applied. https://doi.org/10.1351/goldbook.S06026.
Jed E. Rose. (2006). Nicotine and nonnicotine factors in cigarette addiction. Psychopharmacology, 184: 274-285.

* cited by examiner 2
54
-51-
-56-
58
55
58
55
57
41

Fig. 32B 2120
2123
2400′
2420
2404′
2425
2403′
2402′
2401′
I
II
III
IV
2430

SYSTEMS AND METHODS OF AEROSOL DELIVERY WITH AIRFLOW REGULATION

RELATED APPLICATION

The present application is a continuation of pending U.S. patent application Ser. No. 16/458,702 filed on Jul. 1, 2019 which is a continuation of U.S. patent application Ser. No. 15/672,021 filed on Aug. 8, 2017, now abandoned, which is a continuation-in-part of U.S. patent application Ser. No. 13/969,847 filed on Aug. 19, 2013 and issued as U.S. Pat. No. 9,757,528 on Sep. 12, 2017, which is a continuation-in-part of U.S. patent application Ser. No. 12/806,874 filed on Aug. 23, 2010, now abandoned, the subject matter of which applications is incorporated herein by reference.

FIELD OF THE DISCLOSURE

The present disclosure provides an aerosol delivery device having structures and methods for providing controlled airflow and aerosol entrainment through the device to optimize aerosol delivery under a greater range of conditions.

BACKGROUND OF THE DISCLOSURE

The term "aerosol" is understood in the context of the present disclosure to mean a preferably nebulous collection of atomized liquid droplets or fine powder particles, or vapor, often suspended in air that can be available for inhalation. Aerosol particles can be solid or liquid fine particles and come in a variety of shapes. The term "aerosolizable substance" as used herein means any substance, including, but not limited to aqueous liquids, suspensions, and solids and those containing a pharmacologically active ingredient, which is capable of becoming an aerosol or having already become an aerosol. The term "aerosolized therapy" as used herein means any aerosolized liquid or powder, or the condensation aerosol that forms after vaporization of a substance, regardless of whether it is physiologically active. The expression "medicament formulation" used in the present disclosure is understood to include, apart from medicaments, also therapeutic agents or the like, in particular therefore all types of agents for inhalation, including those which are active and non-active ingredients. Aerosols may also comprise water, saline, or flavoring agents. Some substances are aerosolizable when placed in a liposomal formulation for aerosolization.

In most instances, aerosol particles with a mass median aerodynamic diameter, MMAD, between 0.5 and 5 micrometers are ideal for lung delivery; whereas, aerosol particles with a MMAD of greater than 5 micrometers have deposition in the upper airways rather than the lungs. Aerosol particles with a MMAD of 2 to 5 micrometers have deposition in the bronchi and bronchioles, and aerosol particles with a MMAD of less than 2 micrometers have deposition in the alveoli, for deep lung and/or systemic delivery. Selection of MMAD is one method of targeting aerosols to different airway regions.

The use of aerosol delivery devices of known designs and configurations, including nebulizers, vaporizers, and other inhalers, is known in the prior art.

More specifically, aerosol delivery devices of known designs and configurations previously devised and utilized for the purpose of administering medicament dosages through conventional methods and apparatuses are known to consist basically of familiar, expected, and obvious structural configurations, notwithstanding the myriad of designs encompassed by the crowded prior art which has been developed for the fulfillment of countless objectives and requirements. Such aerosol delivery devices make it possible to introduce substances to the respiratory system generally via simple inhalation.

By way of example International Patent Application and WO 03/047763 A1, European Patent Applications EP 0 471 323 A1 and EP 0 653 218 A1 and U.S. Pat. Nos. 5,241,954 and 7,559,491 disclose an air jet nebulizer that passes a stream of pressurized air into a liquid reservoir, which forces the liquid onto a baffle to effect aerosol generation. U.S. Pat. Nos. 3,989,042 and 7,472,701 disclose an ultrasonic nebulizer, which utilizes a piezoelectric motor or piezo-oscillating element that vibrates at ultrasonic frequencies, to pass liquid through a vibratable aperture mesh or membrane, to effect aerosol generation. Some nebulizers can be hand-held and portable, as they are battery operated, and sometimes, rechargeable, as described in U.S. Pat. Nos. 6,637,430 and 7,600,511. Nebulizers can be used with spacers and holding chambers. Nebulizers can also be fitted with adapters to provide positive expiratory pressure therapy, and/or positive airway pressure therapy, such as those disclosed by U.S. Pat. Nos. 6,253,766; 6,904,906; and 7,191,780.

Nebulizers may also conserve medication by incorporating a pump that is breath-activated, and may be turned on and off depending on the stage in the patient's breathing cycle. The breathing cycle includes the stages of inhalation, pause, and exhalation. For instance, U.S. Pat. No. 5,894,841 describes a pressure transducer, responsive to inhalation, that may activate the pump during inhalation, and inactivate the pump when inhalation is no longer detected, i.e., during exhalation, or with a timer. Likewise, U.S. Pat. Nos. 7,131,439 and 7,634,995 describe a breath activated nebulizer, with a jet that becomes active during inhalation.

Other means to aerosolize a liquid, without the use of compressed air or a piezoelectric motor, include U.S. Pat. No. 7,621,266; which describes a liquid reservoir whose contents are forced through one or more nozzles under pressure, by mechanical means, to generate aerosol for delivery. The velocity of the emitted droplet stream may be slowed with nozzles angled toward one another.

Electricity can also be used to generate aerosol by vaporizing a medicament formulation with heat from an electrically resistive heating element, electrothermal transducer, or thermo-electrical converter, and allowing that vaporized substance to condense or react in the airflow of the device, as described in U.S. Pat. Nos. 5,881,716 and 7,540,286. Electricity used to power a vaporizer may also be generated from a micro power source, such as a micro-fuel cell, as described in U.S. Pat. No. 7,665,460. More information about fuel cells are revealed by U.S. Pat. Nos. 7,059,582, 7,329,348 and 7,655,331. Whereas, U.S. Pat. No. 7,581,540 discloses a vaporizer that uses heat generated by the ignition of a fuel.

Unlike nebulizers, metered dose inhalers, MDI, generally consist of a canister filled with a liquefied gas propellant, stabilizing excipients, and medicament. The canister contains a metering valve that dispenses into a discharge nozzle within the inhaler. U.S. Pat. Nos. 3,732,864; 4,291,688; 7,597,098; and 7,600,512 describe metered dose inhalers, some of which are self-actuated by patient breath, and include a dosage counter. Some MDIs contain a spacer region, as disclosed by U.S. Pat. Nos. 5,178,138 and 6,718,969; while other MDIs attach to a separate holding chamber, as disclosed by U.S. Pat. No. 6,240,917. Spacers and holding chambers can come in many different sizes and shapes, such as the conical shape disclosed in U.S. Pat. No. 5,178,138, and may include spiral or impeller-like baffles to generate a rotational flow of aerosolized air, as disclosed in U.S. Pat. Nos. 5,309,900 and 5,596,982 and 7,562,656; and may be made of an electrostatically neutral material, or contain an anti-static coating as disclosed in U.S. Pat. No. 7,562,656, to avoid attraction and impaction of aerosol droplets with the device.

Medicament is not limited to a liquid format. Solid particles can also be inhaled as a fine powder, without a propellant, if they are dispersed into an airflow stream using a dry powder inhaler, DPI, such as disclosed in U.S. Pat. Nos. 4,524,769 and 7,624,733. Dry powder inhalers may also use a vibratable plate to disaggregate solid medicament particles, as described in U.S. Pat. No. 7,334,577.

The supply of a fluid fed to an aerosol generator can be controlled as disclosed in U.S. Pat. Nos. 7,628,339 and 7,360,536 to affect dosing of a medicament. Electronic means can be employed to achieve such control.

In aerosol delivery devices, valves, such as duckbill valves and flapper valves, a flexible valve that bends in response to a pressure differential, can be employed to allow aerosol to reach the patient only during inhalation, as to reduce aerosol loss. Such valves may also be employed to prevent backflow of a patient's expired air into the device. Additionally, filters may be employed to reduce exposure by caregivers of contaminated patient air and aerosol. Such valves and filters are described by U.S. Pat. Nos. 7,571,722; 7,204,245; and 6,904,906.

Most aerosol delivery occurs through the mouth, such as via a mouthpiece, hose, or facemask, but nasal delivery of aerosol is also possible. U.S. Pat. No. 7,347,201 describes such nasal delivery devices, which utilize a nosepiece or prongs, instead of a mouthpiece end. Face masks are also commonly used with aerosol delivery devices, as described by U.S. Pat. No. 7,082,947. Some aerosol delivery devices can also be placed in a respiratory circuit to provide aerosols to patients on mechanical ventilation, as described in U.S. Pat. No. 5,178,138, among others.

As there is a myriad of ways to generate aerosol, there is also a myriad of ways to store the medicament formulation, including liquid reservoirs, pressurized canisters, as well as in blister strips or dosage packets, as described in U.S. Pat. No. 7,334,577, and in cassettes or cartridges, as described in U.S. Pat. No. 7,540,286.

There exist numerous other ways to attempt to enhance aerosol delivery efficiency. Aerosols can be warmed to reduce particle size, as disclosed by U.S. Pat. No. 6,131,570. Aerosols can be released at a specific point in the breathing cycle, as inspiratory flow rate and inspiratory volume are detected by sensors and computed by microprocessors, as disclosed by U.S. Pat. No. 6,250,298.

Some respiratory devices may measure or indicate airflow. U.S. Pat. No. 6,656,129 describes a flow based incentive spirometer. U.S. Pat. No. 6,679,250 describes a combination spirometer or peak flow meter and nebulizer system to measure flow rate of breath exhaled during the exhale phase. U.S. Pat. Nos. 6,904,908 and 7,201,165 describe a flow/visual indicator for an aerosol medication delivery system. U.S. Pat. No. 6,955,169 describes an inhaler device with a float to show airflow.

U.S. Pat. No. 7,073,499 describes an inhaler with airflow regulation that is limited in scope to the involuntary regulation of an airflow passage by the force of inhaled airflow, and cannot be adjusted by other means; such as by manual adjustment by hand or by electro-mechanical, motor, means. Therefore, the involuntary airflow regulation, and thus airflow rate, of the device disclosed by U.S. Pat. No. 7,073,499 is constant and not controllable, and provides a limited range of airflow resistance that must be commensurate with the user's inspiratory rate. The threshold of the device cannot be adjusted. U.S. Pat. No. 7,185,651 describes a dry powder inhaler with a threshold valve and a flow regulating valve that allows actuation of the device. However, both the threshold valve and flow regulating valve are non-adjustable, and only allow for a very limited range of airflow. Likewise, U.S. Pat. No. 6,655,379 also describes a device with a non-adjustable, flow restrictor valve that limits flow rates to less than 17 liters per minute.

U.S. Pat. No. 6,606,992 relates to techniques for regulating the flow of inspired gases when dispersing a pharmaceutical formulation. More specifically, this system relates to the aerosolization of pharmaceutical formulations using energy created by patient inhalation, to synchronize aerosol generation with inhalation, after a threshold vacuum is exceeded. In this case, inspired gases are used to disperse and deagglomerate a powdered pharmaceutical formulation for deep lung delivery. This device is very limited in means to generate aerosols. The major flaw of this system is that there are no calibrated airflow resistance settings, so that if a restriction mechanism is adjusted, there is no way of knowing what the resulting airflow rate will be, without measuring the airflow of the device with laboratory instruments, each and every time the device is altered. As such, the airflow rate may be adjusted incorrectly by users and care givers to produce a less than desirable outcome for aerosol delivery. Unlike the present disclosure, the device disclosed by U.S. Pat. No. 6,606,992 is also limited by lack of a spacer, holding chamber, reserve chamber, region so that aerosol may not have adequate time and space to disperse properly so that aerosol velocity, and/or aerosolized airflow velocity, cannot be slowed and/or controlled as effectively. Furthermore, without a spacer region, aerosol particles may not deagglomerate or evaporate as effectively, which is needed to obtain aerosols of a higher percentage of decreased particle size for improved lung delivery.

The devices disclosed by Rubin in U.S. Pat. Nos. 4,444,202; 6,539,939; 6,708,688; and 6,718,969, and by Dwork in U.S. Pat. No. 5,522,380 describe respiratory therapy systems, with calibrated airflow resistance settings, that can perform both lung exercise and aerosol delivery when coupled to a nebulizer device. However, these large and complex systems have inherent limitations and are not designed to provide controlled airflow through the device to optimize aerosol delivery under a greater range of conditions. U.S. Pat. Nos. 4,444,202 and 5,522,380 are not dedicated aerosol delivery devices, themselves, but U.S. Pat. Nos. 6,539,939; 6,708,688; and 6,718969 can deliver metered dose aerosol, MDI. However, MDI inhalers are typically unable to efficiently deliver aerosol particles with a MMAD small enough for deep lung delivery, and thus cannot provide adequate systemic delivery of a therapeutic substance via the pulmonary route. Therefore, the devices specified by U.S. Pat. Nos. 4,444,202; 5,522,380; 6,539,939; 6,708,688; and 6,718,969 have only a limited range of treatments options available to them. These devices perform under a limited range of conditions with a limited variety of medicaments. There exist other methods of aerosolization, such as vaporization, that can accommodate a greater variety of medicaments and formulations, which these devices cannot provide. Furthermore, these devices do not provide nasal aerosol delivery. Moreover, these devices are not self-actuating, and therefore, may be difficult to time the coordination of dispensing medicament with patient inhalation.

There are numerous limitations inherent in prior aerosol delivery devices, including not being able to provide the optimal amount of airflow regulation under all conditions of aerosol delivery. Unlike the present disclosure, prior aerosol delivery devices do not accomplish all of the following:

A) greater control over laminar flow and/or flow velocity and volume of aerosolized air for improved aerosol delivery to patient or user airways;

B) greater and longer expansion of patient or user airways, such as with positive pressure, so that airways are more receptive to receiving aerosolized medicament formulations;

C) selective targeting of aerosols to different regions of the airways, such as the upper airways, lower airways, and/or providing systemic delivery through the pulmonary route;

D) accommodation of the full range of varying degrees of patient or user lung function and/or inspiratory ability, including, but not limited to, pediatric patients with small lung volumes, chronic obstructive pulmonary disease, COPD, patients with compromised lung function, and adult patients with healthy lung function;

E) accommodation of more medicament formulations that have potential for aerosolization; including liquids, suspensions and solids, droplets and particles, of varying sizes, shapes, weights, viscosities, and flow dynamic properties.

Therefore, prior aerosol delivery devices do not provide for enhanced efficiency of aerosol delivery under a wide range of medicament formulations, to a wide variety of users and patients, and to various regions of the airways, as embodiments of the present disclosure do. Embodiments of the present disclosure, therefore, have the ability to improve patient treatments for a multitude of ailments and diseases. Embodiments of the present disclosure also have the ability to speed drug product delivery research and development, R&D, time, and may reduce costs associated with R&D.

Nebulizers are medical devices that generate aerosol from a liquid using compressed gas or piezoelectric energy. Jet nebulizers pull liquid from a liquid reservoir and force the liquid, using compressed gas from a tank or air compressor, through a small restricted opening of a jet nozzle cover which causes nebulization. Ultrasonic nebulizers utilize a piezoelectric motor or piezo-oscillating element. Passing liquid through an aperture mesh or membrane that vibrates at ultrasonic frequencies causes nebulization. All nebulizers typically consist of a housing containing a liquid reservoir and a nebulization chamber with a nebulization generating means, e.g., jet nozzle or vibratable mesh, and an aerosol outlet port for receiving a mask or a mouthpiece, either directly or with a T-piece adapter. Some nebulizers are breath-enhanced and may contain ambient air inlets to more efficiently entrain and remove aerosol.

Nebulizers are drug delivery devices when they deliver aerosolized medications to a patient via a mouthpiece, nosepiece, or mask. Nebulizers are primarily used for delivering aerosolized medication, including bronchodilators, for relieving symptoms associated with asthma and chronic obstructive lung disease, COPD. Such asthma and COPD patients often have compromised lung function and trouble breathing. Jet nebulizers are primarily used in the hospital setting for treating these patients. A major drawback to most jet nebulizers, including those requiring a T-piece adapter, is that aerosol is wasted during patient exhalation and aerosol released in the hospital or emergency room can lead to occupational exposure. A large spacer device may be fitted to a nebulizer to help reduce occupational exposure. But a spacer can make delivery inefficient by reducing the concentration of the nebulized bolus, and the spacer does not entrain aerosol from within the nebulizer. A nebulizer can sometimes be fitted with an exhalation filter, which reduces occupational exposure, but does not prevent aerosol waste.

To reduce occupational exposure and aerosol waste during exhalation, a new class of jet nebulizers were developed that coordinated the generation of nebulized aerosols with the breathing cycle. The premise was that nebulization occurred only during inhalation, and not during exhalation. Such nebulizers formed a class known as breath-actuated jet nebulizers. Because these breath-actuated jet nebulizers were primarily intended for treating asthmatics and COPD patients of compromised lung function, and including pediatric patients and those utilizing a mask, they were purposely invented to have a very low triggering point so that normal breathing with no additional inhalation effort is required to actuate nebulization. Otherwise, actuation would be difficult or unattainable by these patients. These breath-actuated jet nebulizers have an actuator having biasing means with a predetermined spring or elastic force that is exceedingly weak. Thus, these prior art breath-actuated jet nebulizers have a very low, constant, single, threshold level of actuation. This threshold level of actuation is so low that, from the patient's perspective, may be considered negligible or insignificant if not associated with an increased inhalation effort that can be experienced. These breath-actuated jet nebulizers lack structures, mechanisms, and dialable interface components that would enable a patient user to increase the threshold level of actuation beyond a minimum baseline level. When and if actuation can be bypassed, there would be no threshold of actuation; breath coordinated actuation does not take place in a continuous nebulization mode.

By way of example, United States Patent Application Number 2007/0023036 to Grychowski et al., describes a breath-actuated nebulizer having a moveable gas diverter located at a variable height above the j et nozzle, which changes a deflection angle of gas emitted from the top of the gas nozzle across the liquid outlet. The gas diverter moves from a nebulizing position to a non-nebulizing position in response to a patient's breathing. Grychowski et al. teaches that a membrane provides an elastic triggering threshold that permits cyclical nebulization to occur that coincides with the breathing of the patient. This threshold is set to fall within normal human breathing parameters so that the diverter moves into and out of proximity with the nozzle top as a result of the patient's normal breathing. This level may be approximately less than or equal to 3.0 cm of water. There are no different negative pressure threshold settings of actuation and no dialable means of changing actuation of the device.

By way of another example, U.S. Pat. No. 7,131,439 to Blacker et al. describes a breath-actuated nebulizer having a nozzle cover that moves in response to a patient's breathing. This nozzle cover is associated with an actuator piston that responds to a negative pressure in the range of 0.5 to 1.0 cm of water because Blacker et al. teaches that it is desirable that a nebulizer have adequate sensitivity to quickly respond to an inhalation while not adversely restricting the patient's inhalation. Blacker et al. also teaches a relief piston separately mounted and independently movable with respect to the actuator piston may be used to alleviate inhalation effort after an initial period of inhalation. The relief piston is preferably configured to increase the amount of additional ambient air provided to the chamber as the patient's inhalation increases to keep the negative pressure from rising to a point that makes inhalation difficult for the patient. As such, the relief piston opens to prevent negative pressure from increasing above 1.0 cm of water. The relief piston also has the effect of reducing the resistance to inhalation. Actuation and movement of the actuator piston can be bypassed with a continuous nebulization selection lever, and when in this continuous operation mode, there is no threshold of actuation for nebulization to take place. There are no different negative pressure threshold settings of actuation. Actuation of the actuator piston can only be turned on or turned off, and the negative pressure of the device remains the same; negative pressure is sustained at the same 1.0 cm of water either way.

While these breath-actuated nebulizers serve their intended purpose, they, like regular jet nebulizers, are deficient in being able to increase negative pressure to a different level and do not have increased negative pressure threshold settings of actuation. It can be appreciated that in certain circumstances, increased negative pressure thresholds and increased inhalation effort can be desirable, and in this sense, the present disclosure departs from the usual doctrines of effortless asthma and COPD aerosol treatments. For instance, higher negative pressure thresholds, thresholds above 3.0 cm of water, require an increased inhalation effort with greater exertion of the muscles involved in respiration. These higher negative pressure thresholds, as experienced by the patient, can exercise the respiratory muscles beyond what normal breathing can do. Such higher negative pressure thresholds can be used for strength training of the muscles involved in respiration, but can also be used to help maintain lung elasticity and improve respiratory health. Only a nebulizer of the present disclosure having these different negative pressure threshold settings could be used by chest surgery patients, instead of an incentive spirometer, to help remove secretions and prevent atelectasis on the day of their operation. Embodiments of the present disclosure may also serve as incentive devices because movement of the negative pressure threshold valve assembly from inhalation may provide a visual signal, and perhaps an auditory signal, to the user. Such a stand-alone nebulizer device has the potential to reduce overall hospital costs, while saving time and providing greater convenience. The prior art nebulizers of Grychowski et al. and Blacker et al. are not capable of providing negative pressure threshold resistance training because they have a negative pressure threshold that is exceedingly low and does not require an increased inhalation effort from the patient. Their nebulizers also cannot make inhalation more difficult than normal breathing, and therefore, lack the therapeutic benefits associated with an increased negative pressure threshold.

For patients with adequate lung function that can achieve greater inhalation effort, the different negative pressure threshold settings of this novel nebulizer can have profound effects on aerosol delivery dynamics. More specifically, by having actuation of nebulization and aerosol entrainment associated with different negative pressure threshold settings, the nebulizer can be used to selectively target aerosols to one or more different airway regions. In effect, aerosol actuation, entrainment, and delivery occur when one or more different airways are optimally expanded with the desired pressure for enhanced drug targeting and delivery efficiency.

More pharmaceuticals are being made available for inhalation. This includes pharmaceuticals that can be delivered to the systemic circulation via the pulmonary route. As an improved drug delivery device, embodiments of the present disclosure can improve the delivery dynamics and targeting of these drugs. Selective targeting of aerosols to one or more different airway regions can aid in the targeting of aerosolized chemotherapies against lung cancer. Selective targeting of aerosols to one or more different airway regions can also have profound military medicine applications, including biodefense to counter bioterrorism, by coating upper airways with antibiotics against anthrax or other infectious agents, or by providing anticholinergic agents to the systemic circulation via alveoli as an antidote to nerve agent exposure. Embodiments of the present disclosure also have the potential to enhance the deliverability of drug candidates in development, which has the potential to reduce drug development costs.

In this respect, the aerosol delivery device according to the present disclosure substantially departs from the conventional concepts and designs of the prior art, and in doing so provides an apparatus primarily developed for the purpose of providing controlled airflow through the device to optimize aerosol delivery under a greater range of conditions.

Therefore, it can be appreciated that there exists a continuing need for a new and improved aerosol delivery device which can be used for providing controlled airflow through the device to optimize aerosol delivery under a greater range of conditions. In this regard, embodiments of the present disclosure substantially fulfill this need. Additionally, there is a need for an improved nebulizer that can overcome one or more of the limitations discussed above, and open the way for new and improved methods of providing nebulization treatments.

SUMMARY OF THE DISCLOSURE

In view of the foregoing disadvantages inherent in the known types of aerosol delivery devices of known designs and configurations, the present disclosure provides an improved aerosol delivery device. As such, the general purpose of the present disclosure, which will be described subsequently in greater detail, is to provide a new and improved aerosol delivery device and method which has all the advantages of prior devices and none of the disadvantages.

To attain this, an embodiment of the present disclosure essentially comprises a housing with at least one airflow inlet, at least one airflow outlet, and at least one airflow passage extending there between. A medicinal, therapeutic, or other aerosolizable substance to be inhaled is provided. Within this housing is at least one site/element for producing and/or dispensing an aerosol to be entrained by airflow through the device. At least one calibrated airflow resistance control element with adjustable settings allows regulation of airflow into, through, and/or out of an embodiment of the present disclosure.

The present disclosure describes an aerosol delivery device having a structure comprising a housing, an at least one (ambient) air inlet, an at least one aerosolized air outlet, and an at least one airflow passage (extending) there between/therein. The aerosol delivery device further comprises an at least one aerosol generating element producing an aerosol from an at least one aerosolizable substance or formulation with the use of electrical energy and without the use of compressed/pressurized gas. The aerosol delivery device further has an at least one airflow through its housing produced by a user inhaling from this aerosol delivery device and entraining aerosol when generated. In some embodiments, the at least one airflow is controllable in velocity, volume, or a combination thereof as the at least one air inlet, the at least one aerosolized air outlet, the at least one airflow passage, or a combination thereof undergoes an at least one physical change selected from changes in size, angle, shape, (biasing) resistance to flow, number of apertures, or a combination thereof. The at least one physical change is modulated by user/digital input to control the at least one airflow and or entrained aerosolized air and to regulate an at least one parameter selected from user inhalation resistance, user inhalation duration, user inhalation rate, aerosol delivery efficiency, targeting of aerosol to different user airway regions, or a combination thereof. In different embodiments, the aerosol delivery device has an adjustable airflow restriction of the at least one airflow through the housing, and or an adjustable negative pressure through the housing, experienced when the user inhales through the aerosol delivery device. The user can modulate the at least one physical change of the device by the act of inhaling itself when the device adjusts automatically in a non-electric analog manner, such as with valves; or automatically via sensors, circuitry, and motors. Or, the user can modulate the at least one physical change of the device by manually moving a dial, lever, or setting with the user's fingers or hand. Or, the user can modulate the at least one physical change of the device via a digital control unit by pressing a button or dial, or by voice activation, or via software programming or algorithms, or via a Smartphone or other electronic device.

There has thus been outlined, rather broadly, the more important features of embodiments of the present disclosure in order that the detailed description thereof that follows may be better understood and in order that the present contribution to the art may be better appreciated. There are, of course, additional features of embodiments of the present disclosure that will be described hereinafter and which will form the subject matter of the claims attached.

In this respect, before explaining at least one embodiment of the disclosure in detail, it is to be understood that the disclosure is not limited in its application to the details of construction and to the arrangements of the components set forth in the following description or illustrated in the drawings. Embodiments of the present disclosure are capable of other examples and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of embodiments of the present disclosure. It is important, therefore, that the claims be regarded as including such equivalent constructions insofar as they do not depart from the spirit and scope of the present disclosure.

It is therefore an object of the present disclosure to provide a new and improved aerosol delivery device which has all of the advantages of the prior art aerosol delivery devices of known designs and configurations and none of the disadvantages.

It is another object of the present disclosure to provide a new and improved aerosol delivery device which may be easily and efficiently manufactured and marketed.

It is further object of the present disclosure to provide a new and improved aerosol delivery device which is of durable and reliable constructions.

An even further object of the present disclosure is to provide a new and improved aerosol delivery device which is susceptible of a low cost of manufacture with regard to both materials and labor, and which accordingly is then susceptible of low prices of sale to the consuming public, thereby making such aerosol delivery device economically available to the buying public.

Even still another object of the present disclosure is to provide an aerosol delivery device for providing controlled airflow through the device to optimize aerosol delivery under a greater range of conditions.

Lastly, it is an object of the present disclosure to provide a new and improved aerosol delivery device comprising a housing with at least one airflow inlet, at least one airflow outlet, and at least one airflow passage extending there between. A medicinal or therapeutic substance to be inhaled is provided. Within this housing is at least one site/element for producing and/or dispensing an aerosol to be entrained by airflow through the device. At least one calibrated airflow resistance control element with adjustable settings allows regulation of airflow into, through, and/or out of embodiments of the present disclosure.

Therefore, various exemplary embodiments of the disclosure may provide an improved nebulizer having different negative pressure thresholds. The embodiments of this novel nebulizer generally include an adjustable negative pressure threshold valve that actuates in response to different negative pressures corresponding to different negative pressure threshold settings of actuation. Such a nebulizer is only embodied and described by the present disclosure. The negative pressure threshold valve generally includes a biasing member component having a variable biasing member force. More specifically, the negative pressure threshold valve of preferred embodiments includes a dialable component with settings that change the pressure thresholds of actuation, by changing the biasing member force of the biasing member. These embodiments enable the patient user to increase the negative pressure threshold required for actuation to take place so that actuation of the valve is associated with an increased inhalation effort experienced by the patient.

To attain the advantages and in accordance with the purpose of embodiments of the present disclosure, as embodied and broadly described herein, one exemplary aspect of an embodiment of the present disclosure provides a novel jet nebulizer that includes a dialable negative pressure threshold valve whereby actuation of this valve, at any of the different negative pressure threshold settings, is associated with allowing ambient air to enter through the nebulizer, preferably by the valve including at least one ambient air inlet of the nebulizer, so that aerosol can be entrained from within the nebulizer.

Accordingly, this first exemplary nebulizer embodiment is adapted to nebulize/atomize liquid substance/solution for inhalation using compressed/pressurized gas, and comprises: a liquid reservoir container defining an inner space adapted to receive a liquid therein, a non-moveable jet nozzle provided through at least some of the inner space for passage of a pressurized gas entering from a gas inlet and exiting through a tapered air outlet at the jet nozzle tip, a non-moveable jacket circumferentially sleeved around the jet nozzle to define a constant fluid-introducing gap there between, the fluid-introducing gap being in fluid communication with the inner space for passage of the liquid there through, the jacket having at least one restricted opening at its tip which emits the jet, a mist-discharging conduit extending into the nebulization chamber and in fluid communication with the inner space for passage of a mist there through and aligned with the jacket in a jet-ejecting direction, an impact baffle positioned in the path of the jet to disperse nebulized particles generated as high-pressure gas atomizes the liquid leaving the restricted opening of the jacket tip, at least one aperture for the mist-discharging conduit to receive ambient air, and an aerosol air outlet port for delivering aerosol to the airways of a patient.

The nebulizer further includes an adjustable negative pressure threshold valve operatively coupled to a nebulization chamber. The chamber and its mist-discharging conduit or chimney are adapted to receive both nebulized aerosol particles and ambient air.

The adjustable negative pressure threshold valve has a plurality of settings of actuation. The nebulizer further includes a reciprocable component operatively coupled to the adjustable negative pressure threshold valve, the reciprocable component is adapted to adjust the settings of actuation of the adjustable negative pressure threshold valve. The reciprocable component is comprised of a rotatable cap with an integrally formed cylindrical wall slidably received through a preferably cylindrical upper region of the device housing. The rotatable cap includes one set of ambient air inlets at the top base of the cap.

The rotatable cap further includes a tubular guide extending through a portion of it, the tubular guide includes female threads designed to receive the male threads of a thin rod comprising a component of the valve so that the reciprocal component is operatively coupled to the valve. The threaded thin rod further includes a circular disc fixedly attached to the bottom of the rod, the circular disc and rod comprises an actuator piston of the threshold valve. The circular disc is located within the interior chamber of the device, and preferably within a chimney region of the device having a Venturi-like central aperture between the disc and the rotatable cap.

A load calibrated, coiled spring biasing member further comprises the valve and is positioned inside of the rotatable cap around the tubular guide and thin rod. The spring biasing member puts upward pressure on the rotatable cap so that the circular disc is pulled against the top surface of the inner chamber chimney to block the central aperture and prevent ambient air from entering the central aperture before actuation of the valve takes place.

The spring has an adjustable biasing member force that is modulated by rotation of the cap so that the distance that the thin rod screws into the tubular guide of the cap changes, thereby affecting the space between the cap and the central aperture of the chimney, and thereby changing the compression and tension of the spring and changing the negative pressure threshold required for actuation of the valve. In this manner, the reciprocable component is adapted to adjust the settings of actuation of the adjustable negative pressure threshold valve by changing the biasing member force of the biasing member component.

The adjustable negative pressure threshold valve is adapted to actuate in response to different negative pressures corresponding to different negative pressure threshold settings of actuation. The valve actuates when a sufficient negative pressure is generated by patient inhalation to surpass the biasing member force of the spring, so that the actuator piston moves downward. Downward movement of the actuator piston allows ambient air to enter the central aperture of the device; ambient air coming from the ambient air inlet of the reciprocable component of the valve. The reciprocable component and the valve are adapted to influence nebulized aerosol delivery by allowing ambient air to enter the nebulization chamber and entrain aerosol particles.

Actuation of the valve ceases when negative pressure generated by the patient decreases below the negative pressure threshold of the valve, and the actuator piston and valve returns to its resting position.

To attain the other advantages and in accordance with the purpose of the embodiments of the present disclosure, as embodied and broadly described herein, another exemplary aspect of an embodiment of the present disclosure provides a novel jet nebulizer that includes a dialable negative pressure threshold valve whereby actuation of this valve, at any of the different negative pressure threshold settings, is also associated with actuation of nebulization so that nebulization is coordinated with the patient's breathing cycle. To achieve non-continuous, breath activated nebulization that is coordinated with the patient's breathing cycle, the nebulizer according to an exemplary embodiment of the disclosure is further adapted and modified.

Accordingly, this modified first exemplary nebulizer embodiment is adapted to nebulize/atomize a liquid substance/solution for inhalation using compressed/pressurized gas, and comprises: a liquid reservoir container defining an inner space adapted to receive a liquid therein, a non-moveable jet nozzle provided through at least some of the inner space for passage of a pressurized gas entering from a gas inlet and exiting through a tapered air outlet at the jet nozzle tip, a non-moveable jacket circumferentially sieved around the jet nozzle to define a constant fluid-introducing gap there between, the fluid-introducing gap being in fluid communication with the inner space for passage of the liquid there through, the jacket having at least one restricted opening at its tip which emits the jet, a mist-discharging conduit extending into the nebulization chamber and in fluid communication with the inner space for passage of a mist there through and aligned with the jacket in a jet-ejecting direction, an impact baffle positioned in the path of the jet to disperse nebulized particles generated as high-pressure gas atomizes the liquid leaving the restricted opening of the jacket tip, at least one aperture for the mist-discharging conduit to receive ambient air, and an aerosol air outlet port for delivering aerosol to the airways of a patient.

The jacket further includes the modification of at most two small holes at its tip, adjacent to the restricted opening. When the at most two small jacket holes are unobstructed, nebulization does not take place so that aerosol is not generated from the jacket restricted opening.

The nebulizer further includes an adjustable negative pressure threshold valve operatively coupled to a nebulization chamber. The chamber and its mist-discharging conduit or chimney are adapted to receive both nebulized aerosol particles and ambient air.

The adjustable negative pressure threshold valve has a plurality of settings of actuation. The nebulizer further includes a reciprocable component operatively coupled to the adjustable negative pressure threshold valve, the reciprocable component is adapted to adjust the settings of actuation of the adjustable negative pressure threshold valve. The reciprocable component is comprised of a rotatable cap with an integrally formed cylindrical wall slidably received through a preferably cylindrical upper region of the device housing. The rotatable cap includes one set of ambient air inlets at the top base of the cap.

The rotatable cap further includes a tubular guide extending through a portion of it, the tubular guide includes female threads designed to receive the male threads of a thin rod comprising a component of the valve so that the reciprocal component is operatively coupled to the valve. The threaded thin rod further includes a circular disc fixedly attached to the bottom of the rod, the circular disc and rod comprises an actuator piston of the threshold valve. The circular disc is located within the interior chamber of the device, and preferably within a chimney region of the device having a Venturi-like central aperture between the disc and the rotatable cap.

The nebulizer further includes the modification of a moveable seal associated with the actuator piston. The moveable seal is preferably horseshoe-shaped and is not a component of the nozzle jacket. The moveable seal is attached under the circular disc, and preferably attached to the end of thin rod, a portion of the rod which extends past the circular disc.

A load calibrated, coiled spring biasing member further comprises the valve and is positioned inside of the rotatable cap around the tubular guide and thin rod. The spring biasing member puts upward pressure on the rotatable cap so that the circular disc is pulled against the top surface of the inner chamber chimney to block the central aperture and prevent ambient air from entering the central aperture before actuation of the valve takes place.

The spring has an adjustable biasing member force that is modulated by rotation of the cap so that the distance that the thin rod screws into the tubular guide of the cap changes, thereby affecting the space between the cap and the central aperture of the chimney, and thereby changing the compression and tension of the spring and changing the negative pressure threshold required for actuation of the valve. In this manner, the reciprocable component is adapted to adjust the settings of actuation of the adjustable negative pressure threshold valve by changing the biasing member force of the biasing member component.

The adjustable negative pressure threshold valve is adapted to actuate in response to different negative pressures corresponding to different negative pressure threshold settings of actuation. The valve actuates when a sufficient negative pressure is generated by patient inhalation to surpass the biasing member force of the spring, so that the actuator piston moves downward. Downward movement of the actuator piston allows ambient air to enter the central aperture of the device; ambient air coming from the ambient air inlet of the reciprocable component of the valve. Downward movement of the actuator piston during actuation also moves the moveable seal downward to flank and obstruct the at most two small holes at the tip of the nozzle jacket, adjacent to the restricted opening, so that nebulization takes place while sufficient negative pressure is generated during inhalation. The reciprocable component and the valve are adapted to influence nebulized aerosol delivery by allowing ambient air to enter the nebulization chamber and entrain aerosol particles when nebulization is actuated.

Actuation of the valve ceases when the negative pressure generated by the patient decreases below the negative pressure threshold of the valve. As inhalation ends, the actuator piston of the valve and its associated moveable seal return to their resting position, so that the at most two small jacket holes are unobstructed again and nebulization stops. Nebulization is therefore coordinated with the patient's breathing cycle.

The mechanism of breath activation of the present disclosure is much different from Grychowski et al. and Blacker et al, which are more susceptible to variations in nebulized particle generation and aerosol particle mass median aerodynamic diameter, MMAD, attributed to minor differences in movement of nebulization components. Unlike Grychowski et al., there is no moveable gas diverter located above the jet nozzle, which changes a deflection angle of gas emitted from the top of the gas nozzle across the liquid outlet. Unlike Blacker et al., there is no moveable nozzle cover or moveable portion of a nozzle cover that can result in variability in a fluid introducing gap between the jet nozzle and nozzle cover, and disturb the liquid medicament layer. An embodiment of the present disclosure preferably has a jet nozzle, a nozzle cover, and an impact baffle that do not move and are always in a fixed position relative to each other. Therefore, when nebulization takes place, the aerosol particles generated by at least some embodiments of the present disclosure are always consistent in MMAD. Also unlike the prior art, ambient air cannot flow through the present device before actuation takes place. This permits the present invention to build up enough negative pressure to overcome the substantial resistance associated with the dialable negative pressure threshold valve. Only embodiments of the present disclosure have multiple settings with different negative pressure thresholds associated with each. The biasing member force of the at least some embodiments of the present disclosure are not predetermined as the prior art, and instead changes in accordance to these negative pressure threshold settings of actuation. Each different setting is consistent, sustained, and reproducible so that the dialable valve of at least some embodiments of the present disclosure serves as a calibrated negative pressure threshold control element.

These together with other objects of the disclosure, along with the various features of novelty which characterize embodiments of the present disclosure, are pointed out with particularity in the claims annexed to and forming a part of this disclosure. For a better understanding of the embodiments of the present disclosure, their operating advantages and the specific objects attained by their uses, reference should be had to the accompanying drawings and descriptive matter in which there is illustrated preferred embodiments of the disclosure.

Additional objects and advantages of embodiments of the present disclosure will be set forth in part in the description which follows, and in part will be obvious from the description, or may be learned by practice of embodiments of the present disclosure. The objects and advantages of the invention will be realized and attained by means of the elements and combinations particularly pointed out in the appended claims.

It is to be understood that both the foregoing general description and the following detailed description are exemplary and explanatory only and are not restrictive of embodiments of the present disclosure, as claimed.

BRIEF DESCRIPTION OF THE DRAWINGS

Embodiments of the present disclosure will be better understood and objects other than those set forth above will become apparent when consideration is given to the following detailed description thereof. Such description makes reference to the annexed drawings wherein:

FIG. 26 includes a cross-sectional back view of a nebulizer that includes a valve bypass lock pin and dial lock pin port, in accordance with an embodiment of the disclosure.

FIG. 27 includes a cross-sectional back view of the nebulizer of FIG. 26, in accordance with an embodiment of the disclosure.

FIG. 28 includes a cross-sectional side view of an aerosol delivery device, in accordance with an embodiment of the disclosure.

FIG. 32A includes a side view of an aerosol delivery device housing, in accordance with an embodiment of the disclosure.

FIG. 32B includes a side view of an alternate aerosol delivery device housing, in accordance with an embodiment of the disclosure.

The same reference numerals refer to the same parts throughout the various Figures.

DESCRIPTION OF THE PRESENTLY PREFERRED EMBODIMENTS

With reference now to the drawings, the preferred embodiments of the systems and methods of aerosol delivery with airflow regulation embodying the principles and concepts of the present disclosure will be described in the following aerosol delivery device embodiments.

Figure 1:
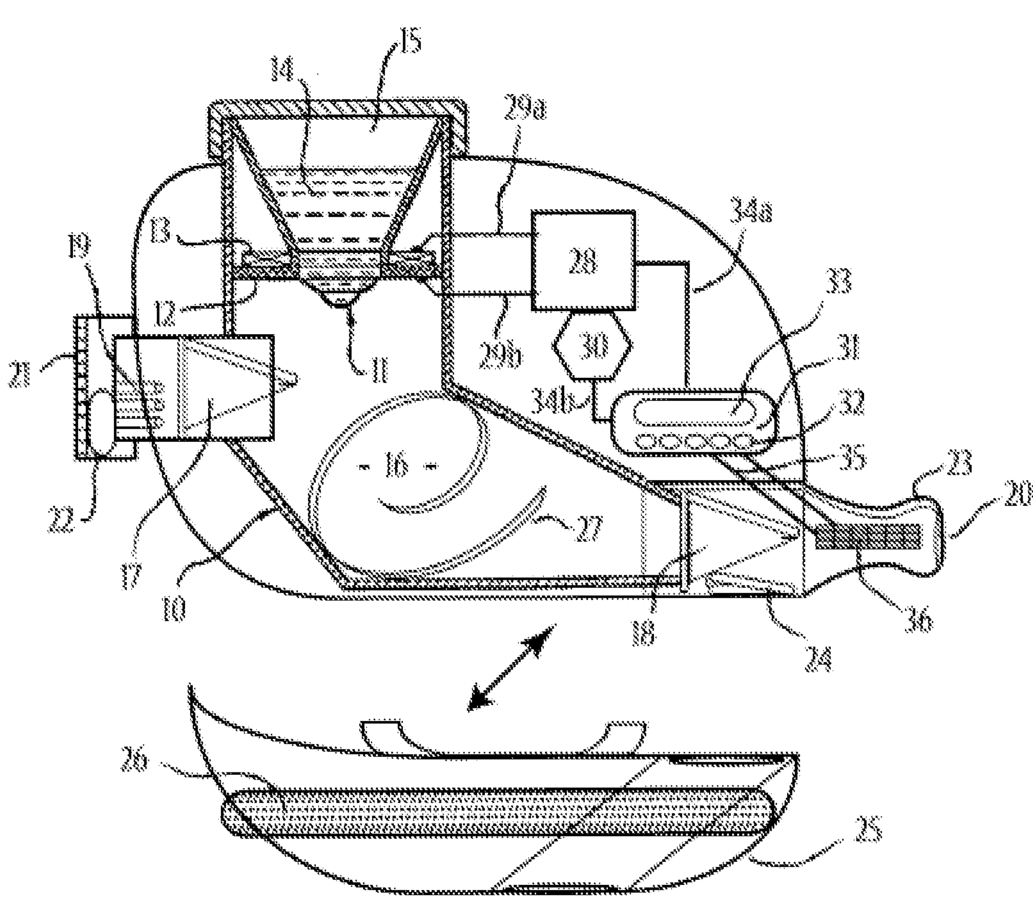
FIG. 1 includes a cross-sectional side view of an aerosol delivery device, in accordance with an embodiment of the disclosure.

FIG. 1 includes a cross-sectional side view of an aerosol delivery device 10, in accordance with an embodiment of the disclosure. The aerosol delivery device 10 may include a vibratable, porous membrane 11 that is caused to oscillate at a desired frequency by piezoelectric motor assembly (e.g., a support unit 12 and a piezo-electrical conversion unit 13) in response to an electric drive signal. The support unit 12 and the piezo-electrical conversion unit 13, both contain or comprise electrically conductive material. Both the support unit 12 and the piezo-electrical conversion unit 13 are attached to each other, and both are attached to vibratable membrane 11.

The oscillation of vibratable membrane 11, which may include bending oscillations, causes a liquid medicament formulation 14, stored within a liquid reservoir 15, to be nebulized as this liquid is forced through small pores of membrane 11. The resulting nebulized aerosol travels into, and diffuses within, the large reserve chamber, holding chamber, 16.

One-way valves 17 and 18, preferably duckbill valves, trap the nebulized aerosol within the device until vacuum pressure, or a significant threshold vacuum pressure, generated from user inhalation, is able to open said one-way valves 17 and 18. Nebulized aerosol is thusly contained in reserve chamber 16 until airflow, originating at one or more airflow inlets 19, carries the aerosol through the device and out to the end user through the airflow outlet end 20 of the aerosol delivery device 10.

Calibrated airflow resistance control element 21, in this embodiment, consists of a user controlled airflow resistance dial with one or more supplemental apertures 22. The user controlled airflow resistance dial 21 is flush with the airflow inlet end of the device. Rotation of dial 21 aligns supplemental aperture(s) 22 with one or more airflow inlet passages 19, thereby controlling the amount of airflow allowed to enter the device and travel through these passages 19, having the effect of controlling the velocity and/or volume of airflow through the aerosol delivery device 10. The airflow resistance settings of the aerosol delivery device 10 may also provide an auditory signal to the user, such as a whistle sound caused by air passing through the airflow control element.

Furthermore, the pitch of this whistle sound may vary between different airflow resistance settings and may allow the user to distinguish between such settings. Furthermore, the auditory signal may indicate for user to adjust his or her inhalation rate.

The airflow outlet end of the aerosol delivery device 10 may contain a mouthpiece 23 that contours to the user's lips, allowing for an airtight seal. Said mouthpiece 23 may contain an exhaust port 24 (including an elastomeric one-way, flap valve) that vents user exhalation, while one-way valve 18 prevents exhalation from entering the interior of the device. An optional and/or removable filter housing assembly 25 may be aligned with exhaust port 24 to allow exhaled air to pass through a filter element 26, and out of the filter housing 25. A preferred filter element 26 may be a 3M® filtrate filter, or other HEPA filter, able to capture infectious particles and aerosol particles larger than 0.3 micrometers in diameter from exhalation, thereby preventing cross contamination to nearby individuals. A contaminated filter element may be cleaned or replaced, as necessary.

The interior walls of the aerosol delivery device 10, such as along reserve chamber 16, may be curved and/or contain spiral baffles 27 to generate a rotational flow of aerosolized air that enters the device. Said rotational airflow may surround the aerosol and may more efficiently carry the aerosol out of the aerosol delivery device 10, while reducing impaction or adhesion of aerosol with the inner walls of the aerosol delivery device 10.

The aerosol delivery device 10 also includes an electronic drive means 28 that sends an electric drive signal through signal lines 29*a* and 29*b* to the piezo-electrical conversion unit 13 and the support unit 12 of the piezoelectric motor assembly. A power source 30, preferably a rechargeable battery with an inlet for alternating current, provides the electrical energy for the electronic drive means 28. The aerosol delivery device 10 may further includes a digital control unit 31, with user inputs 32, and a digital display 33, such as LCD or LED, and/or electroacoustic transducer speaker, not shown. The digital control unit 31 operates the electronic drive means 28 through circuit lines 34*a* and 34*b*. The digital control unit 31 may also contain a microprocessor that can perform one or more functions, such as: setting the intensity of the electric drive signal, providing visual and/or auditory feedback to the user and/or health care worker, providing an alarm function to signal when a treatment is due, a timer function to measure the duration of treatment and/or to turn off operation after a certain treatment duration, a counting function to determine the number of treatments, a function to keep track of the airflow resistance settings during treatment, a time/date function to track the treatments of one or more different medicament formulations, along with any other functions obvious to the use of this device. Furthermore, the digital control unit 31 may contain a USB port and/or memory card so that data can be interfaced with a computer or respiratory instrument.

The aerosol delivery device 10 may also contain one or more sensing leads or panels (touch panels) 36, as an integral component of the mouthpiece 23, that form a switching circuit with the digital control unit 31 via circuit leads 35. In one example, the touch panels 36 may include conductivity sensing touch panels. Conductivity sensing touch panels 36 receive bioelectricity through a living being in contact with the touch panel to complete this switching circuit, which may signal the digital control unit 31 to activate electronic drive means 28 so that the aerosol delivery device 10 may generate or dispense aerosol only when the user is able to receive such aerosol delivery. Said conductivity sensing touch panels 36 may, therefore, prevent aerosol loss when the user is not able to receive aerosol. The switching circuit may include one or more resistors, transistors, grounds, capacitors, and/or any other circuit components necessary for the function of this circuit. In another example, the touch panels 36 may include pressure sensing touch panels that detect user contact with the device. Alternatively, airflow sensors could be used in place of, or in addition to, touch panels 36. Likewise, airflow sensors would detect and/or monitor user inhalation and provide such information to the digital control unit 31 that can interpret the data so as to activate and/or regulate aerosol generation via electronic drive means 28, and/or to provide visual and/or auditory feedback to the user and/or health care worker.

In an alternative embodiment of the disclosure, airflow sensors may also provide feedback of airflow and/or breathing pattern data to a digital control unit 31, or microprocessor, which can interpret the data and can adjust airflow resistance by sending an electronic signal to an electric motor controlling a calibrated airflow resistance control element, such as that described in the next figure.

In other embodiments, the piezoelectric motor assembly may also serve as, or include, or be accompanied by, or be replaced by, a heat generating means to raise the temperature of the air and/or aerosolized liquid droplets within the device to promote reduced particle size and convection. Electrical resistance preferably provides the heat energy for the heat generating means, and so the heat generating element is foremost an electrically resistive heating element. Furthermore, this heat generating element may serve as a vaporizing element to vaporize a liquid into a condensation aerosol available for inhalation, and may be used with, or instead of, ultrasonic nebulization.

Figure 2:
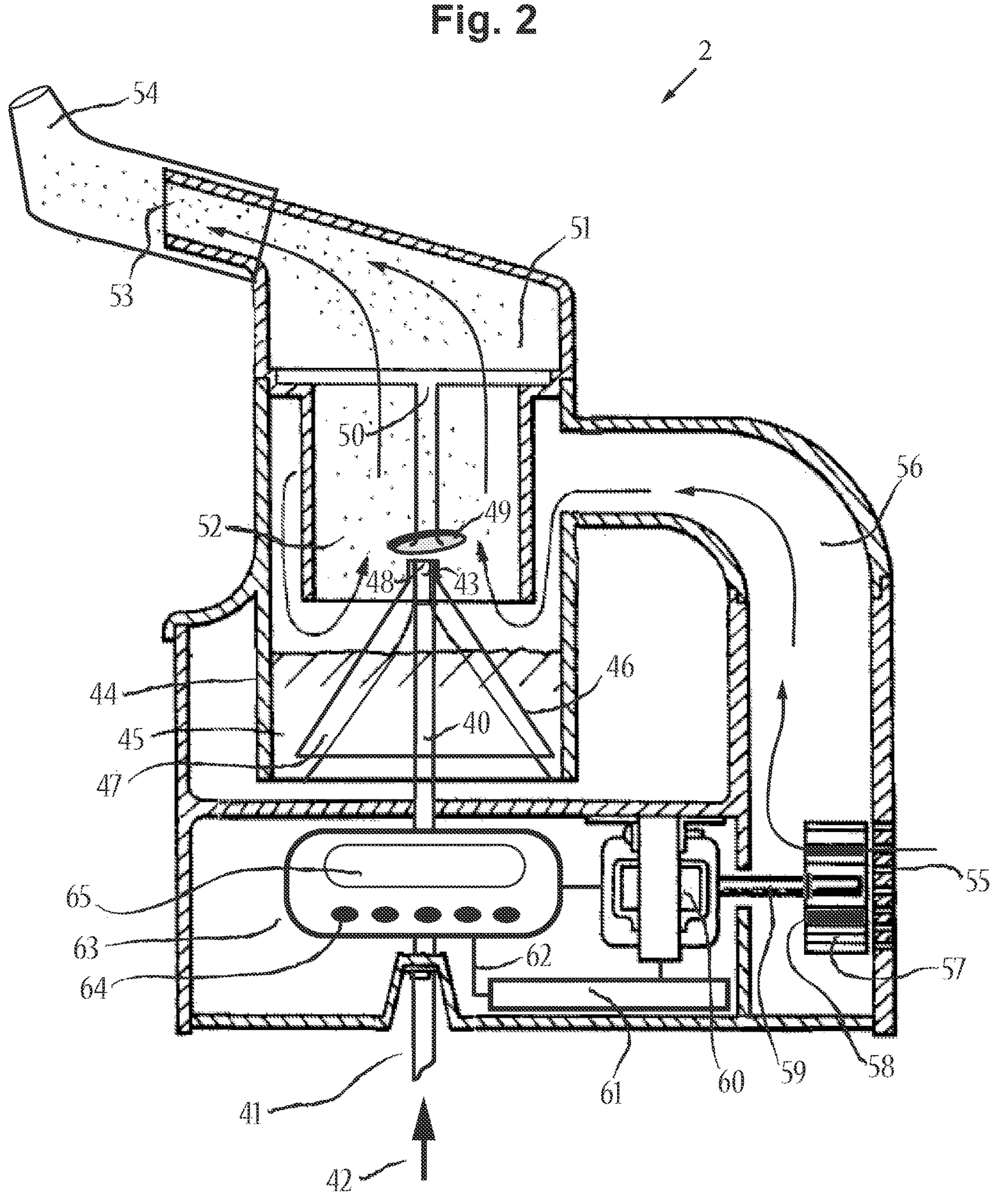
FIG. 2 includes a cross-sectional side view of an aerosol delivery device that includes a jet nebulizer device, in accordance with an embodiment of the disclosure.

FIG. 2 includes a cross-sectional side view of an aerosol delivery device that includes a jet nebulizer device 2, in accordance with an embodiment of the disclosure. The jet nebulizer device 2 includes a jet nozzle 40 that is able to receive compressed air and/or compressed oxygen from compressed gas inlet 41 connected to a source of compressed gas 42. Sources of compressed gas may include air pumps, portable air compressors, oxygen concentrators, or pressurized medical gas tanks. The source of compressed gas 42 may even be a component of the aerosol delivery device itself, such as if the source of compressed gas is a miniature, battery powered, air compressor. Jet nozzle 40 includes a tapered air outlet 43. The jet nozzle 40 resides inside of a liquid reservoir container 44, filled with a liquid medicament formulation 45. A jacket 46 is sleeved around the jet nozzle to define a fluid-introducing gap 47 there between. At the top of the jacket is a restricted opening 48. When in use, a high-pressure air jet passes through jet nozzle 40 and out through the tapered air outlet 43, causing liquid 45 to flow into the fluid-introducing gap 47 due to negative pressure generated therein. Liquid becomes nebulized into aerosol as high-pressure forces this liquid through the restricted opening 48 of jacket 46. Newly generated aerosol is dispersed as it comes in contact with a diffuser dispersing baffle 49 at high velocity. Baffle 49 is suspended by support 50. Support 50 has apertures or vents to allow aerosol to pass. Support 50 is housed by cap 51, which is connected detachably and securely to reservoir container 44. Container cap 51 also has a mist-discharging conduit or duct 52, and an aerosol outlet end 53. In this embodiment, a nosepiece 54 is incorporated with the device, instead of a mouthpiece, so as to provide nasal aerosol delivery to the upper airways. The mist-discharging conduit 52 and/or container cap 51 may be enlarged to serve as a reserve chamber for aerosol.

This jet nebulizer device 2 of FIG. 2 also contains one or more air inlet apertures 55 from which ambient air can enter into the device. Aerosol is carried out of the device with the assistance of airflow, depicted as arrows, which originates via inlet 55, and travels through duct 56 and into container 44, and out the aerosol outlet end 53 of container cap 51, via conduit 52, when a patient applies vacuum pressure from inhalation. The airflow that enters the device can be restricted, such as with a calibrated airflow resistance control element 57, so as to control the velocity and/or volume of airflow and/or aerosolized air through the device and out to the end user. In this embodiment, a calibrated airflow resistance control element (e.g., wheel or rotatable wheel) 57 consists of a rotatable wheel that is flush against the wall of the device in the area where inlet apertures 55 reside. The rotatable wheel 57 has a plurality of airway passages 58 which can differentially align with airway inlet(s) 55. Airflow and velocity through the device is increased when more of these airway passages 58 align with airway inlet(s) 55, and airflow and velocity through the device is decreased when less of these airway passages 58 align with airway inlet(s) 55. Axel 59 connects the rotatable wheel 57 to an electric motor 60, which uses electrical energy supplied by power source 61 to produce the mechanical energy to turn the rotatable wheel 57. A circuit 62 containing an analog or digital control unit 63, with user inputs 64, and an LCD or LED display 65 and/or electroacoustic transducer, speaker, not shown, and can operate the electric motor 60, such as to rotate the wheel 57 to the desired calibrated resistance setting, from a selection of such settings. The control unit 63 may also contain a microprocessor that can perform one or more functions, such as: providing visual and/or auditory feedback to the user and/or health care worker, providing an alarm function to signal when a treatment is due, a timer function to measure the duration of treatment and/or to signal after a certain treatment duration is complete, a counting function to determine the number of treatments, a function to keep track of the airflow resistance settings during treatment, a time/date function to track the treatments of one or more different medicament formulations, along with any other functions obvious to the use of this device. Furthermore, the control unit 63 may contain a USB port and/or memory card so that data can be interfaced with a computer or respiratory instrument.

Figures 3A, 3B:
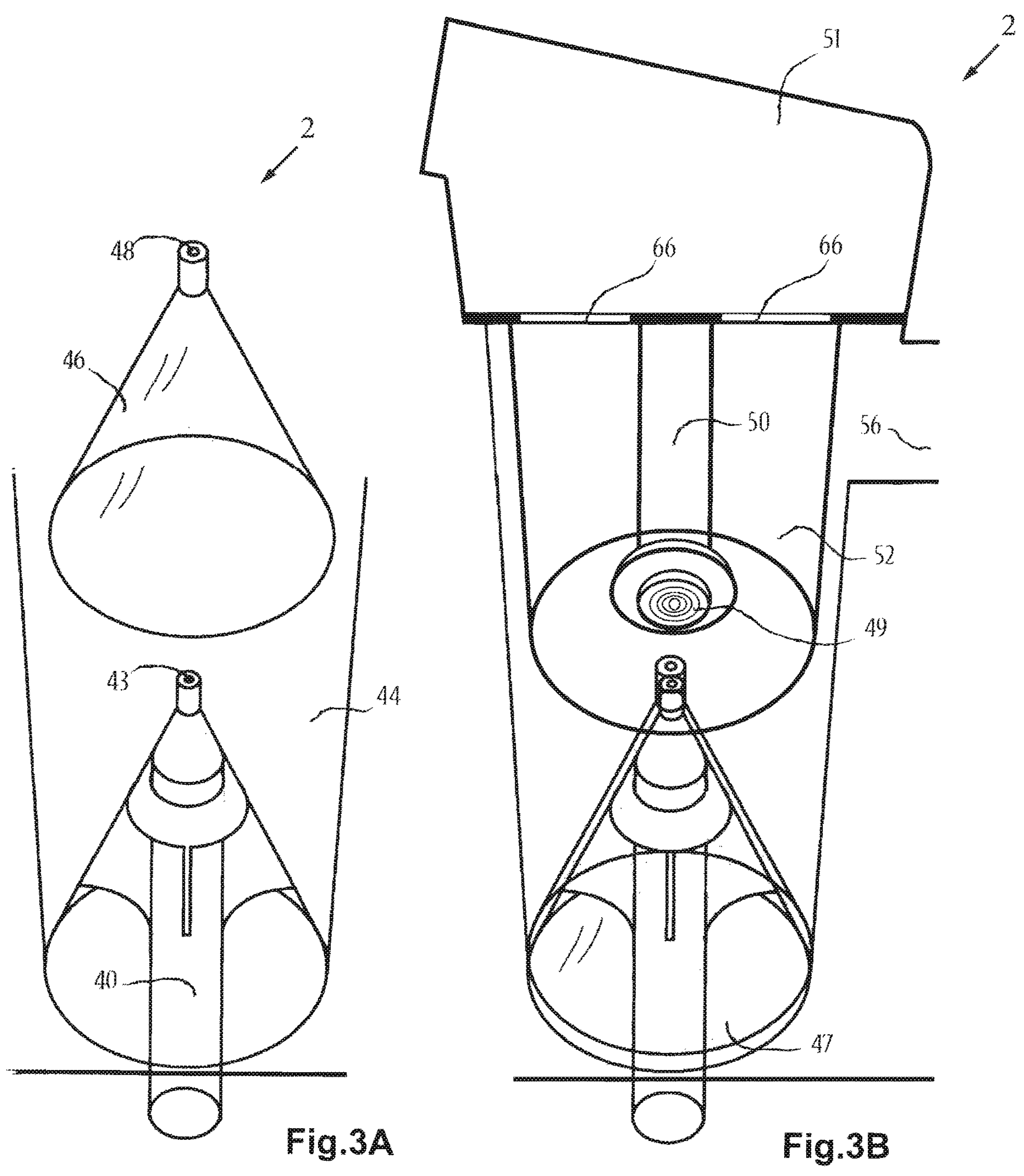
FIGS. 3A and 3B include additional views of portions of the jet nebulizer device of FIG. 2, in accordance with an embodiment of the disclosure.

FIGS. 3A and 3B include additional views of portions of the jet nebulizer device 2 of FIG. 2, in accordance with an embodiment of the disclosure. FIGS. 3A and 3B show the jet nozzle 40 and the reservoir container 44 of the jet nebulizer device 2 of FIG. 2. FIG. 3A is an exploded view of jet nozzle 40, housed inside of the reservoir container 44, along with jacket 46. Jet nozzle 40 has a tapered air outlet 43, while jacket 46 has a restricted opening 48. FIG. 3B shows that when jacket 46 sleeves jet nozzle 40, a fluid-introducing gap 47 is defined there between, and air outlet 43 and restricted opening 48 are aligned. FIG. 3B also shows container cap 51 that detachably covers reservoir container 44, and has a mist-discharging duct 52 that extends down into the reservoir container 44. Within this mist-discharging duct 52 is a diffuser dispersing baffle 49 that is suspended by support 50 from the container cap. Vents 66 allow aerosol to exit through duct 52, into the container cap 51. Also shown in FIG. 3B is duct 56 where airflow from user inhalation enters the nebulizing chamber of this device.

Figures 4A, 4B:
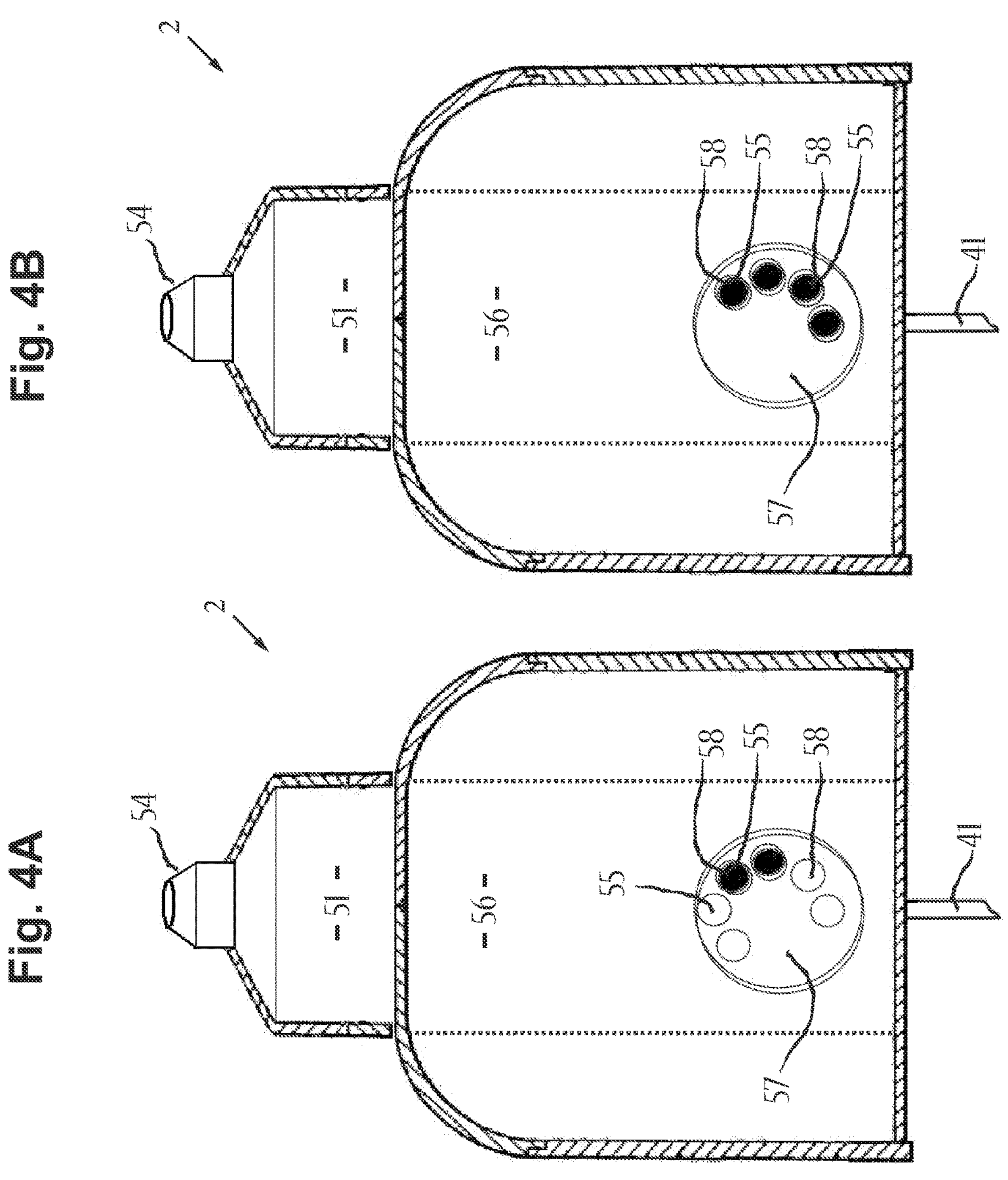
FIGS. 4A and 4B include additional side views of a back of the jet nebulizer device of FIG. 2, in accordance with an embodiment of the disclosure.

FIGS. 4A and 4B include additional side views of a back of the jet nebulizer device 2 of FIG. 2, in accordance with an embodiment of the disclosure. In this embodiment, the housing of the jet nebulizer device 2 has four fixed holes that serve as air inlets 55 to air duct 56. The rotatable wheel 57 also has four holes that serve as airway passages 58, which can differentially align with airway inlets 55 to allow the user to draw ambient air into air duct 56 during inhalation. When few of the air passages 58 of the rotatable wheel 57 are aligned with air inlets 55, as shown in FIG. 4A, there is greater restriction to airflow than when more of the air passages 58 of the rotatable wheel 57 are aligned with air inlets 55, as shown in FIG. 4B. In this example, FIG. 4A shows the alignment of two of the airway passages 58, while FIG. 4B shows the alignment of all of the airway passages 58. Thus, the airflow settings of FIG. 4A reduces the velocity of airflow through the jet nebulizer device 2, while the airflow settings of FIG. 4B increase the velocity of airflow through the jet nebulizer device 2.

Figure 5A:
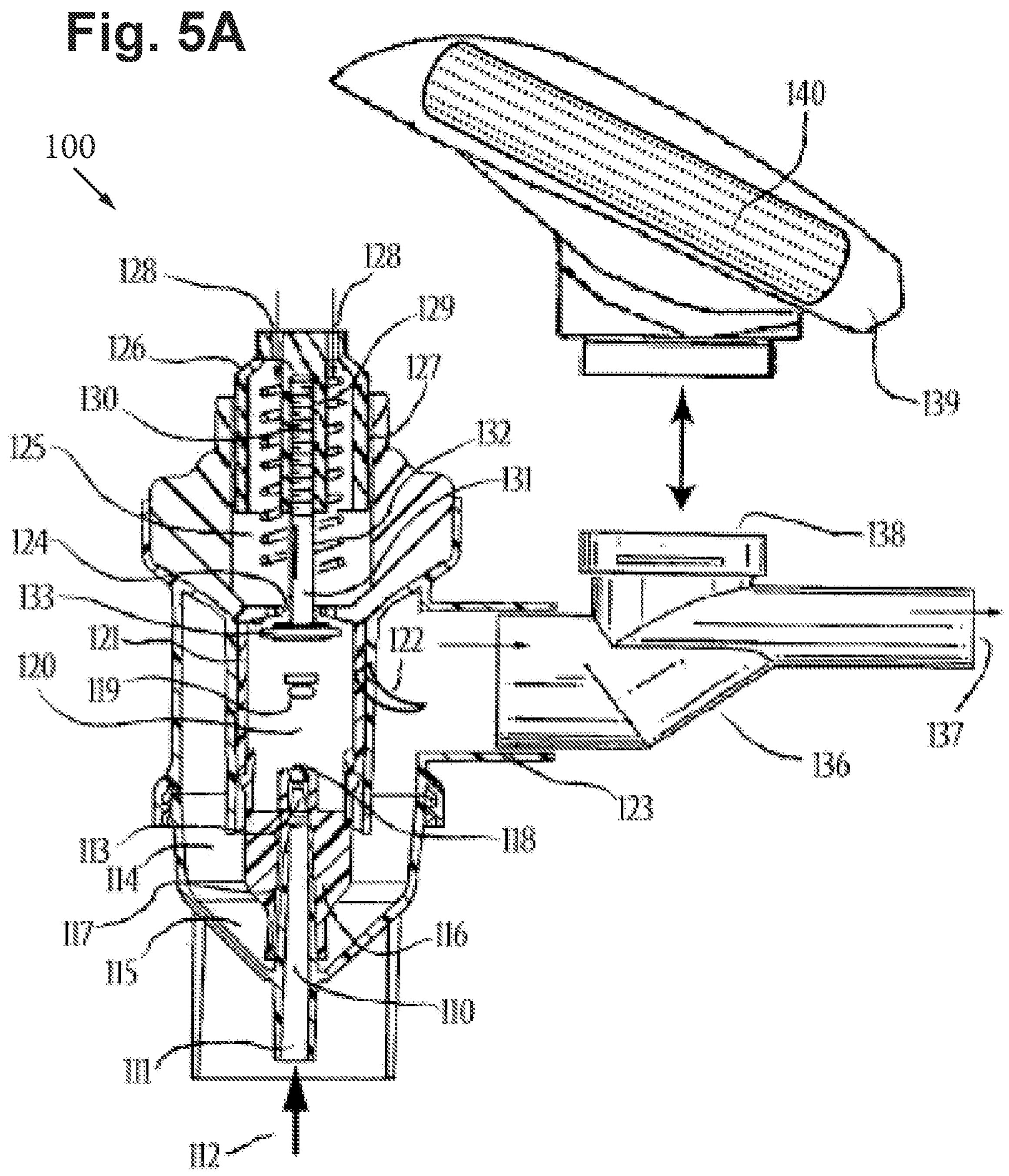
FIG. 5A includes a cross-sectional side view of a non-breath actuated jet nebulizer device with a calibrated airflow resistance control element and mouthpiece assembly, in accordance with an embodiment of the disclosure.

FIG. 5A includes a cross-sectional side view of a non-breath actuated jet nebulizer device (device) 100 with a calibrated airflow resistance control element (e.g., inhalation threshold resistance valve assembly 125) and mouthpiece assembly 136, in accordance with an embodiment of the disclosure. The device 100 may serve as a jet nebulizer with a calibrated airflow resistance control element adjustable by hand, and in this example is a non-breath actuated nebulizer. The device 100 comprising a jet nozzle 110 able to receive compressed air and/or compressed oxygen from compressed gas inlet 111 connected to a source of compressed gas 112. Sources of compressed gas can may include air pumps, portable air compressors, oxygen concentrators, or pressurized medical gas tanks. The device 100 can deliver medical gas to a patient chosen from the types of medical gas, including, but not limited to, compressed air, oxygen, nitrogen, nitric oxide, hydrogen sulfide, nitrous oxide, carbon dioxide, helium, cycloproprane, other anesthesia gases, and combinations thereof. When the embodiment serves as a disposable nebulizer, oxygen tubing, not shown, connects gas inlet 111 to sources of compressed gas 112. A gas flowmeter may also be connected in this gas circuit. When the embodiment serves as a hand-held, non-disposable nebulizer, the source of compressed gas 112 may even be a component of the device 100 itself, such as if the source of compressed gas is a miniature, battery powered, air compressor.

Jet nozzle 110 includes a tapered air outlet 113. The jet nozzle 110 resides inside of a liquid reservoir container 114, filled with at least one liquid medicament formulation 115. The reservoir container 114 is connected detachably and securely to the main device housing. A jacket 116 is sleeved around the jet nozzle 110 to define a fluid-introducing gap 117 there between. At the top of the jacket 116 is a restricted opening 118. When in use, a high-pressure air jet passes through jet nozzle 110 and out through the tapered air outlet 113, causing at least one propellant-free medicinal liquid 115 to flow into the fluid-introducing gap 117 due to negative pressure generated therein. Liquid becomes nebulized into aerosol as high-pressure forces this liquid through the restricted opening 118 of jacket 116; thereby serving as at least one site/element for generating and discharging an aerosol. Newly generated aerosol is dispersed as it comes in contact with a diffuser dispersing baffle 119 at high velocity.

The interior chamber 120 of the device 100 contains a conical section or chimney 121 that extends downward and surrounds the jet nozzle 110. Jacket 116 may be adjoined to chimney 121. Extension guides 122 may protrude from the walls of the chimney 121. Chimney 121 and its extension guides 122 prevent undesirable, larger droplets from exiting the device 100, and instead, cause such droplets to condense and return to the liquid reservoir 114. In this manner, smaller particles with a mass median aerodynamic diameter (MMAD), ideal for inhalation are able to freely exit the device through air outlet 123. Furthermore, chimney 121 and its extension guides 122 cause ambient air entering the device 100 to take a more tortuous flow path through device to ensure that an adequate amount of aerosol is entrained in this airflow to reduce particle size and/or to prevent particles from colliding and growing. Extension guides 122 of the chimney 121, or other baffles residing in the device 100, may be curved or spiral-shaped to cause cyclonic action of aerosol entrained airflow. Ambient air enters interior chamber 120 through a Venturi central aperture 124 located at the top of chimney 121. Airflow through this central aperture 124 is regulated by an inhalation threshold resistance valve assembly 125. Inhalation threshold resistance valve assembly 125 is comprised of a rotatable cap 126 with an integrally formed cylindrical wall slidably received through the cylindrical upper region of the device housing 127. One or more air inlet ports, shown as 128, are found at the top of rotatable cap 126. The rotatable cap 126 also has a tubular guide 129 extending through it. The tubular guide 129 has female threads 130 designed to receive the male threads of a thin rod 131. A load calibrated, compressible, coiled spring 132 biasing member, or other resilient or biasing member, is positioned inside of the rotatable cap 126, around the tubular guide 129 and thin rod 131. A circular disc 133 having some weight, along thin rod 131, is located within the interior chamber 120 of the device 100, thereby serving as the actuator piston of inhalation threshold resistance valve assembly 125. Circular disc 133 serves as an occlusion member, baffle, and flow throttling structure to restrict and control air flowing through central aperture (124). As spring 132 puts upward pressure on rotatable cap 126, circular disc 133 is pulled against the top surface of inner chamber 120, or chimney 121, and thus, blocks central aperture 124.

During inhalation, when the rate of airflow exiting the device exceeds the pressurized gas flowrate entering the interior chamber 120, and when the negative pressure, vacuum pressure, on the inhalation threshold resistance valve assembly 125 exceeds the force of the spring 132, the inhalation threshold resistance valve assembly 125 will open as the spring 132 compresses and the actuator piston moves down. When the inhalation threshold resistance valve assembly 125 is open, ambient air enters the device 100 through air inlets 128, entrains nebulized particles, and carries these particles out of the device 100 through air outlet 123. Calibrations of inhalation airflow resistance adapted to be presented to the user are chosen from the forms of presentation including, but not limited to, marked indicia, Braille indicia, raised indicia, vibrations, lights, sounds, electronic display, electronic sounds, and electronic vocalizations. Calibrating indicia are provided on the exterior cylindrical walls of the user interface, rotatable cap 126, for selecting inhalation resistance so that inhalation threshold resistance valve assembly 125 also serves as a calibrated airflow resistance control element. Inhalation resistance settings are able to be selected/dialed by the user by means of rotating the user interface rotatable cap 126 component like a dial, the distance that the thin rod 131 screws into the tubular guide 129 of the rotatable cap 126 also changes, thereby affecting the space between the rotatable cap 126 and the device housing 127, and thus, the compression of the spring 132. By varying the tension of the spring 132 via this mechanism for selecting inhalation resistance settings, one can control inhalation resistance and the velocity of airflow through the device 100, which may allow for aerosol delivery with sustained maximal inspiration, by guiding inhalation. Inhalation resistance settings provide significant inhalation resistance experienced by the user, requiring up to relatively strong resistance inhalation effort. The device 100 is adapted to selectively target aerosols to one or more different airway regions by selectively controlling airflow resistance through the device 100 and discharging aerosol particles of a desired mass median aerodynamic diameter, MMAD, one or more different airway regions being chosen from the regions, including, but not limited to, the upper airways, upper respiratory tract, nasal cavity, pharynx, larynx, lower airways, lower respiratory tract, trachea, bronchi, lungs, bronchioles, deep lung, and alveoli where systemic exchange takes place. One may also bypass the inhalation threshold resistance valve assembly 125 at times when having no resistance is desired. This may be done by manually pushing the rotatable cap 126 down by hand, and/or twisting the rotatable cap 126 into a locking position, which holds the inhalation threshold resistance valve assembly 125 open. One may also conceive of instances where the resilient or biasing member or spring 132 can be readily removed and replaced, and even replaced with another biasing member that has different tension properties.

The device 100 may also serve as an incentive device, a device having an incentive-like feature activated by significant inhalation, because movement of the inhalation threshold resistance valve assembly 125 from inhalation may provide a visual signal, and perhaps an auditory signal, to the user. The device is able to exercise at least some of the patient's muscles involved in inhalation using at least one inhalation resistance setting, as may be desired before, during, and after aerosol administration. This pulmonary physiotherapy, including during aerosol administration can provide at least one treatment benefit, selected from treatment benefits, including, but not limited to, reduced treatment time/period, reduced treatment frequency, enhanced aerosol delivery, enhanced aerosol entrainment, controlled aerosol flow, controlled airflow, sustained maximal inhalation/inspiration, enhanced aerosol targeting, enhanced aerosol deposition, enhanced aerosol penetration in obstructed airways, enhanced aerosol delivery efficiency, less medication needed, reduced medication waste, reduced side effects, breathing training, including during aerosol administration, breathing resistance/strength training, exercise of the muscles used during respiration, including during pulmonary rehabilitation, improved responsiveness in "before-after" pulmonary function tests, improved responsiveness to bronchodilator administration and exercise, maintenance of lung elasticity, helping to clear airways of fluid/mucous/secretions, helping to open/expand airways, helping to prevent hypoventilation, helping to prevent atelectasis, helping to prevent respiratory infection, including pneumonia, providing at least some incentive spirometry-like benefits and eliminating the need/cost for an incentive spirometer, better accommodation of different patient abilities, better accommodation of different medical conditions, better accommodation of different medications, and any combinations of treatment benefits thereof, to patients, including, but not limited to, patients with acute respiratory conditions, patients with chronic respiratory conditions, asthmatics, COPD patients, pre-operative patients, post-operative patients, including postoperative thoracic/chest/heart surgery patients and postoperative lung surgery patients, and patients having received ventilator assistance and anesthesia; said breathing exercise therapy (pulmonary physiotherapy) and aerosol delivery capable of being performed simultaneously, sequentially, and nonsimultaneously and non-sequentially.

This jet nebulizer embodiment (device 100) can also be further adapted to from a non-breath actuated nebulizer to serve as a breath activated nebulizer. For example, FIG. 5B includes a cross-sectional side view of a breath actuated jet nebulizer device (device) 101 adapted from the non-breath actuated jet nebulizer embodiment of FIG. 5A, in accordance with an embodiment of the disclosure. A movable diverter sheath 134 can be attached to the end of thin rod 131, e.g., a portion of the rod 134 which extends past circular disc 133. Jacket 116, which is sleeved around jet nozzle 110, can have an open region 135 that allows pressurized gas to escape without passing through restricted opening 118, and without causing nebulization. Upon a threshold level of inhalation, the actuator piston of inhalation threshold resistance valve assembly 125 moves downward by a distance 'h', thereby, placing diverter sheath 134, and optionally dispersing baffle 119, into nebulizing position. Nebulization occurs when diverter sheath 134 covers open region 135 so that pressurized gas can only escape through restricted opening 118 of jacket 116. When negative, vacuum, pressure from inhalation can no longer hold the inhalation threshold resistance valve assembly 125 open, such as towards the end of inhalation, the inhalation threshold resistance valve assembly 125 closes, the piston moves upward, and the diverter sheath 134 is no longer in a nebulizing position. In this manner, nebulization only takes place when the user is able to inhale through the device 100. Downward movement of the cap 126 may also signal that inhalation and nebulization is taking place. The rotatable cap 126 may also be unscrewed and removed from the rod 131, or manually pushed down and twisted to a position, which allows for continuous nebulization. One can also conceive of a breath activated nebulizer with a diverter sheath that stays down, thereby covering openings in the jacket 116, while in nebulizing mode, with or without inhalation, until exhalation moves the diverter sheath 134 up to uncover openings in the jacket 116, while in non-nebulizing mode.

Figure 5B:
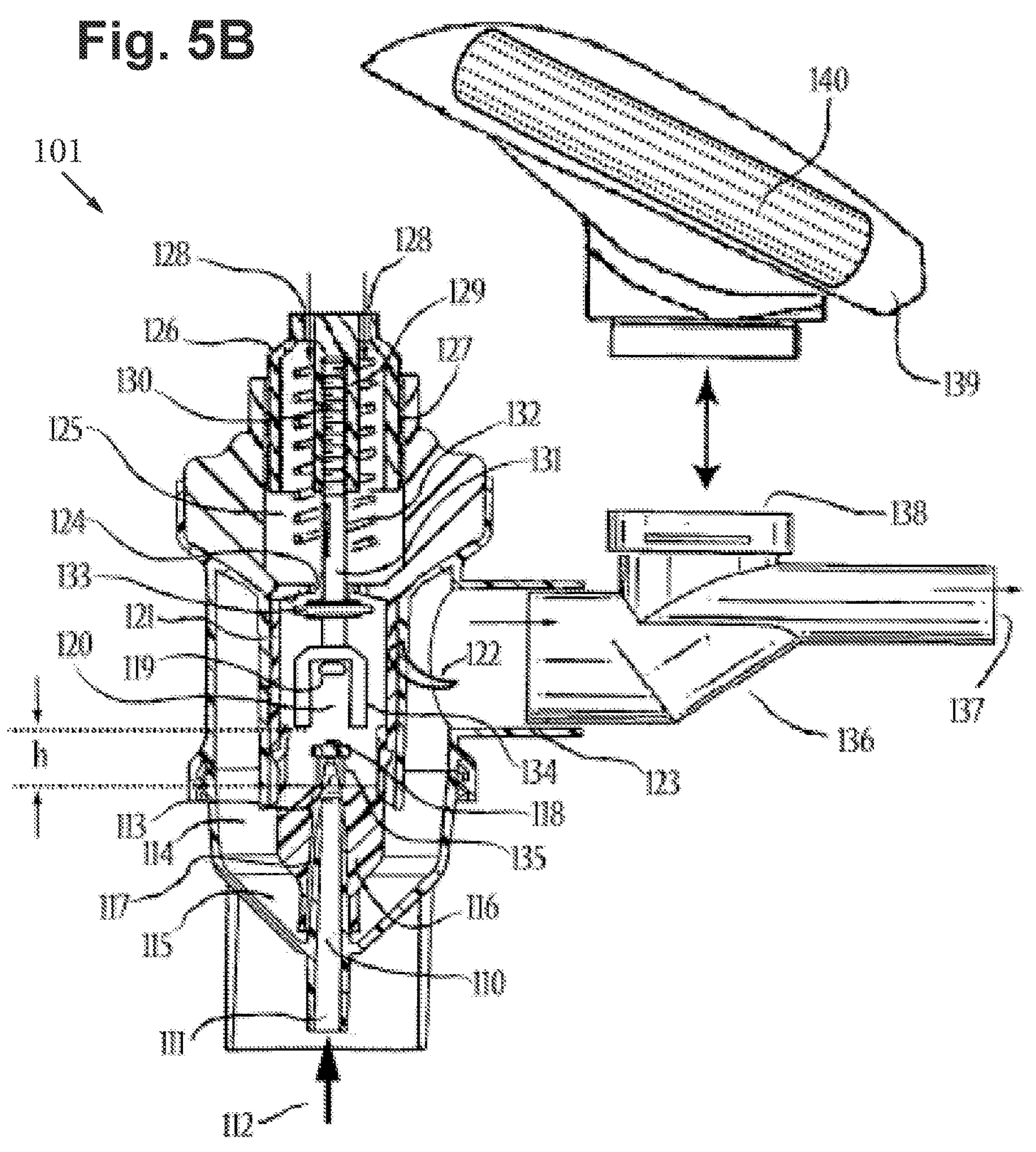
FIG. 5B includes a cross-sectional side view of a breath actuated jet nebulizer device adapted from the non-breath actuated jet nebulizer embodiment of FIG. 5A, in accordance with an embodiment of the disclosure.

Also shown in FIGS. 5A and 5B is user mouthpiece assembly 136 that attaches to device outlet 123. Airflow passes through the mouthpiece 136 and out through outlet 137. Said mouthpiece assembly 136 may contain an exhaust port 138, containing an elastomeric membrane, one-way, flap, valve, which vents user exhalation. An optional and/or removable filter housing assembly 139 may be aligned with exhaust port 138, to allow exhaled air to pass through a filter element 140, and out of the filter housing 139. A preferred filter element 140 may be a 3M® filtrate filter, or other HEPA filter, able to capture infectious particles and aerosol particles larger than 0.3 micrometers in diameter from exhalation, thereby preventing cross contamination to nearby individuals. A contaminated filter element may be cleaned or replaced as necessary.

Figure 6:
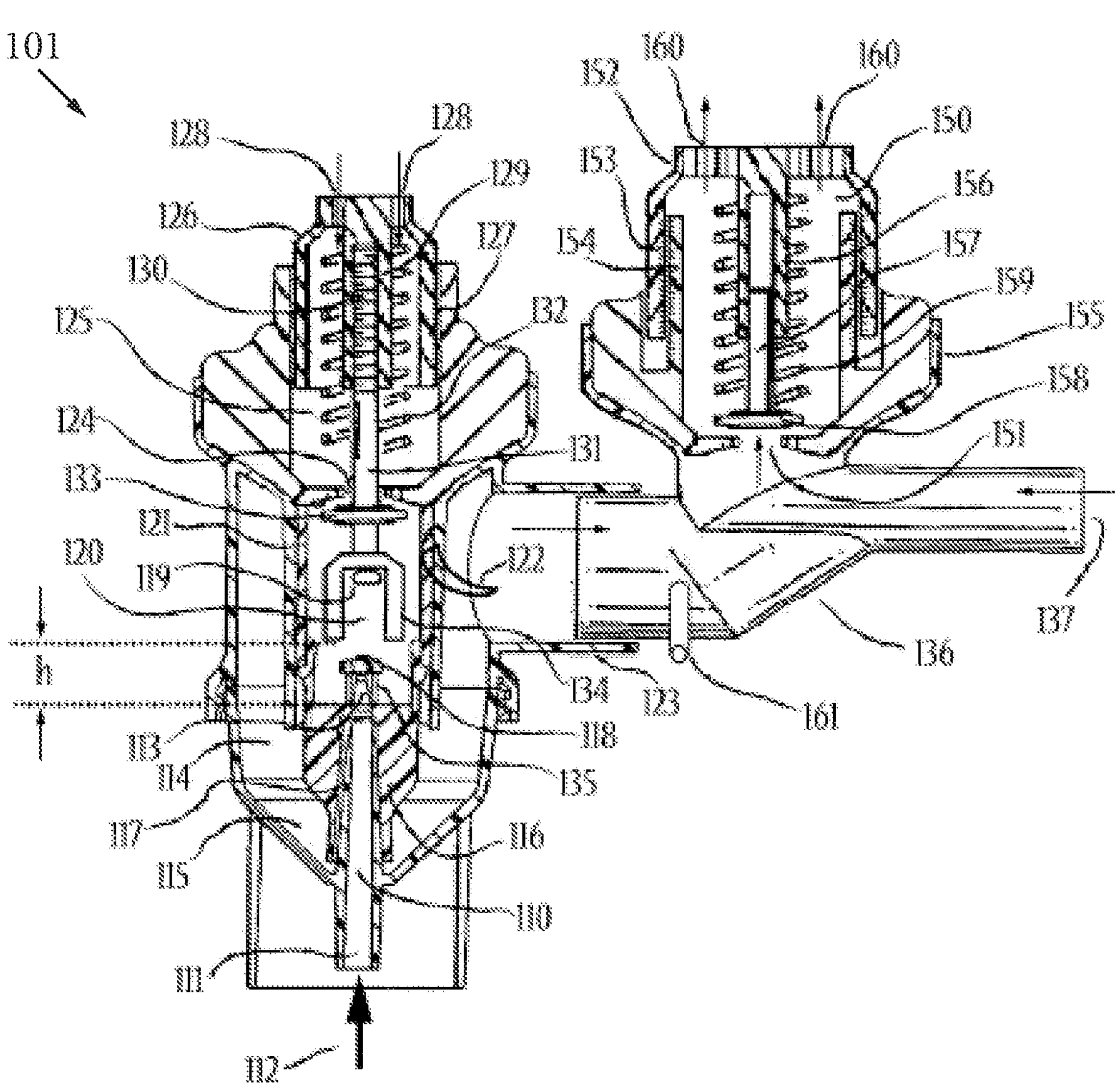
FIG. 6 includes a cross-sectional side view of the device of FIG. 5B with an exhalation threshold resistance valve assembly, in accordance with an embodiment of the disclosure.

Other examples of the device 100 may include an exhalation threshold resistance valve assembly instead of, or in addition to, the inhalation threshold resistance valve assembly 125. FIG. 6 includes a cross-sectional side view of the device 101 of FIG. 5B with an exhalation threshold resistance valve assembly 150, in accordance with an embodiment of the disclosure. The exhalation threshold resistance valve assembly 150 may be attached to or integrated with a mouthpiece assembly 136. The exhalation threshold resistance valve assembly 150 may perform positive expiratory pressure (PEP) therapy. Similarly, one can also conceive of alternative variations of the breath actuated jet nebulizer device where the exhalation threshold resistance valve assembly 150 is incorporated into the main body of the breath actuated jet nebulizer device, rather than as a component of a mouthpiece 136. The exhalation threshold resistance valve assembly 150 regulates airflow passing through aperture 151. The exhalation threshold resistance valve assembly 150 is comprised of a rotatable cap 152 with a threaded, integrally formed cylindrical wall 153 that screws onto the upwardly extending, threaded cylindrical walls 154 of mouthpiece upper housing 155. Rotatable cap 152 also has a tubular guide 156 extending through it. The tubular guide 156 is designed to slidably receive a thin rod 157. A circular disc 158, along thin rod 157, is located above mouthpiece upper housing 155, and is able to cover aperture 151, thereby serving as the actuator piston of exhalation valve 150. A load calibrated, coiled spring 159, or other resilient or biasing member, is positioned around tubular guide 156 and thin rod 157, compressed between rotatable cap 152 and circular disc 158. One or more air outlet ports, shown as 160, are found at the top of rotatable cap 152. Air exits through ports 160 when the exhalation threshold resistance valve assembly 150 is open. The exhalation threshold resistance valve assembly 150 opens when there is enough internal air pressure to place upward force on circular disc 158, so as to overcome the tension of the spring 159, and further compress the spring so that rod 157 can slide upwards within tubular guide 156. Disc 158 is able to move upward until it reaches, or is hindered by, tubular guide 156. Air pressure builds within the device 101 from user exhalation through mouthpiece end 137, to open the exhalation threshold resistance valve assembly 150. The exhalation threshold resistance valve assembly 150 closes again when air pressure decreases, such as when exhalation stops. The amount of pressure needed to open the exhalation threshold resistance valve assembly 150 can be adjusted by further screwing or unscrewing cap 152 onto cylindrical walls 154 of upper housing 155, thereby, varying the distance between cap 152 and upper housing 155. This in turn varies the compression and tension of the spring 159. Calibrating indicia are provided on the exterior cylindrical walls of rotatable cap 152, so that exhalation valve 150 can serve as a calibrated airflow resistance control element, as it is rotated like a dial to adjust airflow resistance settings. The device 101 may also serve as an incentive device because movement of the exhalation threshold resistance valve assembly 150 from exhalation may provide a visual signal, and perhaps an auditory signal, to the user.

Certain variations of the device 101 may also use compressed air, from a first or second source, to provide positive airway pressure therapy, and may also deliver aerosol in conjunction with positive airway pressure. A Venturi may also be used to draw in ambient air, and to accelerate/ decelerate air flow in the device. Positive airway pressure helps expand lungs and treat atelectasis. The positive pressure may be continuous during all portions of the breathing cycle. Or, a means of interrupting continuous positive air flow at a certain frequency, such as using a flow interrupter valve, can deliver high-frequency pulses of positive pressure, to provide for an oscillation breathing treatment, which may help clear patient airways by helping to free mucous secretions. An optional manometer, pressure, port 161 and removable cover, not shown, can allow for a manometer to accurately measure the positive pressure that the patient is receiving from the device, and may also serve as a pressure relief port. Positive airway pressure may also produce a back pressure in exhaled air to provide PEP therapy.

Figure 7:
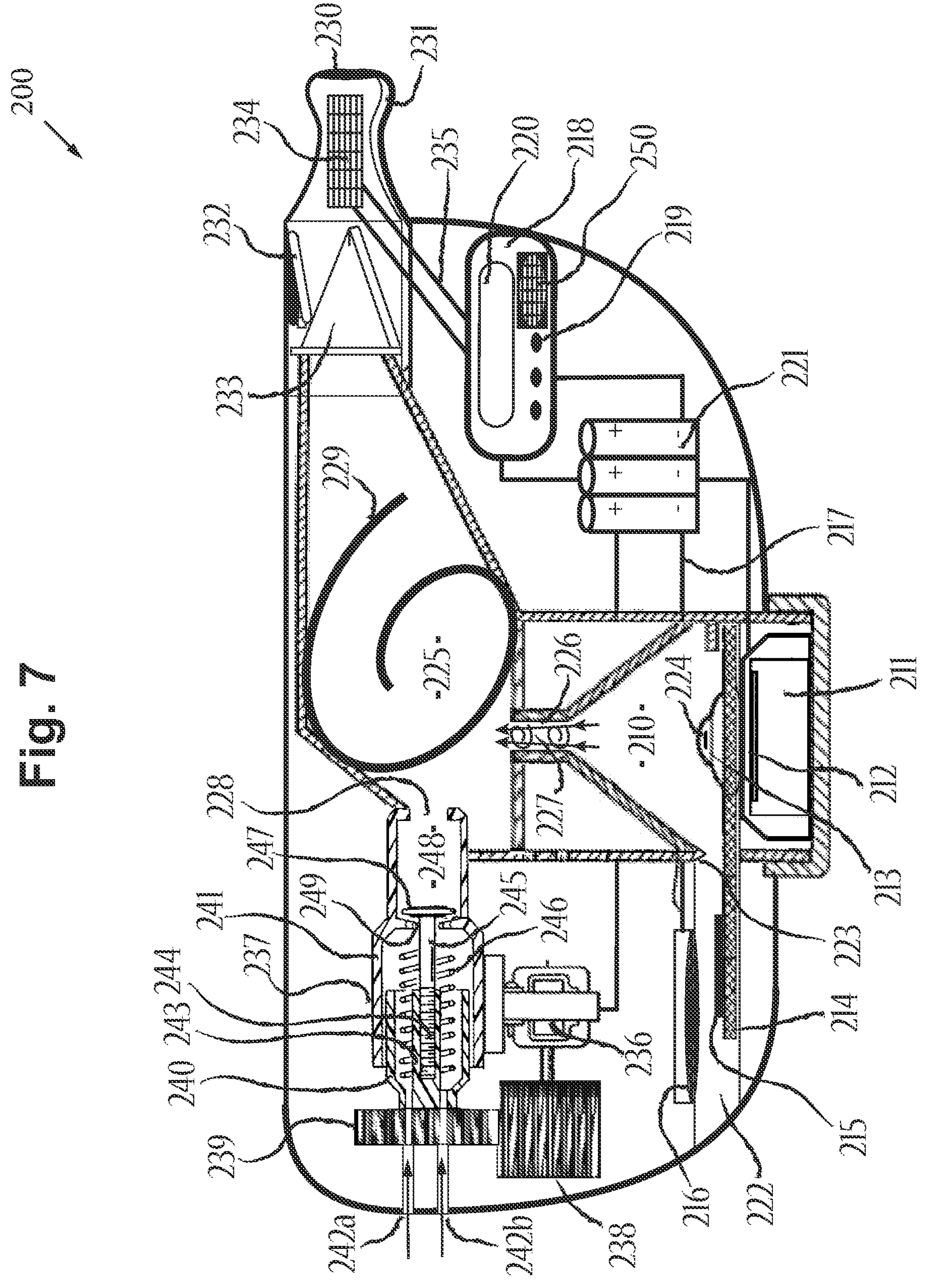
FIG. 7 includes a cross-sectional side view of a portable, sensor activated vaporizer powered by battery, in accordance with an embodiment of the disclosure.

FIG. 7 includes a cross-sectional side view of a portable, sensor activated vaporizer powered by battery (device) 200, in accordance with an embodiment of the disclosure. The device 200 comprising a horn-shaped, first chamber 210. A piezoelectric transducer 211 that is made to oscillate, vibrate, while in contact with the proximal end of first chamber 210, such as to send vibrations to that chamber 210. A heating element 212 can be comprised of an electrically resistive heating support or resistor, and is located in close communication with the proximal end of first chamber 210, such as to send heat to that first chamber, including sending heat to a medicament. The piezoelectric transducer 211 and heating element 212 may be housed together. A (preformed) blister pack 213, or other medicament packaging, filled with a medicament can be housed on a slidable structure, slide, strip (medicament slide) 214, that can be inserted into first chamber 210, such as along or near its proximal end. Medicament slide 214 can contain a coded tag 215, such as a bar code, microchip, transmitter, radio-frequency identification tag, or other means, that can be detected and/or analyzed by an electronic tag reader 216. Tag reader 216 is able to detect the presence of the blister pack 213 and medicament slide 214. The coded information detected may also include the type of medicament and/or also its dosage and/or its serial number. The tag reader 216 may send this information through an electronic circuit 217, preferably wired to a digital control unit 218, with user inputs 219, and a digital display 220, such as LCD or LED. The digital control unit 218 controls the operation of the piezoelectric transducer 211 and heating element 212, using power from batteries 221. These batteries 221 can either be rechargeable or non-rechargeable batteries. The detection and/or analysis of the coded medicament information 215, by the reading device 216, may allow the digital control unit 218 to turn the piezoelectric transducer 211 and heating element 212 on for certain durations, and/or may determine the desired power and frequency to operate the piezoelectric transducer 211, and may determine the desired power and temperature to heat the heating element 212, for proper delivery characteristics of that particular medicament code.

When medicament slide 214 is inserted into the device 200, through the medicament port channel 222, a piercing means or mechanism 223 can remove or cause openings 224 on the top of blister packaging 213, by which medicament can be released into the first chamber 210. When activated, heating element 212 is able to vaporize the medicament substance from medicament slide 214 by sending thermal energy to the substance by conduction and/or convection. In other embodiments, heating element 212 can be located on medicament slide 214 as an electrically resistive heating support, such as a metal foil support, which may even be part of blister packaging 213. As such, medicament may be coated on this metal foil support. After vaporization, preferably with minimal degradation products of medicament, the vapor can cool and condense to form a condensation aerosol available for inhalation. As will next be described, this vapor can be efficiently carried to an aerosol holding chamber 225 where the particles can cool further.

First chamber 210 is connected to a second chamber 225 via a narrow orifice or channel 226. Vibration of the proximal end of first chamber 210 by the vibrations caused by piezoelectric transducer 211, sets up pressure variations, as well as standing waves and/or acoustic waves, within the first chamber, causing air in the first chamber 210 to move back and forth through channel 226, while vortices of air are formed at channel 226, leading to second chamber 225. A synthetic jet of air 227 is thus created by these vortices, resulting in the net flow of air from first chamber 210 into second chamber 225. Vapor and condensation aerosol is entrained in this airflow and evacuated from first chamber 210, and carried to the second chamber 225, by a synthetic jet 227 via channel 226. When the medicament substance is a dry powder, and the heating element 212 does not vaporize some or all of the powder, such as when the heating element 212 is not activated or when the heat transfer is less than 100% efficient, piezoelectric transducer 211 can still vibrate and mix air in the first chamber 210 to disaggregate the dry powder released from blister pack 213, to form an aerosol. The aerosolized dry powder is entrained in the air and evacuated from first chamber 210, and carried to the second chamber 225, by a synthetic jet 227 via channel 226. As such, the device 200 can serve as a dry powder inhaler.

Second (reserve) chamber 225 can serve as an aerosol reserve, holding, chamber. Airflow enters device chamber 225 through inlet passage 228, where it may be vortexed by the curved interior walls or spiral baffles 229 of the second chamber 225, before exiting the device 200 via outlet end 230. Airflow outlet end 230 can consist of a user mouthpiece 231 that contours to the user's lips, allowing for an airtight seal. Said mouthpiece 231 may contain an exhaust port 232 (comprised of an elastomeric one-way, flap valve) that vents user exhalation, while one-way valve 233, preferably a duckbill valve, prevents exhalation from entering the interior of the device 200.

The device 200 may also contain one or more airflow sensors 234, that forms a switching circuit with the digital control unit 218 via circuit leads 235. Detection of user airflow may signal the digital control unit 218 to activate and/or regulate piezoelectric transducer 211 and heating element 212 for aerosol delivery. Airflow sensors 234 may also provide feedback of airflow and/or breathing pattern data to a digital control unit (or microprocessor) 218, which can interpret the data and can adjust airflow resistance by sending an electronic signal to an electric motor 236, controlling a calibrated airflow resistance control element 237 by means of gears 238 and 239. The acoustic horn shape of the device 200, along with its associated synthetic jet, is preferred, although one can envision other embodiments where the acoustic horn is not used. The main feature of these embodiments are, however, a calibrated airflow resistance control element 237 that controls the velocity and/or volume of airflow through the device. There exist many ways to achieve this calibrated airflow resistance control element, and one such way is way is with an inhalation threshold resistance valve assembly that regulates airflow entering chamber 225 via inlet 228.

The inhalation threshold resistance valve assembly is comprised of a rotatable cap 240 with an integrally formed cylindrical wall slidably received through a cylindrical housing 241. Gear 239 is connected to, or forms the top of, rotatable cap 240. Gear 239 and/or the top of rotatable cap 240 contain one or more air inlet ports 242 that allow airflow to enter airflow resistance control element 237, which allows airflow to enter second chamber 225 via inlet 228, when the inhalation threshold resistance valve assembly is open. Rotatable cap 240 also has a tubular guide 243 extending through it. The tubular guide has female threads 244 that is designed to receive the male threads of a thin rod 245. A load calibrated, coiled spring 246, or other resilient or biasing member, is positioned inside of the rotatable cap 240, around the tubular guide 243 and thin rod 245. A circular disc 247, along thin rod 245, is located within a chamber region 248, adjacent to reserve chamber 225, and serves as the actuator piston of threshold resistance valve 237. As spring 246 puts outward pressure on rotatable cap 240, circular disc 247 is pulled against the proximal surface of chamber 248, thereby blocking this chamber's proximal aperture 249.

Upon inhalation, when a threshold level of negative pressure, vacuum pressure, is applied on the inhalation threshold resistance valve assembly, the inhalation threshold resistance valve assembly will open as the spring 246 compresses and the actuator piston moves away from its resting position. Rotatable cap 240 is able to slide within cylindrical housing 241, commensurate with gear 239 being able to slide along gear 238. When the inhalation threshold resistance valve assembly is open, ambient air enters the device 200 through air inlets 242, and passes through chamber 248 and reserve chamber 225, entraining aerosolized particles, and carrying these particles out of the device 200 through outlet 230. The inhalation threshold resistance valve assembly closes when negative pressure within chamber 225, and chamber 248, can no longer overcome the tension of the spring. The airflow resistance control element 237 also serves as a calibrated airflow resistance control element. As electric motor 236 turns gears 238 and 239, rotatable cap 240 is rotated like a dial. When the rotatable cap 240 is rotated, the distance that the thin rod 245 screws into the tubular guide 243 of the rotatable cap 240 also changes, thereby affecting the space between the rotatable cap 240 and the cylindrical housing 241, and thus, the compression of the spring 246. By varying the tension of the spring 246, one can control inhalation resistance and the velocity of airflow through the device 200, which may allow for aerosol delivery with sustained maximal inspiration, inhalation. The number of partial or full revolutions that the electric motor 236 must spin in order to turn gears 238 and 239, and thus, rotatable cap 240, necessary to adjust the tension of load calibrated spring 246, is programmed into the digital control unit 218. Thus, digital control unit 218 can automatically adjust airflow resistance settings based on user inputs 219, or from data signals generated from airflow sensor 234. Other embodiments may utilize a manual means for adjusting calibrated airflow resistance settings.

The digital control unit 218 may also contain a microprocessor that can perform one or more functions, such as: providing an alarm function to signal when a treatment is due, a timer function to measure the duration of treatment and/or to turn off operation after a certain treatment duration, a counting function to determine the number of treatments, a function to keep track of the airflow resistance settings during treatment, a time/date function to track the treatments of one or more different medicament formulations, the ability to store settings for different medicament formulations, along with any other functions obvious to the use of this device 200. The digital control unit 218 may have an electronic speaker 250 that provides auditory feedback to the user regarding the user's progress and/or to adjust the user's inhalation rate or breathing pattern, and/or to provide the user with incentive. The electronic speaker 250 may provide human sounding words to provide such auditory feedback, and may also voice aloud device settings and functions. The digital control unit 218 may contain a USB port and/or memory card so that data can be interfaced with a computer or respiratory instrument.

This embodiment utilizes a medicament strip 214 with a single medicament blister pack 213. One can envision other embodiments where multiple blisters are housed on the strip, or a device that can hold and use multiple unit dosages of medicament, sequentially.

Figure 8:
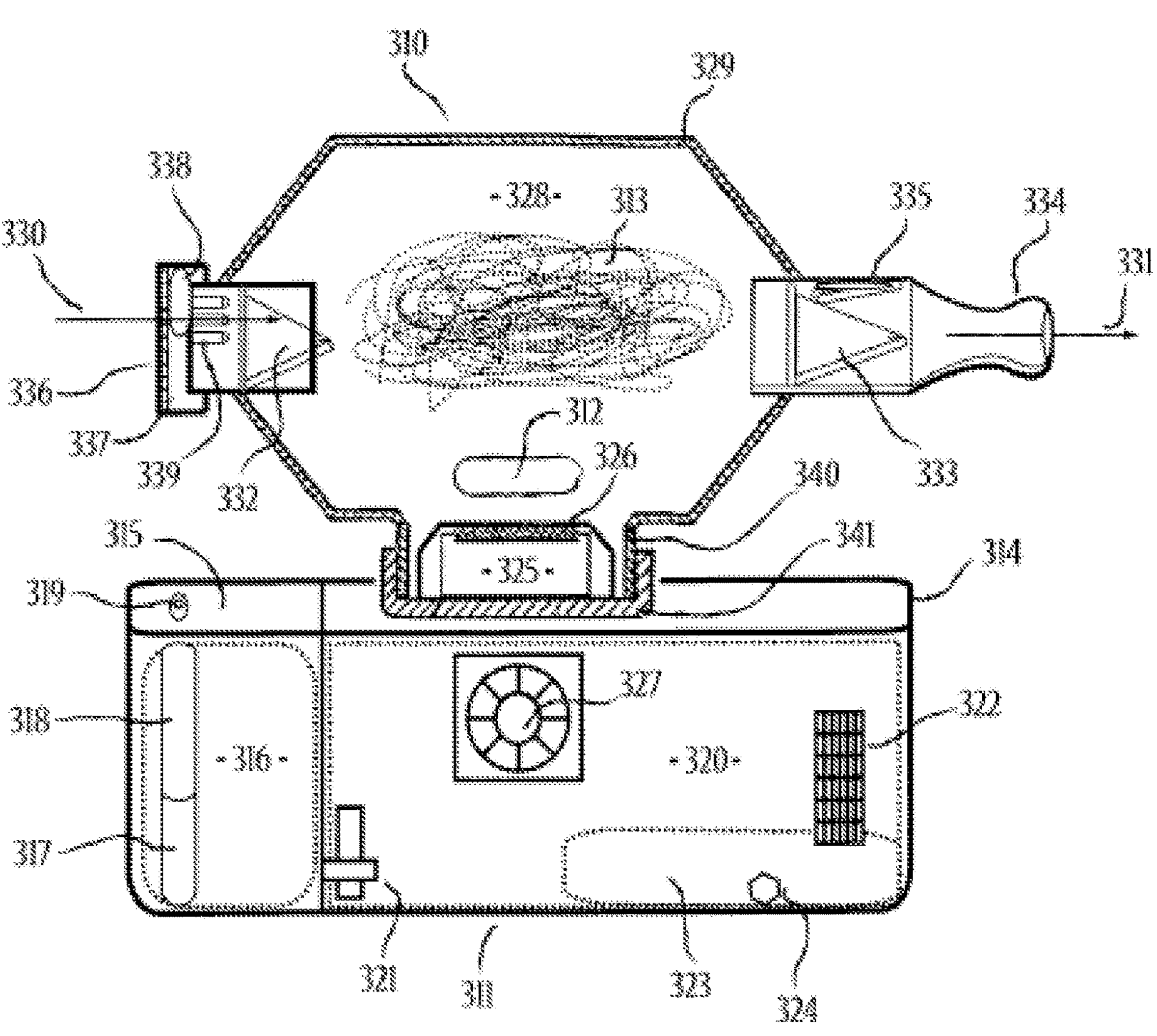
FIG. 8 includes a cross-sectional side view of a vaporizer powered by a fuel, in accordance with an embodiment of the disclosure.

FIG. 8 includes a cross-sectional side view of an aerosol delivery device 310, in accordance with an embodiment of the disclosure. The aerosol delivery device 310 uses energy from a micro power source, such as a fuel cell 311, to vaporize a substance 312 to produce a condensation aerosol 313 for inhalation. Fuel cells are a type of electrochemical cell that generate direct current through oxidation of a fuel, usually in the presence of an electrolyte, without the danger of high-temperature combustion. Some example combinations of fuels and oxidants include: hydrogen and oxygen, and hydrocarbons and alcohols. Fuel cells also have an anode catalyst that breaks down fuel into electrons and ions. These ions are converted into waste chemicals, such as water or carbon dioxide, by the cathode catalyst. Like fuel cells, batteries also make use of electrochemical energy, but as they store this energy, and over time, batteries can lose their charge; whereas, fuel cells can be more reliable sources of energy, when stored for extended periods of time. Many fuel cells can achieve a higher energy density by volume, and a higher energy density by weight, than most lithium-ion battery alternatives. Fuel cell cartridges may be easily refillable or as disposable as a butane lighter. With a proton exchange membrane or polymer electrolyte membrane, PEM, direct methanol fuel cells are small and convenient for portable devices. For instance, direct methanol fuel cells utilize a water/methanol mixture as fuel, and oxygen, such as from ambient air, as an oxidant in the following oxidation-reduction reaction:

Half Reaction at the Anode:

$$CH_3OH+H_2O\rightarrow CO_2+6H^++6e^-$$

Half Reaction at the Cathode:

$$O_2+4H^++4e^-\rightarrow 2H_2O$$

The Overall Fuel Cell Reaction:

$$CH_3OH+1.5O_2\rightarrow CO_2+2H_2O$$

What follows is a description of the main components of fuel cell 311, which powers aerosol delivery device 310. The main fuel cell housing 314 is adjoined to fuel cell cartridge 315, and in some embodiments may be removably attached. The fuel cell cartridge 315 contains a fuel reservoir 316 and a fuel 317, with a level or volume that can be viewed from a see-through window 318. The fuel cell cartridge 315 may also contain a fuel inlet 319 that allows the fuel cell cartridge 315 to be refilled, with a refueling device, not shown, as an alternative to being replaced when fuel 317 is depleted. Within the fuel cell housing 314 is the reaction chamber 320 that contains all the components of a functional fuel cell, not shown, such as an anode and anode catalyst, a cathode and cathode catalyst, and an electrolyte, which may be a PEM. Fuel 317 may be gravitationally fed into the reaction chamber 320 from the fuel reservoir 316, or other methods, such as capillary pressure or a micro pump, may be used. A switch, shunt, or actuator 321 controls the movement of fuel 317 into the reaction chamber 320, and essentially serves as a means to activate the fuel cell 311. In some embodiments, actuator 321 may be part of, or a lever to, a manual pump to draw fuel 317 into the reaction chamber 320. Vent 322 allows an oxidant, such as oxygen from ambient air, to enter the reaction chamber 320. Emission reservoir 323 allows the, liquid, product(s) of the chemical reaction, such as water, to collect until released through emission plug or outlet 324. Gaseous product(s) of the chemical reaction, such as carbon dioxide, may also be released through a vent similar to, or the same as, vent 322.

Electrical energy produced by the fuel cell 311 powers a heating element 325, which is a resistor. Heating element 325 has a heating surface 326, which may be metallic or ceramic, that can vaporize a substance 312, either by thermal conduction, and/or by thermal convection, to produce a condensation aerosol 313. In certain embodiments, heating element 325 may serve as an electrostatic charger able to produce an electrostatic charge in the substance, or particles thereof. Electrical energy between the fuel cell 311 and the heating element 325 is regulated by control element 327. Control element 327 may serve as a switch to turn the heating element 325 on or off, and/or to turn the fuel cell 311 on or off, or may serve as a dial to regulate the amount of electricity going to the heating element 325. In some embodiments, control element 327 is a thermostat that regulates the temperature of heating element 325, which may, or may not, be set by the user, and may include calibrated indicia. In other embodiments, control element 327 may consist of a pressure sensing or conductivity sensing lead, a touch panel, activated by direct user contact or touch. In still in other embodiments, control element 327 may consist of a timer that shuts off power to the heating element 325 after a specified duration of time.

The condensation aerosol 313 that forms upon the cooling of a substance 312, after being vaporized, is contained within an aerosol, holding, chamber 328. Aerosol chamber 328 is comprised of a chamber housing 329, which has an air inlet end 330 and an air outlet end 331. The device 310 may contain one-way valves 332 and 333, preferably duck-bill valves, that trap the condensation aerosol within the chamber until vacuum pressure, or a significant threshold vacuum pressure, generated from user inhalation is able to open said one-way valves 332 and 333. In this manner, condensation aerosol 313 is thusly contained in chamber 328 until airflow, originating at air inlet end 330, carries the aerosol through the device 310 and out to the end user through the airflow outlet end 331 of the device 310. The airflow outlet end 331 of the device 310 may contain a mouthpiece 334 that contours to the user's lips, allowing for an airtight seal. Said mouthpiece 334 may contain an exhaust port 335, comprised of an elastomeric one-way, flap valve that vents user exhalation, while one-way valve 333 prevents exhalation from entering the interior of the device. In alternative embodiments of this device 310, a mouthpiece 334 may be attached to the airflow outlet end 331 via a long and/or flexible tube or hose.

This device 310 also has a calibrated airflow resistance control element 336, which in this embodiment, consists of a user controlled airflow resistance dial 337 with one or more supplemental apertures 338. The user controlled airflow resistance dial 337 is flush with the airflow inlet end 330 of the device 310. Rotation of user controlled airflow resistance dial 337 aligns supplemental aperture(s) 338 with one or more airflow inlet passages 339, thereby controlling the amount of airflow allowed to enter the device 310 and travel through these passages 339, having the effect of controlling the velocity and/or volume of airflow through the device 310. This, in effect, allows the user to adjust the dynamics of how the condensation aerosol 313 is formed, entrained, and evacuated from the aerosol chamber 328, and may allow for aerosol delivery with a sustained maximal inspiration, inhalation.

In this embodiment, the housing 329 of aerosol chamber 328, and/or the heating element 325, and/or its surface 326, may be removably attached, so that substance residue can be removed from surface 326, and replaced by new substance. The substance may be in raw form, or may be contained or coated on a thin strip, wafer, pellet, or capsule. The contours of surface 326 may be designed to help hold the substance, and/or to help grind the substance into smaller pieces, making the substance more readily accessible for receiving heat. Aerosol chamber housing 329 may be removed for cleaning, as well. As such, aerosol chamber housing 329 may have a threaded base 340, that screws into a threaded base support 341 of the fuel cell housing 314.

Other embodiments of a micro power source may be envisioned for this device that utilize a fuel source to produce thermal heat, instead of, or in addition to, producing electricity as a fuel cell does. Other micro power sources may include a micro engine, micro-gas turbine, which may produce heat and electricity through combustion of a fuel that turns the turbine, or a micro heater that uses combustion or direct oxidation to release thermal energy. Such thermal energy may be applied to a heating surface, such as a radiator with a fan and/or air pump, to vaporize a substance using thermal conduction and/or convection currents. Other embodiments may use may utilize the electric energy produced by a fuel cell or micro-turbine to power a light or laser source, or a microwave source, to vaporize a substance with radiation. Additional other embodiments may include a cooling means by which the vapor produced is cooled more rapidly, such as having a water and/or ice cooling and/or conditioning means.

Figure 9:
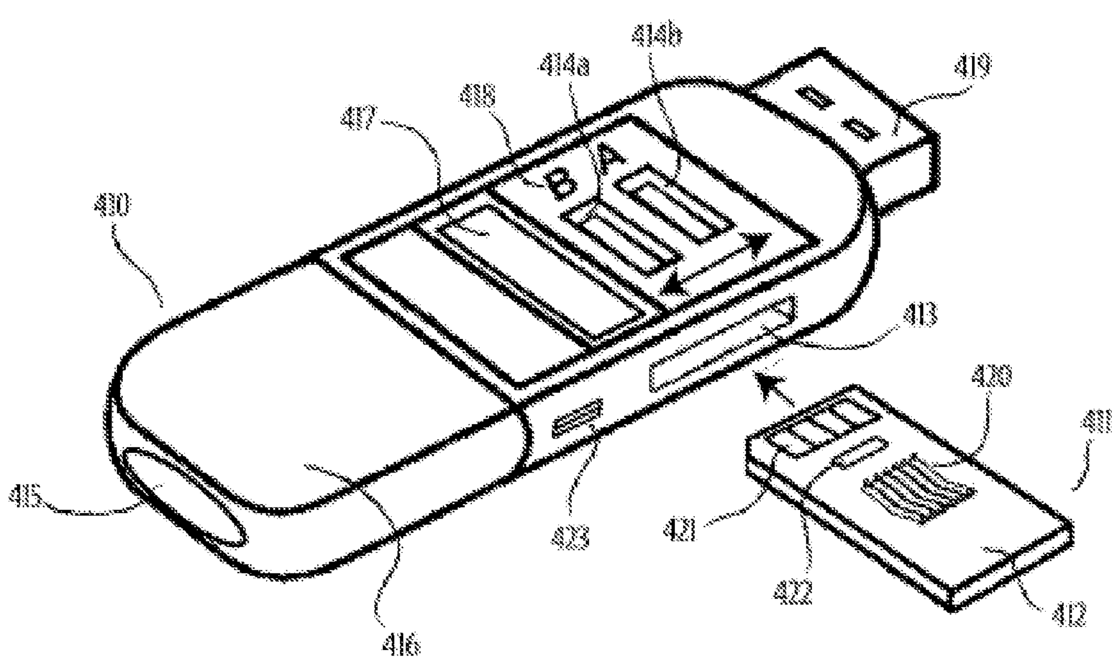
FIG. 9 includes a perspective view of a digital vaporizer with flash drive that is powered through a USB port in accordance with an embodiment of the disclosure.

FIG. 9 includes a perspective view of a digital vaporizer with flash drive (aerosol delivery device 410) that is powered through a port 419 in accordance with an embodiment of the disclosure. The aerosol delivery device 410 comprising a replaceable/disposable, medicament cartridge or card (medicament cartridge) 411, which may be shaped like a flash SD memory card commonly used in other electronic devices, such as computers and digital cameras. Medicament cartridge 411 has a housing 412, which may be asymmetrically shaped for proper orientation when inserted into the device 410 through medication card slot 413. Air enters device 410 through one or more air inlet passages **414*a* and 414*b*, and, aerosolized, air exits the device 410 through at least one outlet 415, which the user can inhale from. As such, the distal end of the device 410 has a mouthpiece region 416 that allows communication of the device 410 with the user's lips during inhalation. In some embodiments, this mouthpiece region 416 may be removably attached to the device, so that it may be cleaned more efficiently. In the current embodiment, a slidable cover or panel 417 is selectively moveable, as shown by arrows, along the face of the device 410, and is able to, incrementally, cover one or more air inlets 414*a* and 414*b*, and thus serves as an airflow resistance control element for controlling the velocity and/or volume of airflow into and/or through the device 410. This, in effect, allows the user to adjust the dynamics of how the condensation aerosol is formed, entrained, and/or evacuated from the device 410, and may allow for aerosol delivery with a sustained maximal inspiration, inhalation. Calibrated indicia 418 can be provided for this airflow control element, so the user can adjust airflow passages 414**.

The device 410 may also have a USB connector or USB port (port) 419, or micro USB connector or port, or the like, which can be used to send data or instructions between the inhaler and an external electronic device, such as a computer, respiratory instrument, or portable device, such as a smart phone, when the inhaler is connected to said electronic device, either directly or via a USB cable, or the like. The port 419 may also be used to draw electrical power from the external device, or an A/C adapter power cord, to recharge an internal battery, if present, and/or to power the circuitry of the device 410, such as the circuitry of the medicament cartridge 411, including powering the vapor element 420. Electrical contact pins 421 on the medicament card 411 allow for electrical communication between the medicament cartridge 411 and the device 410. The medicament card 411 may also have a selection switch or lock switch 422 that can regulate the use of the medicament card 411.

This embodiment may allow this device 410 to serve as a smaller, more portable inhaler than other larger, more cumbersome device products, while having many advantages such as rapid onset, ease of use, and consistent dose and particle size. Moreover, the overall shape of this inhaler device 410 embodiment can resemble the shape of a common USB flash drive, which may allow for greater user compliance as the inhaler device 410 is less obtrusive in public. Such a portable inhaler can be stored or transported in a pocket, or connected via bracket 423 to a key chain, bracelet, necklace, or lanyard, not shown; thereby, allowing for greater convenience than larger vaporizer products, and making this type of inhaler suitable for both daily use and/or emergency situations. Dry medicament associated with vapor element 420, such as a lyophilized powder or other dry coatings, may also have the advantage of better storage and longer shelf life than other, liquid, formulations, and may have less issues with solubility and dependency on other reagents for formulation that generally limit other medicament applications.

Figure 10:
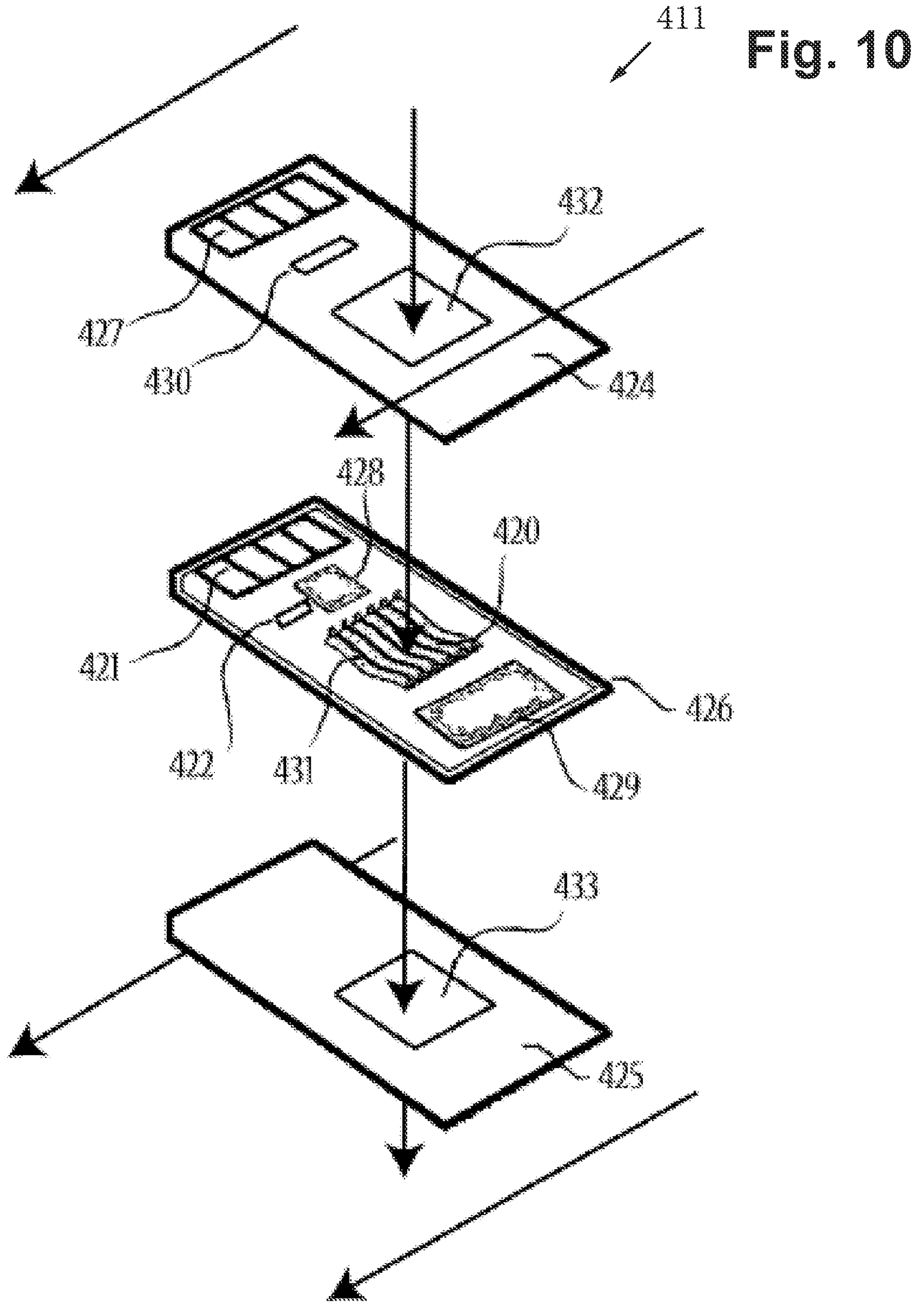
FIG. 10 includes an exploded view of the medicament cartridge with vapor element configured for use with the USB flash drive digital vaporizer of FIG. 9, in accordance with an embodiment of the disclosure.
Figure 11:
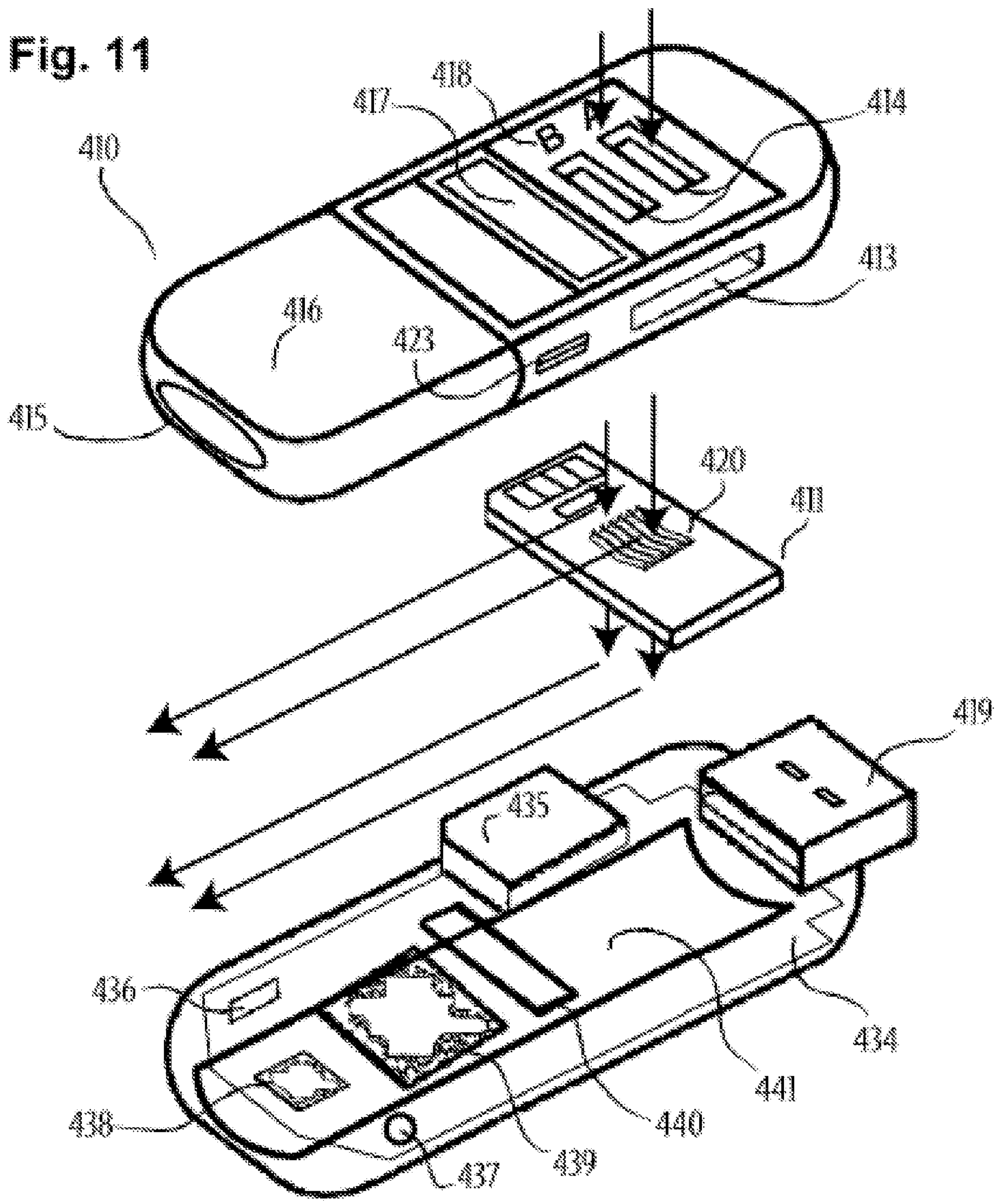
FIG. 11 includes an exploded view of the device of FIG. 9, in accordance with an embodiment of the disclosure.

FIG. 10 includes an exploded view of medicament cartridge 411 with vapor element 420 configured for use with the device 410 of FIG. 9, in accordance with an embodiment of the disclosure. FIG. 11 includes an exploded view of the USB flash drive digital vaporizer of FIG. 9, in accordance with an embodiment of the disclosure. Turning to FIG. 10, the direction of airflow over, through, and around the medicament cartridge 411 are indicated by arrows. The medicament cartridge 411 has a first half housing 424 and a second half housing 425 that, together, form housing 412, with an internal circuit board 426, such as a printed circuit board or printed circuit assembly, therein. This circuit board 426 is connected to an arrangement of exterior facing, electrical contact pins 421 for communication with the device 410. Electrical contact pins 421 are exposed and may be further supported by contact window 427 of first half housing 424. Like a conventional memory card, the circuit board may include a microcontroller chip 428, such as an SD controller chip, and a flash memory chip 429, or electrically erasable programmable read-only memory device, for storing information, such as information regarding the type of medicament, dosage, and its use with the device 410. An optional selection switch or lock switch 422 of circuit board 426 is exposed through switch window 430 of the first half housing 424. As will next be described, the circuit board 426 also includes the vapor element 420 that produces a condensation aerosol, and whose activities are regulated by microcontroller chips 428 and/or 438 of FIG. 11. Microcontroller chips 428 and/or 438 can activate one or more components of the vapor element 420, either simultaneously, or sequentially, to release one or more dosages or dosage amounts. Microcontroller chips 428 and/or 438 may also regulate/adjust heating temperatures, power, and duration of heating, period, of the vapor element 420 components. Flash memory chips 429 and/or 439 of FIG. 11 can be used for storing information, such as dosage counting, time/date memory, dosage usage history, serial number and medicament information, and a password to lockout unauthorized users. Furthermore, the flash memory chips 429 and/or 439 may be preprogrammed and/or reprogrammed with instructions specific for the type of medicament, so the microcontroller chips 428 and/or 438 can regulate vapor element 420 components according to the proper delivery characteristics of that particular medicament, or remaining dosages thereof, including proper vaporization settlings, such as temperature and duration, and perhaps even in accordance with the proper and/or selected airflow settings of the device 410.

In this embodiment, the vapor element 420 comprises one or more electrically resistive heating supports, such as metal foil supports, or other means of conductive support, used to vaporize a substance to produce a condensation aerosol for inhalation. There exist numerous methods to apply the medicinal substance to the vapor element 420. For instance, the substance may be placed on, over, or in close proximity to the vapor element 420, such as in the format of a thin film. Such may be the case when the medicament cartridge 411 is reusable. If the medicament cartridge 411 is disposable, the substance may be coated, inkjet, printed, brushed on, or dried, using an evaporable solvent, on the vapor element 420 directly, such as directly on its electrically resistive heating supports. The therapeutic application may consist of one or more different substances, dosage levels, and/or dosages. Therefore, the types of substances, dosages, and methods of applying the medicament to the vapor element 420, and the actual vapor element 420 itself, including its material of construction, surface area, shape, thickness, thermal mass, and electrical properties, etc., are not intended to be limited in the scope of this disclosure. Other embodiments may be envisioned by which the vapor element 420 may also serve as an electrostatic charger able to produce an electrostatic charge in the substance, or particles thereof.

Another component of vapor element 420, and its associated circuit board 426, are one or more spaces, holes, or vents 431 that allow air and/or vapor and/or aerosol to pass through so as to better suspend and entrain the substance particles in air, and to allow airflow to move the particles away from the vapor element 420, thereby, reducing subsequent deposition of such particles on the vapor element 420. Each half housing 424 and 425 of the medicament cartridge housing 412 has a vapor element window 432 and 433, which can expose the vapor element 420, and/or its vents 431, and/or its released vapor, to airflow in device 410. Airflow passing through the medicament cartridge 411 is depicted by a series of vertical arrows in FIGS. 10 and 11, while airflow passing over and under the medicament cartridge 411 are depicted as a series of diagonal arrows in FIGS. 10 and 11.

When the vapor element 420, and/or microcontroller chip 428, is activated by user input, such as from the detection of inhalation by an airflow sensor 436, one or more components of the vapor element 420 rapidly heats, vaporizes, one or more substances into the gaseous phase. Airflow, such as generated from user inhalation, passes over, around, and/or through the medicament cartridge 411 to entrain and cool the vaporized substance into a condensation aerosol with a MMAD desirable for inhalation, such as for lower airway and/or deep lung aerosol delivery. The condensation aerosol is carried to the user by airflow traveling through the inhaler device 410.

The inhaler device 410 may also have one or more airflow resistance control elements, which may be used to increase, maintain, and/or decrease airflow velocity and/or volume, and/or to keep the airflow velocity and/or volume within one or more desired ranges. As an example, slowing airflow velocity through the device 410 can allow for the user to take a prolonged breath in, over several seconds, for sustained maximal inspiration, inhalation, while a series of heating elements are sequentially activated to vaporize and produce a condensation aerosol, rather continuously, over much of this same extended time course. Such a means of controlling airflow velocity, and/or while controlling aerosol generation, may enhance aerosol delivery efficiencies.

Turning to FIG. 11, one can see that the device 410 can also have a circuit board 434, such as a printed circuit board or printed circuit assembly. The circuit board 434 contains a medicament card interface port or reader 435, which slidably receives the, asymmetrically shaped, medicament cartridge 411, and contains electrical contact pins to communicate with the electrical contact pins 421 of the medicament cartridge 411. The medicament card reader 435 can transfer electrical signals, data and/or power, to and from the medicament cartridge 411. Circuit board 434 may also contain a user input to activate the device 410, such as an airflow sensor 436 to activate the device 410 when inhalation is detected, a LED indicator light 437 to signal when data is being transferred, or when the device 410 is ready for use or is in use, a controller device or chip 438 that controls the activities of the circuit board 434, a flash memory chip 439, or electrically erasable programmable read-only memory device, for data storage and/or programming, and a crystal oscillator 440 that serves as an internal clock and may control data output. USB port or connector 419 is also on the circuit board 434 to receive power, and/or transfer data between an external device, such as a computer or smart phone, and the aerosol delivery device 410 with medicament cartridge 411. The aerosol delivery device 410 may also have its own power source, such as a rechargeable battery, not shown, which can receive current from an external device.

Lastly, this embodiment includes one or more airflow conduits 441 whereby aerosol is carried through the device 410 and out to the user through outlet 415. The airflow conduit 441 may shield some of the electronic components of the device 410 from the deposition of aerosols. The airflow conduit 441 may be made of anti-static materials, or have an anti-static coating, so that the conduit, itself, does not readily experience aerosol deposition. In other embodiments, this airflow conduit 441 may be much more elaborate and serve additional purposes. For instance, in another embodiment, this airflow conduit 441 is connected to the circuit board 434 where it can receive energy to produce an electromagnetic force/field which may help repel aerosol particles from the conduit's 441 walls, and/or may help control the velocity of or help move these aerosol particles through the device 410. Such a conduit may be ideal for delivering magnetically responsive nanoparticle aerosols, called nanomagnetosols. Nanomagnetosols have the potential for the enhanced targeting of aerosols to specific regions of the lungs when external magnets are used on the patient's chest.

As to the manner of usage and operation of the present disclosure, the same should be apparent from the above description. Accordingly, no further discussion relating to the manner of usage and operation will be provided.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

FIGS. 12-19 show an exemplary jet nebulizer (nebulizer 1100) in accordance with an embodiment of the present disclosure. The exemplary jet nebulizer includes a dialable negative pressure threshold valve whereby actuation of this valve, at any of the different negative pressure threshold settings, is associated with allowing ambient air to enter through the nebulizer, preferably as the valve includes at least one ambient air inlet of the nebulizer, for enhanced aerosol entrainment and delivery.

Figures 12, 13:
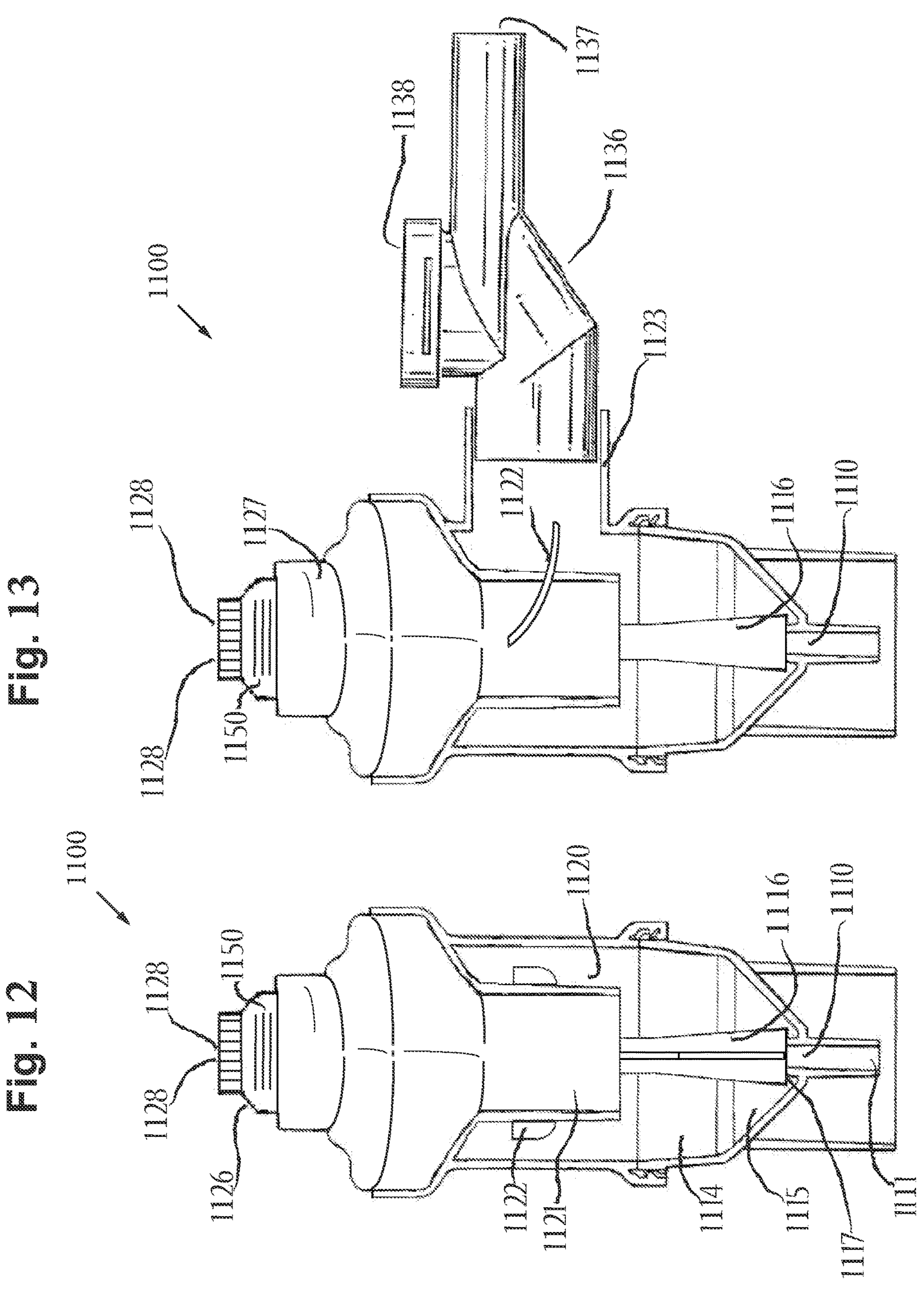
FIG. 12 includes a back view of a nebulizer, in accordance with an embodiment of the disclosure.
FIG. 13 includes a side view of the nebulizer of FIG. 12 shown with a valve in a non-actuated state, in accordance with an embodiment of the disclosure.
Figures 14, 15:
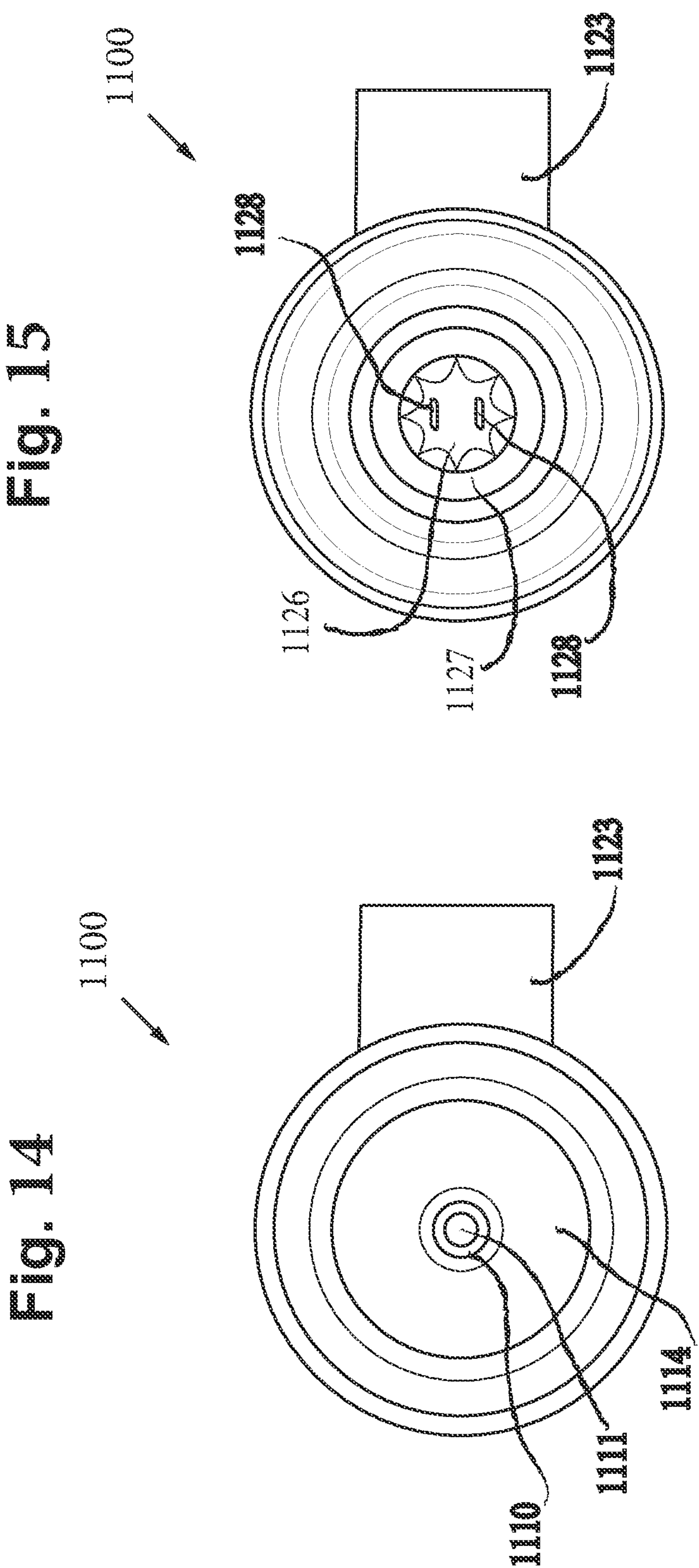
FIG. 14 includes a bottom-up view of the nebulizer of FIG. 12, in accordance with an embodiment of the disclosure.
FIG. 15 includes a top down view of the nebulizer of FIG. 12, in accordance with an embodiment of the disclosure.
Figure 16:
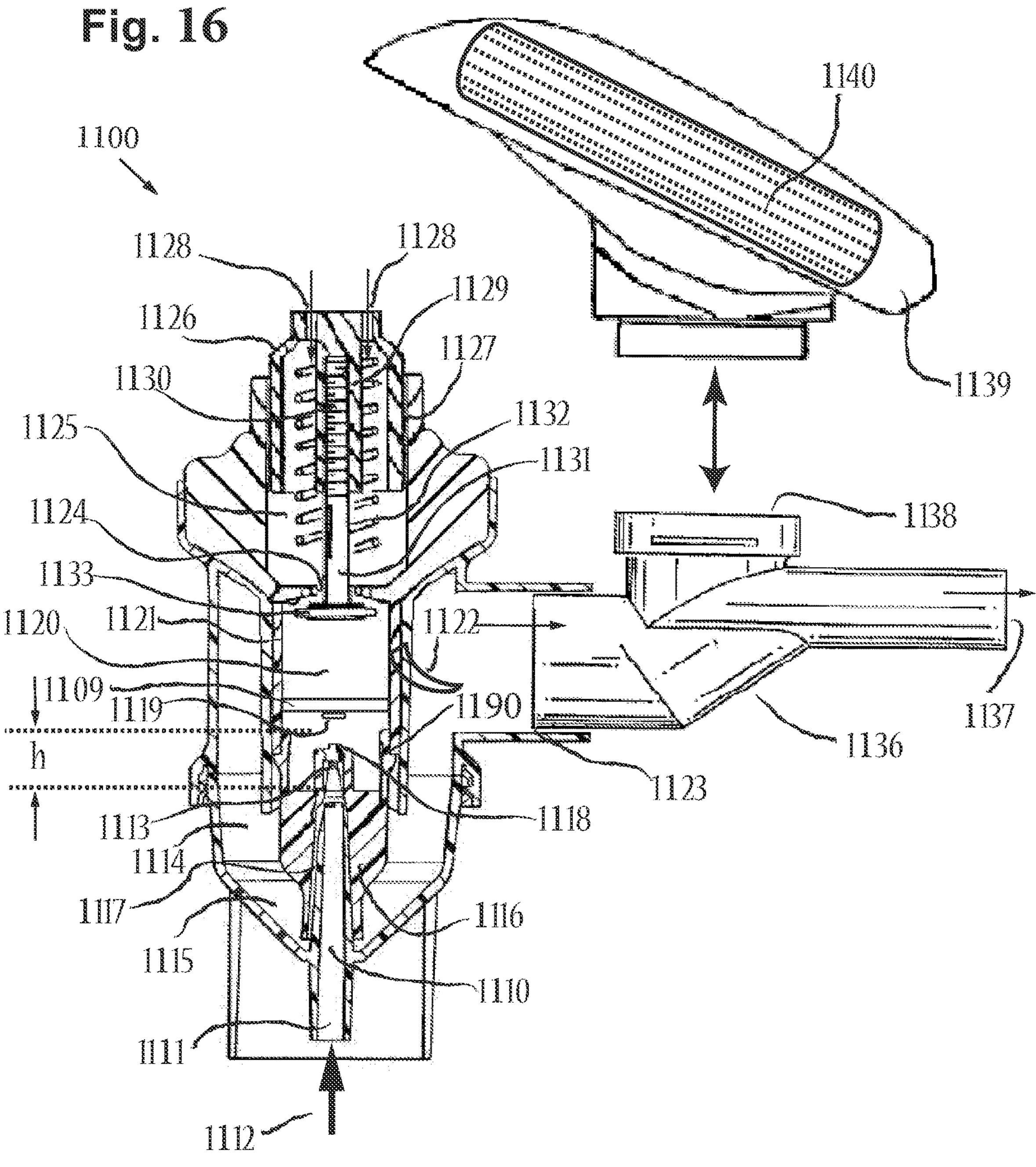
FIG. 16 includes a cross-sectional side view of the nebulizer shown in a non-actuated state, in accordance with an embodiment of the disclosure.
Figure 17:
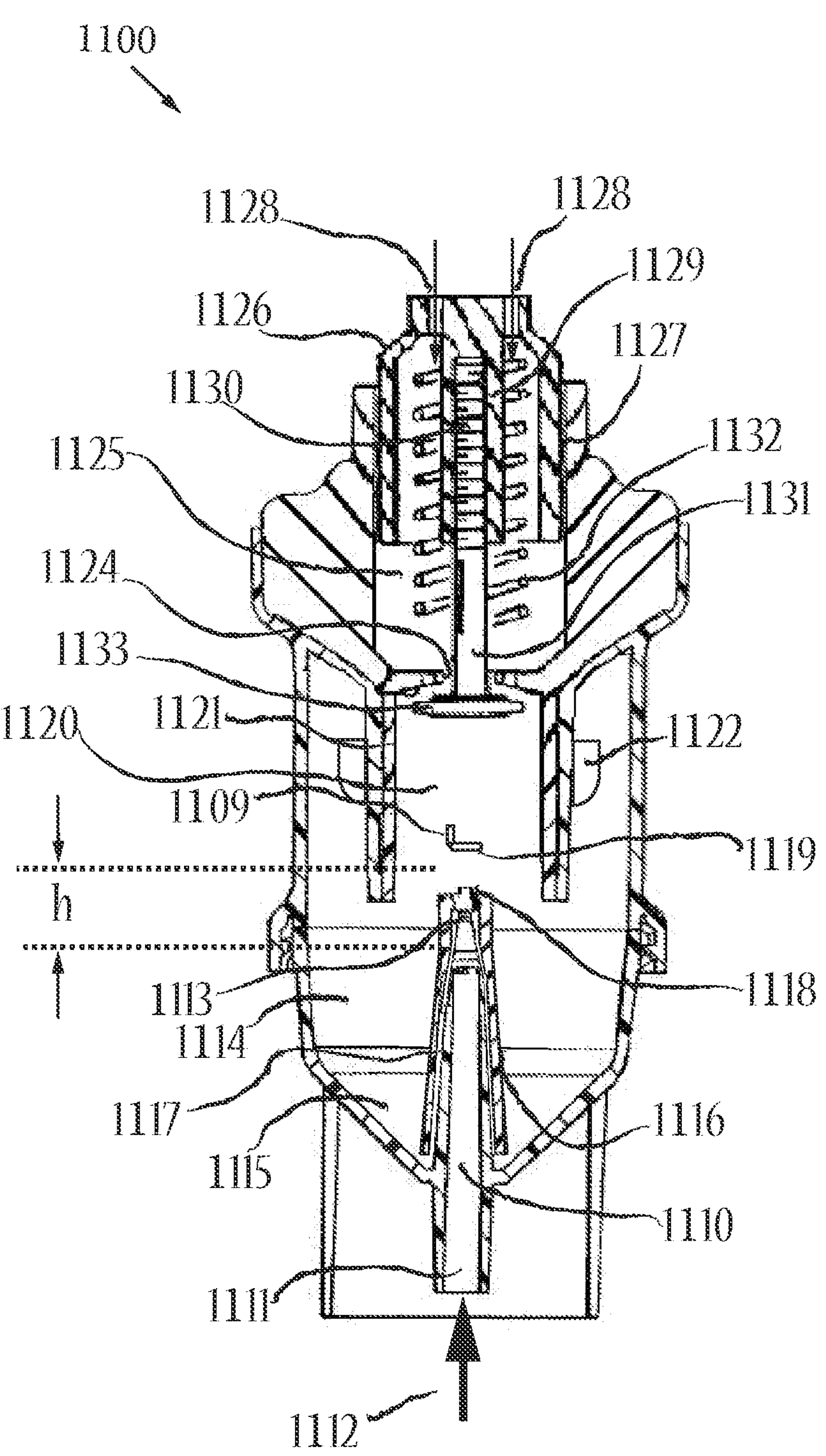
FIG. 17 includes a cross-sectional back view of the nebulizer of FIG. 12, in accordance with an embodiment of the disclosure.

FIG. 12 includes a back view of the nebulizer 1100, in accordance with an embodiment of the disclosure. FIG. 13 includes a side view of the nebulizer 1100 of FIG. 12 shown with a valve in a non-actuated state, in accordance with an embodiment of the disclosure. FIG. 14 includes a bottom-up view of the nebulizer 1100 of FIG. 12, in accordance with an embodiment of the disclosure. FIG. 15 includes a top down view of the nebulizer 1100 of FIG. 12, in accordance with an embodiment of the disclosure. FIG. 16 includes a cross-sectional side view of the nebulizer 1100 shown in a non-actuated state, in accordance with an embodiment of the disclosure. FIG. 17 includes a cross-sectional back view of the nebulizer 1100 of FIG. 12, in accordance with an embodiment of the disclosure.

Referring now to FIG. 16 and FIG. 17, this exemplary jet nebulizer 1100 is shown including a jet nozzle 1110 able to receive compressed air and/or compressed oxygen from compressed gas inlet 1111 connected to a source of compressed gas 1112. Sources of compressed gas 1112 can may include air pumps, portable air compressors, oxygen concentrators, or pressurized medical gas tanks. When the nebulizer 1100 embodiment serves as a disposable nebulizer, oxygen tubing, not shown, connects gas inlet 1111 to sources of compressed gas 1112. A gas flowmeter may also be connected in this gas circuit. When the nebulizer 1100 embodiment serves as a hand-held, non-disposable nebulizer, the source of compressed gas 1112 may even be a component of the nebulizer 1100 itself when the source of compressed gas 1112 is a built-in miniature, battery powered, air compressor.

Jet nozzle 1110 includes a tapered air outlet 1113 at the top of its conical tip pointing upward. A portion of the jet nozzle 1110 resides inside of a liquid reservoir container 1114, defining an inner space adapted to receive a liquid therein and filled with a liquid medicament formulation 1115. The reservoir container 1114 is connected detachably and securely to the main device housing. A jacket 1116 is circumferentially sleeved around the jet nozzle to define a fluid-introducing gap 1117 there between. The exterior surface of the jet nozzle 1110 or the interior surface of the jacket 1116 can be smooth, irregular, or grooved. When assembled, this jacket 1116 is preferably fixedly positioned over the jet nozzle 1110 and does not move so that the fluid-introducing gap is held constant. At the top of the tip of the jacket 11116 is at least one restricted opening 1118, which faces upward and is aligned with the nozzle air outlet 1113. When in use, a high-pressure air jet passes through the jet nozzle 1110, from its gas inlet 1111 and out through its tapered air outlet 1113, and out through restricted opening 1118 of the jacket tip. As liquid from the fluid-introducing gap 1117 is brought into the jet, high-pressure air atomizes the liquid as the liquid leaves the restricted opening 1118 of the jacket 1116 tip.

Many of the particles produced are coarse droplets above 15 micrometers in size. Because aerosol particles of a MMAD of under 5 micrometers, and preferably under 2 micrometers, are more desirable for inhalation, an impact baffle 1119 can be placed above the jacket 1116. Large particles collide with the impact baffle, causing them to condense into liquid and return to the liquid reservoir container 1114, so that only smaller sized aerosol particles are available for inhalation. Baffling also affects how much aerosol is released rather than returned to the liquid reservoir container 1114, and thus affects efficiency of the nebulizer. The size and position of the impact baffle 1119 is chosen for the desired particle size and quantity of aerosol bolus desired. Impact baffle 1119 is shown held permanently in place a certain distance above the jet nozzle 1110 by a horizontal structural beam 109 that is attached to the walls of a conical section or chimney 1121 contained in the interior nebulization chamber 1120. Chimney 1121 is a mist discharging conduit that extends downward and is in fluid communication with the inner space for passage of a mist there through and aligned with the jacket 1116 in a jet-ejecting direction. Jacket 1116 may be adjoined to chimney 1121 by a joint region 1190. Extension guides 1122 may protrude from the walls of the chimney 1121. Chimney 1121 and its extension guides 1122 also prevent undesirable, larger droplets from exiting the device, and instead, cause such droplets to condense and return to the liquid containing reservoir 1114. In this manner, smaller particles with a MMAD ideal for inhalation are able to freely exit the device through aerosol air outlet port 1123. Furthermore, chimney 1121 and its extension guides 1122 cause ambient air entering the device to take a more tortuous flow path through the device to ensure that an adequate amount of aerosol is entrained in this airflow to reduce particle size and/or to prevent particles from colliding and growing. Extension guides 1122 of the chimney 1121, or other baffles residing in the device, may be curved or spiral-shaped to cause cyclonic action of aerosol entrained airflow.

Ambient air enters interior chamber 1120 through a Venturi-like central aperture 124 located at the top of chimney 1121. Airflow through this central aperture 1124 is regulated by a negative pressure threshold valve assembly 1125. The negative pressure threshold valve assembly 1125 is comprised of a rotatable cap 1126 with an integrally formed cylindrical wall slidably received through the cylindrical upper region of the device housing 1127. One or more ambient air inlets 1128 are found at the top of rotatable cap 1126. The rotatable cap 1126 also has a tubular guide 1129 extending through a portion of it. The tubular guide 1129 has female threads 1130 designed to receive the male threads of a thin rod 1131. A load calibrated, coiled spring 1132, or other resilient biasing member, is positioned inside of the rotatable cap 1126, around the tubular guide 1129 and thin rod 1131. A circular disc 1133, along thin rod 1131, is located within the interior chamber 1120 of the device, and together circular disc 1133 and thin rod 1131 comprise the actuator piston of negative pressure threshold valve assembly 1125. As the spring 1132 biasing member puts upward pressure on rotatable cap 1126, circular disc 1133 is pulled against the top surface of inner chamber 1120, or chimney 1121, and thus, blocks central aperture 1124. The blocking of ambient air into the interior nebulization chamber 1120 allows significant negative pressure to efficiently be reached prior to actuation.

Figures 18, 19:
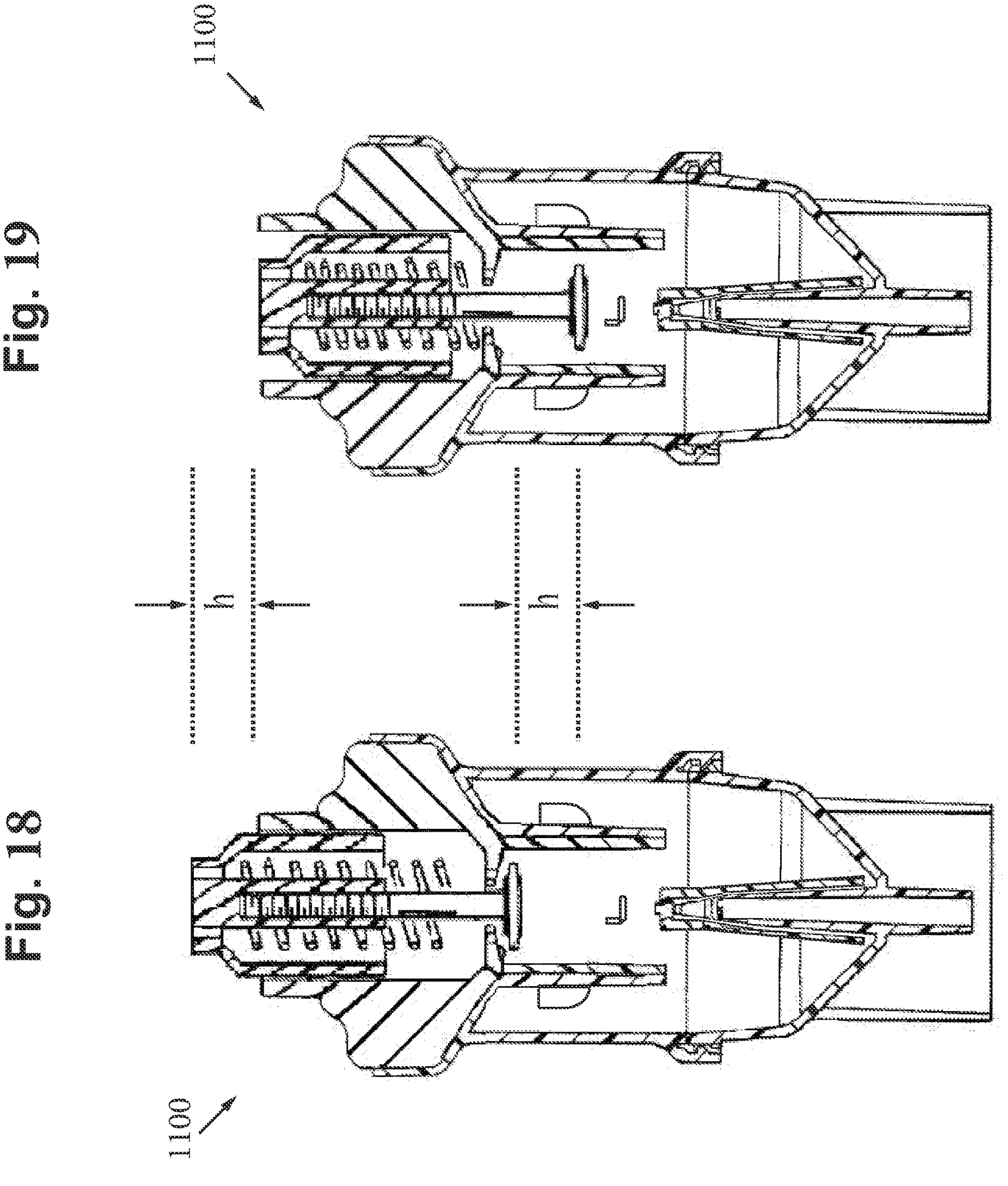
FIG. 18 includes a cross-sectional back view of the nebulizer of FIG. 16 depicting the adjustable negative pressure threshold in a non-actuated state while nebulization is continuously generated, in accordance with an embodiment of the disclosure.
FIG. 19 includes a cross-sectional back view of the nebulizer of FIG. 16 depicting the adjustable negative pressure threshold valve in a fully actuated state, in accordance with an embodiment of the disclosure.

FIG. 18 includes a cross-sectional back view of the nebulizer 1100 of FIG. 16 depicting the adjustable negative pressure threshold in a non-actuated state while nebulization is continuously generated, in accordance with an embodiment of the disclosure. FIG. 19 includes a cross-sectional back view of the nebulizer 1100 of FIG. 16 depicting the adjustable negative pressure threshold valve in a fully actuated state, in accordance with an embodiment of the disclosure. The entire jacket 1116 is comprised of a single piece and always remains fixed in position over the jet nozzle 1110 whether the valve is actuated or not. During inhalation, when the negative pressure inside the nebulizer 1100, distributed over the bottom surface of circular disc 1133 of the actuator piston of the negative pressure threshold valve assembly 1125, exceeds the biasing member force or spring force of coiled spring 1132, the negative pressure threshold valve assembly 1125 will actuate as the spring 1132 compresses and the actuator piston moves down. If pressurized air is being supplied to the nebulizer 1100 via compressed gas inlet 1111, then in order to generate sufficient negative pressure within the nebulizer, the rate of airflow exiting the nebulizer 1100 should generally exceed the pressurized gas flow rate entering the nebulizer chamber.

When the valve is actuated, ambient air enters the device through ambient air inlets 1128, entrains nebulized particles, and carries these particles out of the device through aerosol air outlet port 1123. Although actuation of the negative pressure threshold valve assembly 1125 in this current configuration does not influence the generation of nebulized particles, actuation does influence entrainment of these particles so that the jet nebulizer 1100 serves as a breath actuated aerosol entrainment device, which is different from breath actuated nebulization. Referring to FIGS. 12-13, calibrating indicia 1150 are provided on the exterior cylindrical walls of rotatable cap 1126, so that negative pressure threshold valve assembly 1125 also serves as a calibrated pressure threshold control element having different settings. The adjustable negative pressure threshold valve includes a plurality of negative pressure settings of actuation. The different negative pressure threshold settings of actuation are preferably incremental, although the differences in negative pressure among the settings can also be exponential instead of linear, or a combination of exponential and linear differences among the settings. Serving as a dialable user interface or dial, the rotatable cap 1126 preferably has grooves or ridges on its exterior surface, as shown in FIG. 15, for easy gripping and turning with a patient's fingers. Referring to FIG. 16, as the rotatable cap 1126 is rotated as a dial to a different setting, the distance that the thin rod 1131 screws into the tubular guide 1129 of the rotatable cap 1126 also changes, thereby affecting the space between the rotatable cap 1126 and the central aperture 1124 of the device housing 1127, and thus changing the compression of the spring 1132 and changing the biasing member force of this biasing member. By varying the tension of the spring 1132, one can control the negative pressure threshold required for actuation of this dialable negative pressure threshold valve. Negative pressure actuation thresholds above 1 centimeter of water, and preferably above 3 centimeters of water, can be achieved by changing to increasingly greater negative pressure threshold settings of the dialable valve. Negative pressure threshold settings of actuation could conceivably range past 10 centimeters of water, range past 20 centimeters of water, range past 50 centimeters of water, or even range past 100 centimeters of water, and upper range examples are not meant to be limiting. In other words, the upper range limit can be well under a negative pressure threshold that is humanly impossible to reach or at a negative pressure threshold that is humanly impossible to reach.

Preferably, it is desirable to maintain the negative pressure threshold valve assembly 1125 in its actuated state throughout most of inhalation. This would require the patient to provide a sustained negative pressure equal to or above the threshold required by the negative pressure threshold setting of the negative pressure threshold valve assembly 1125. The maintaining of a sustained negative pressure over time can provide for a sustained maximal inhalation.

Expansion of the lungs is what generates negative pressure associated with inhalation. In order for a patient to generate a sufficient negative pressure needed for actuation and sustained actuation of a difficult threshold setting, the muscles involved in respiration, including the diaphragm, must contract strong enough to enlarge the thoracic cavity, and expand the lungs, sufficiently enough and for as long as possible. Any resistance associated with a negative pressure threshold that requires an increased inhalation effort from the patient is also a resistance to the contraction of the muscles involved in respiration in expanding the lungs. This is a significant physiological effect because it can be detected and experienced by the patient.

It can be appreciated that in certain circumstances, increased negative pressure thresholds can provide desirable therapeutic benefits. For instance, higher negative pressure thresholds, thresholds above 3.0 cm of water, require an increased inhalation effort with greater exertion of the muscles involved in respiration. These higher negative pressure thresholds, as experienced by the patient, can exercise the respiratory muscles beyond what normal breathing can do. Such higher negative pressure thresholds can be used for strength training of the muscles involved in respiration, but can also be used to help maintain lung elasticity and improve respiratory health. A nebulizer of the present disclosure having these different negative pressure threshold settings could be used by chest surgery patients, instead of an incentive spirometer, to help remove secretions and prevent atelectasis on the day of their operation. Such a stand-alone nebulizer device has the potential to reduce overall hospital costs, while saving time and providing greater convenience. The present disclosure discloses a stand-alone nebulizer that can provide effective negative pressure threshold resistance training that can be performed before, after, or simultaneously with nebulized aerosol delivery. Clear and expanded lungs and airways are also more receptive to receiving delivered aerosol. The present disclosure departs from the usual doctrines of effortless aerosol treatments to demand substantially more inhalation effort from the patient.

Referring to FIG. 16 again, a user mouthpiece 1136 attaches to device outlet, aerosol air outlet port 1123. Various nebulizer mouthpieces have been described in the art. Airflow passes through the mouthpiece 1136 and out through its outlet 1137. Said mouthpiece 1136 may contain an exhaust port 1138, containing an elastomeric one-way, flap, valve, which vents user exhalation, but does not open during user inhalation. Therefore the one-way flap valve does not have any influence on the negative pressure of the nebulizer during inhalation or on the patient's ability to generate negative pressure during inhalation. An optional and/or removable filter housing assembly 1139 may be aligned with exhaust port 1138, to allow exhaled air to pass through a filter element 1140, and out of the filter housing 1139. A preferred filter element 1140 may be a 3M® filtrate filter, or other HEPA filter able to capture infectious particles and aerosol particles larger than 0.3 micrometers in diameter from exhalation, thereby preventing cross contamination to nearby individuals. A contaminated filter element may be cleaned or replaced as necessary.

The exemplary jet nebulizer according to the present disclosure has a variable negative pressure threshold valve that actuates in response to different negative pressures corresponding to different negative pressure threshold settings of actuation. The negative pressure threshold valve is adjustable and includes a biasing member component of the valve, the valve further including settings that change the negative pressure thresholds of actuation of the valve by changing the biasing member force of the biasing member component of the valve. The valve is able to influence nebulized aerosol delivery and allow ambient air to enter and entrain aerosol particles.

This exemplary nebulizer can include additional components or modifications so that the efficiency of nebulization can be adjusted. For example, FIGS. 16-19 show the impact baffle 1119 held in a fixed position above the jet nozzle 1110 by horizontal support beam 1109. If the horizontal support beam 1109 was located higher in the chimney, the impact baffle 1119 would be a further distance from the jet nozzle 1110. Adjustments in baffling can affect the ratio of large to small aerosol particles generated and released, also having effects on aerosol bolus size and nebulizer efficiency.

The horizontal support beam 1109 could also serve the purpose of an obstruction to limit how far down the actuator piston (e.g., disc 1133 and rod 1131) moves down when actuated. In other examples, instead of there being a horizontal support beam 1109, the impact baffle 1119 could instead be attached to the bottom of circular disc 1133 or some other structure emanating from rod 1131, so that the impact baffle 1119 is variably positioned above the jet nozzle 1110 in association with movement of the actuator piston. Such an example can allow for a continuous, but non-constant, aerosol output, so that aerosol bolus size changes throughout the inhalation cycle. In other examples, the impact baffle 1119 may not be present, or circular disc 1133 can also serve the function of an impact baffle 1119. These other examples of variable impact baffles are not shown, but may be implemented. Also, these examples are not meant to be limiting.

FIGS. 12-19 show the exemplary nebulizer 1100 as a jet nebulizer that continuously nebulizes as long as pressurized gas is being supplied to jet nozzle inlet 1111, and as long as the liquid reservoir container 1114 is filled with a liquid medicament 1115. Additional components and modifications of this exemplary nebulizer 1100 can be included so that nebulization is not continuous.

FIGS. 20-25 show another exemplary aspect of the jet nebulizer (nebulizer 1101) according to the present disclosure that is modified and includes a dialable negative pressure threshold valve whereby actuation of this valve, at any of the different negative pressure threshold settings, is also associated with actuation of nebulization so that nebulization is coordinated with the patient's breathing cycle. Nebulization is thus non-continuous and breath activated in this modified nebulizer that serves as a breath actuated nebulization device.

Figures 20, 21:
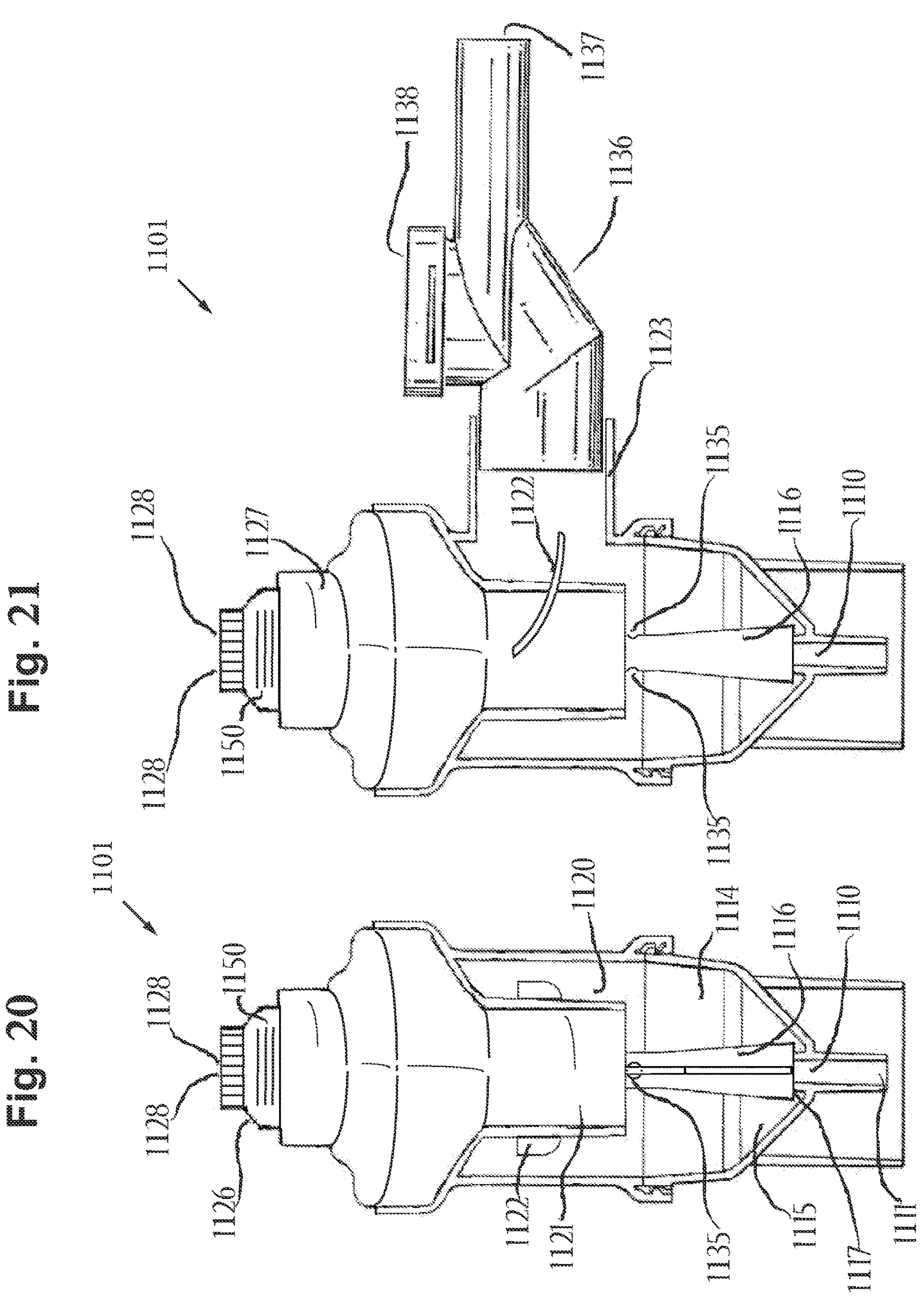
FIG. 20 includes a back view of a nebulizer in a non-actuated state, which is capable of non-continuous, breath activated nebulization coordinated with the patient's breathing cycle, in accordance with an embodiment of the disclosure.
FIG. 21 includes a side view of the nebulizer of FIG. 20, in accordance with an embodiment of the disclosure.
Figure 22:
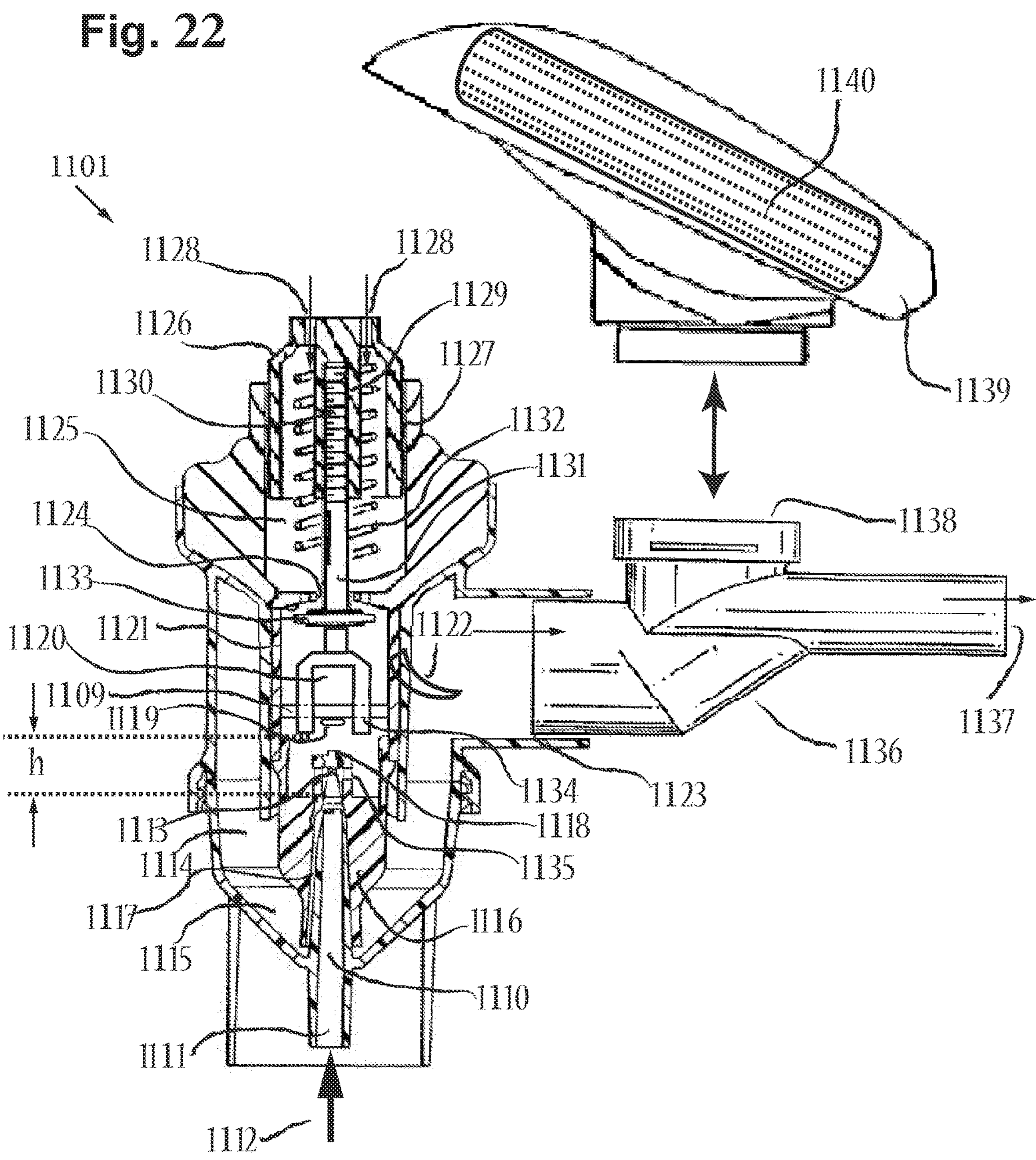
FIG. 22 includes a cross-sectional side view of the nebulizer of FIG. 20, in accordance with an embodiment of the disclosure.
Figure 23:
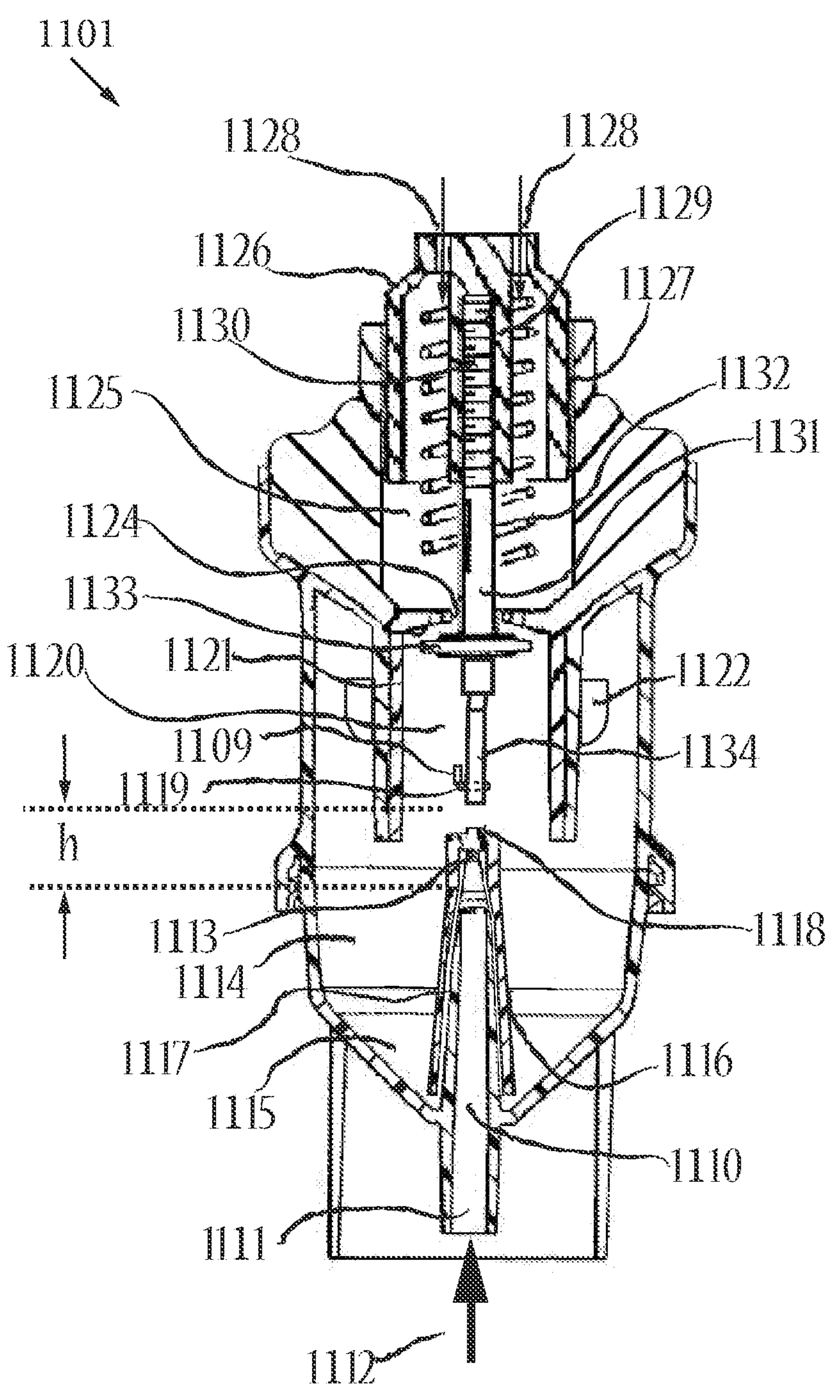
FIG. 23 includes a cross-sectional back view of the nebulizer of FIG. 20, in accordance with an embodiment of the disclosure.
Figures 24, 25:
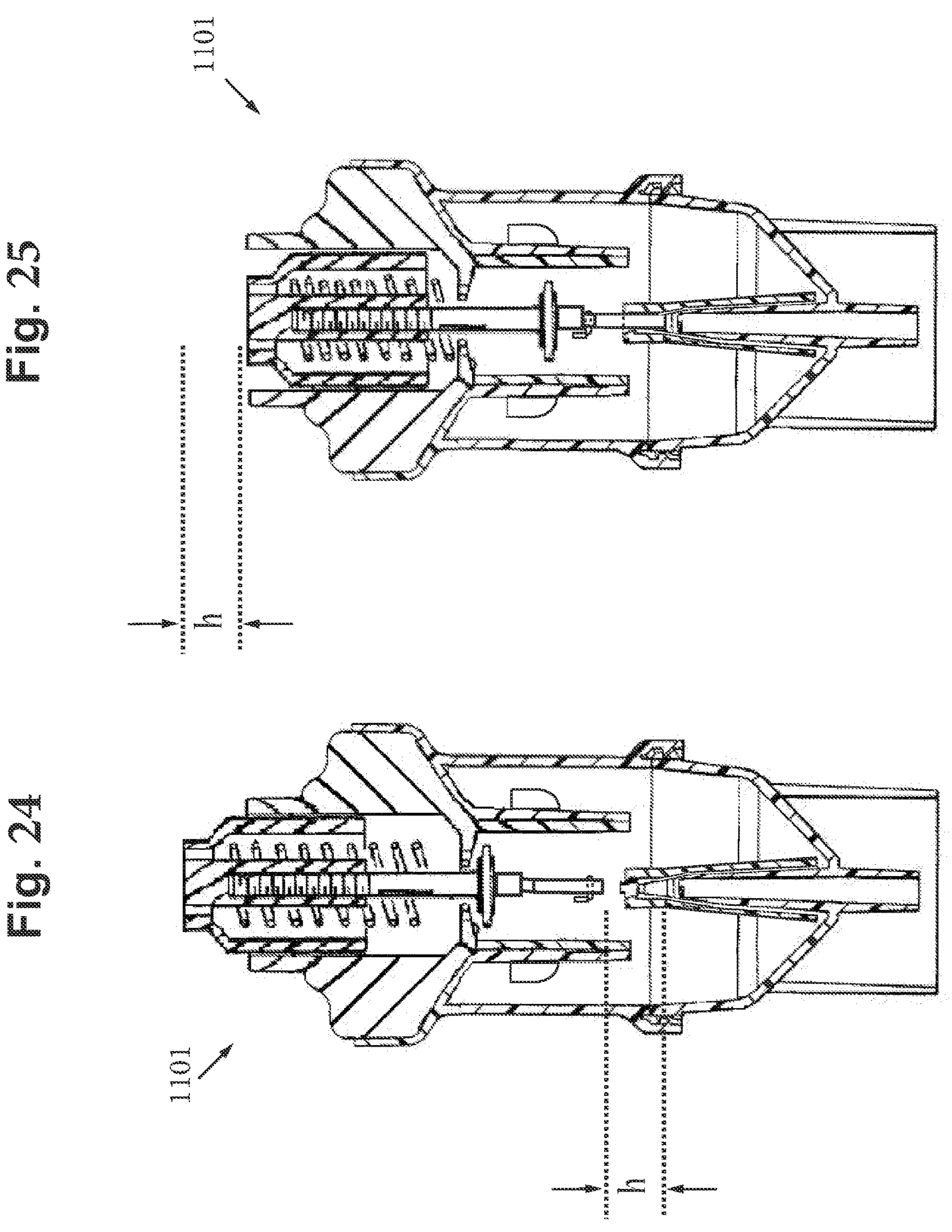
FIG. 24 includes a cross-sectional back view of the nebulizer of FIG. 20 depicting the adjustable negative pressure threshold valve, in accordance with an embodiment of the disclosure.
FIG. 25 includes a cross-sectional back view of the nebulizer of FIG. 20 depicting the adjustable negative pressure threshold valve, in accordance with an embodiment of the disclosure.

FIG. 20 includes a back view of a nebulizer 1101 in a non-actuated state, which is capable of non-continuous, breath activated nebulization coordinated with the patient's breathing cycle, in accordance with an embodiment of the disclosure. FIG. 21 includes a side view of the nebulizer 1101 of FIG. 20, in accordance with an embodiment of the disclosure. FIG. 22 includes a cross-sectional side view of the nebulizer 1101 of FIG. 20, in accordance with an embodiment of the disclosure. FIG. 23 includes a cross-sectional back view of the nebulizer 1101 of FIG. 20, in accordance with an embodiment of the disclosure. FIG. 24 includes a cross-sectional back view of the nebulizer 1101 of FIG. 20 depicting the adjustable negative pressure threshold valve, in accordance with an embodiment of the disclosure. FIG. 25 includes a cross-sectional back view of the nebulizer 1101 of FIG. 20 depicting the adjustable negative pressure threshold valve, in accordance with an embodiment of the disclosure.

Referring now to FIGS. 20-21, this exemplary jet nebulizer 1101 is shown modified by including one to two small jacket holes 1135, at the tip of the jacket 1116 adjacent to the restricted opening 1118. Small jacket hole 1135 is directly visible in the back view of the nebulizer in FIG. 20, although a joint that fuses the jacket 1116 to the chimney 1121 structure is shown in front of a portion of this hole 1135. The side view of FIG. 21 shows the profile of the at most two small jacket holes 1135. No aerosol is generated from restricted opening 1118 when the small jacket hole 1135 is free from obstruction. Restricted opening 1118 is not visible in FIGS. 20-21.

Referring now to the FIG. 22 and FIG. 23, this exemplary jet nebulizer 1101 is shown with an accompanying modification of including a movable and preferably horseshoe-shaped seal 1134 that is attached to the bottom of the actuator piston. More specifically, the moveable seal 1134 is attached under the circular disc 1133, and preferably attached to the end of thin rod 1131, a portion of the rod which extends past circular disc 1133.

The entire jet nozzle 1110 is in a fixed position in the nebulizer housing. The entire jacket 1116 is comprised of a single piece and is fixedly positioned over the jet nozzle 1110 and does not move so that the fluid-introducing gap 1117 is held constant. Only the horseshoe-shaped seal 1134 is moveable to flank the small jacket hole 1135 of the non-moveable jacket 1116. The horseshoe-shaped seal 1134 is not a component or portion of the nozzle jacket.

Referring now to FIGS. 24-25, upon a threshold level of negative pressure achieved by inhalation, the actuator piston of negative pressure threshold valve assembly 1125 moves downward by a distance 'h', thereby, placing horseshoe-shaped seal 1134 into a position that permits nebulization. Nebulization occurs when horseshoe-shaped seal 1134 flanks small jacket hole 1135 and obstructs it, so that aerosol is generated from restricted opening 1118.

When negative pressure from inhalation decreases and can no longer hold the valve open, such as towards the end of inhalation, the valve closes, the piston moves upward, and the moveable seal 1134 is no longer in a position that allows nebulization. In this manner, nebulization only takes place when the user is able to inhale through this device and generate a negative pressure at least as great as the threshold required for actuation. Downward movement of the cap 1126 may also signal that inhalation and nebulization are taking place.

Figures 26, 27:
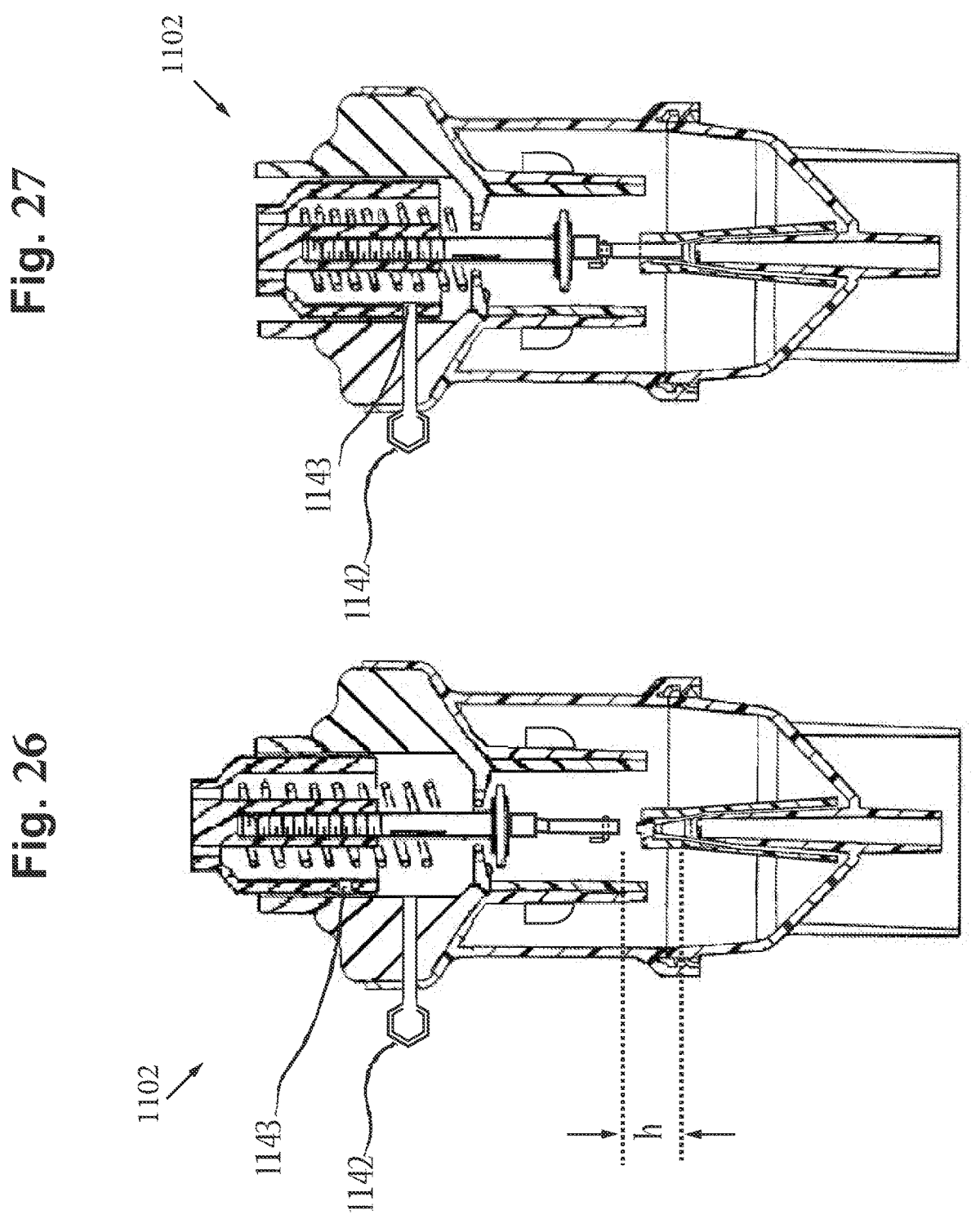

The negative pressure threshold valve assembly 1125 is capable of being bypassed when no actuation threshold is desired. For example, cap 1126 may be unscrewed and removed from the rod 1131, or manually pushed down and twisted to a locking position, which allows for continuous nebulization. Referring now to FIGS. 26-27, a still further modification to the exemplary embodiment of the disclosure is shown. FIG. 26 includes a cross-sectional back view of a nebulizer 1102 that includes a valve bypass lock pin and dial lock pin port, in accordance with an embodiment of the disclosure. FIG. 27 includes a cross-sectional back view of the nebulizer 1102 of FIG. 26, in accordance with an embodiment of the disclosure. As shown in FIGS. 26-27, the exemplary embodiment includes a valve bypass lock pin 1142 and dial lock pin port 1143. The valve bypass lock pin 1142 is slidably received horizontally through the upper housing of the device. Rotatable cap 1126 is modified with at least one dial lock pin port 1143 on its corresponding side or sides. When the rotatable cap 1126 is moved downward a distance of 'h' either manually by hand or by breath actuation of the valve, the lock pin 1142 is correctly aligned to be pushed in and slidably received by the lock pin port 1143. The valve is bypassed and held open so that no negative pressure threshold exists until the lock pin 1142 is pulled back out to the unlocked position.

The jet nebulizer 1101 of FIGS. 20-25, and the jet nebulizer 1102 of FIGS. 26-27, according to the present disclosure have a variable negative pressure threshold valve that actuates in response to different negative pressures corresponding to different negative pressure threshold settings of actuation. The negative pressure threshold valve is adjustable and includes a biasing member component of the valve, the valve further including settings that change the negative pressure thresholds of actuation of the valve by changing the biasing member force of the biasing member component of the valve. The valve is able to influence nebulized aerosol delivery and allow ambient air to enter and entrain aerosol particles. In essence, the adjustable negative pressure threshold valve, which actuates in response to different negative pressures corresponding to different negative pressure threshold settings of actuation; is further structured to serve as a nebulization actuator so that nebulization is coordinated with the breathing cycle. More specifically, these modified nebulizers of the present disclosure have a dialable negative pressure threshold valve, the valve actuates in response to different negative pressures above 1 centimeter of water, and preferably above 3 centimeters of water, corresponding to different negative pressure threshold settings of actuation; the settings change the negative pressure thresholds of actuation of the valve by changing the biasing member force of a biasing member component of the valve when the orientation of a dialable component of the valve is changed; the valve further structured to serve as a nebulization actuator piston so that nebulization is coordinated with the breathing cycle.

Increased negative pressure threshold settings of this disclosure require an increased inhalation effort and can provide exercise to the muscles involved in respiration. The breathing exercise therapy provided by this nebulizer can also help maintain lung elasticity.

For patients with adequate lung function that can achieve greater inhalation effort, the different negative pressure threshold settings of this nebulizer can have profound effects on aerosol delivery dynamics. Aerosol generation and aerosol delivery occur when enough negative pressure builds within the device to cause actuation. After building up the necessary negative pressure required for valve actuation, aerosol is generated at the precise moment that the valve opens to allow a rapid stream of ambient air into the device for entraining and efficiently carrying out this aerosol as a bolus. Choosing different settings can allow this bolus to be sustained as a stream over different lengths of inhalation. Time corresponding to different negative pressures that can be sustained and selected by the patient. Moreover, by having actuation of nebulization and aerosol entrainment associated with different negative pressure threshold settings, this novel nebulizer can be used to selectively target aerosols to one or more different airway regions. In effect, aerosol actuation, entrainment, and delivery occur when one or more different airways are optimally expanded with the desired pressure for enhanced drug targeting and delivery efficiency. The nebulizer is thus adapted to selectively target aerosols to one or more different airway regions by selecting different negative pressure threshold settings of actuation of nebulization. The one or more different airway regions are chosen from the regions, including, but not limited to, the upper airways, upper respiratory tract, nasal cavity, pharynx, larynx, lower airways, lower respiratory tract, trachea, bronchi, lungs, bronchioles, deep lung, and alveoli where systemic exchange takes place.

Other embodiments of nebulizers within the scope of the present disclosure include motorized or electronic controlled adjustable negative pressure threshold valves of actuation, which employ the use of solenoid valves and pressure sensors and the necessary circuitry, buttons, and power elements to accomplish this. Other conceivable nebulizer embodiments can include handheld nebulizers that have their own built-in air compressors and power elements.

Further embodiments can include piezo-electric nebulizer generating means in addition to or instead of a jet nozzle.

Even further conceivable nebulizer embodiments can include a moveable seal that exists in a position that allows nebulization to occur until moved out of position by actuation of the valve during inhalation, so that nebulization does not occur during inhalation, but nebulization occurs during exhalation.

These other conceivable embodiments are not shown and are not meant to be limiting.

There are methods for using the nebulizers disclosed in the present disclosure, as well as, methods to produce the desired therapies and aerosol delivery dynamics when using the present disclosure.

Figure 28:
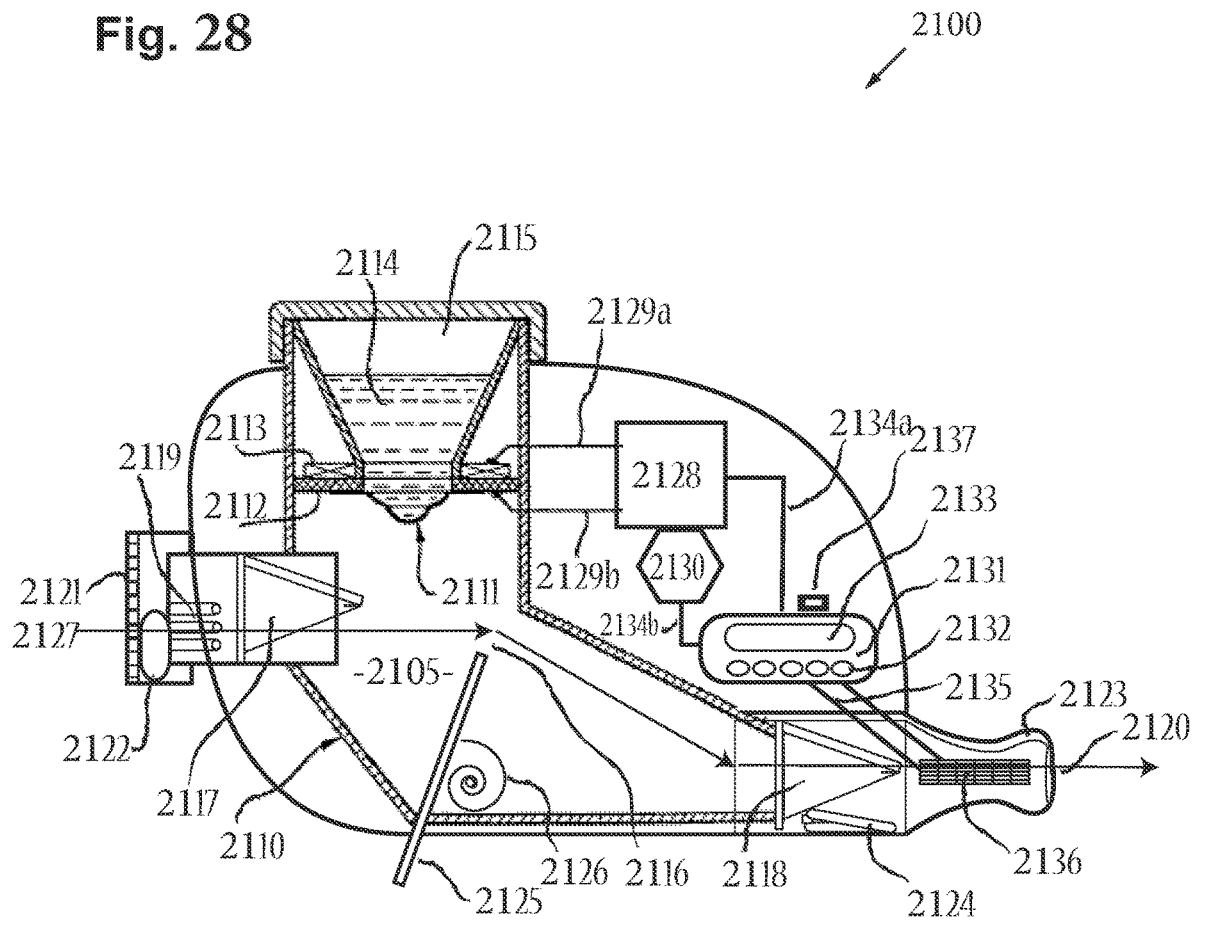

FIG. 28 includes a cross-sectional side view of an aerosol delivery device 2100, in accordance with an embodiment of the disclosure. The aerosol delivery device 2100 having a structure comprising a housing 2110, an at least one (ambient) air inlet 2119, an at least one aerosolized air outlet 2120, and an at least one airflow passage (extending) there between/therein 2116. The aerosol delivery device 2100 further comprises an at least one aerosol generating element (2111, 2112, 2113) producing an aerosol with the use of electrical energy and without the use of compressed/pressurized gas. The aerosol delivery device 2100 further has an at least one airflow 2127 through its housing 2110 produced by a user inhaling from this aerosol delivery device 2100 and entraining aerosol when generated. The at least one airflow 2127 is controllable in velocity, volume, or a combination thereof as the at least one air inlet 2119, the at least one aerosolized air outlet 2120, the at least one airflow passage 2116, or a combination thereof undergoes an at least one physical change selected from changes in size, angle, shape, biasing resistance to flow, number of apertures, shunting of airflows/airflow paths, or a combination thereof. This will be described later in further detail.

The at least one physical change is modulated by user/digital input to control the at least one airflow and or entrained aerosolized air and to regulate an at least one parameter selected from user inhalation resistance, user inhalation duration, user inhalation rate, aerosol delivery efficiency, targeting of aerosol to different user airway regions, or a combination thereof. In various embodiments, the aerosol delivery device 2100 has an adjustable airflow restriction of the at least one airflow through the housing 2110, and or an adjustable negative pressure through the housing 2110, experienced when the user inhales through the aerosol delivery device 2100.

The aerosol delivery device 2100 embodiment of FIG. 28 has an at least one aerosol generating element (2111, 2112, 2113), which includes a vibratable, porous membrane 2111 that is caused to oscillate at a desired frequency by piezoelectric motor assembly in response to an electric drive signal, as will later be explained. The piezoelectric motor assembly is comprised of a support unit 2112 and a piezo electrical conversion unit 2113, both containing or comprised of electrically conductive material. Both support unit 2112 and piezo electrical conversion unit 2113 are attached to each other, and both are attached to vibratable membrane 2111.

The oscillation of vibratable membrane 2111, which may include bending oscillations, causes a liquid aerosolizable substance or formulation 2114, stored within a liquid reservoir 2115, to be atomized/nebulized as this liquid 2114 is forced through small pores of membrane 2111. The formulation may be that of an active ingredient in liposomes. The resulting nebulized aerosol travels into, and diffuses within, the internal chamber or aerosol holding chamber 2105. Optionally or alternatively, a liquid containing-cartridge or vial can be placed within the liquid reservoir 2115 or take the place of or serve as the liquid reservoir 2115 (not shown).

One-way valves 2117 and 2118, preferably duckbill valves, trap the nebulized aerosol within the device until vacuum pressure, or a significant threshold vacuum pressure, generated from user inhalation, is able to open said one-way valves 2117 and 2118. Nebulized aerosol is thusly contained in reserve chamber 2105 until airflow 2127, originating at one or more airflow inlets 2119, carries the aerosol through the device 2100 and out to the end user through the airflow outlet end 2120 of the device 2100.

Calibrated airflow resistance control element 2121, in this embodiment, consists of a user controlled airflow resistance dial with one or more supplemental apertures 2122. The user controlled airflow resistance dial 2121 is flush with the airflow inlet end of the device 2100. Rotation of dial 2121 aligns supplemental aperture(s) 2122 with one or more airflow inlet passages 2119, thereby controlling the amount of airflow 2127 allowed to enter the device 2100 and travel through these passages 2119, having the effect of controlling the velocity and or volume of airflow through the device 2100. Therefore, the number of different apertures 2119, 2122 is controlled and adjusted by user input. The airflow resistance settings of this device 2100 may also provide an auditory signal to the user, such as a whistle sound caused by air passing through the airflow control element.

Furthermore, the pitch of this whistle sound may vary between different airflow resistance settings and may allow the user to distinguish between such settings. Furthermore, the auditory signal may indicate for user to adjust his or her inhalation rate.

The airflow outlet end of the device 2100 may contain a mouthpiece 2123 that contours to the user's lips, allowing for an airtight seal. Said mouthpiece 2123 may contain an exhaust port 2124, comprised of an elastomeric one-way, flap valve, which vents user exhalation, while one-way valve 2118 prevents exhalation from entering the interior of the device 2100. An optional and or removable filter housing assembly 2140 may be aligned with exhaust port 2124, to allow exhaled air to pass through a filter element 2141, and out of the filter housing 2140 (not shown). A preferred filter element 2141 may be a 3M® filtrate filter, or other HEPA filter, able to capture infectious particles and aerosol particles larger than 0.3 micrometers in diameter from exhalation, thereby preventing cross contamination to nearby individuals. A contaminated filter element may be cleaned or replaced as necessary. Other user interfaces other than the mouthpiece 2123 can be envisioned, including adapters for a respiratory circuit to provide aerosols to patients on mechanical ventilation.

The interior walls of the device, such as along reserve chamber 2105, may be curved and or contain spiral baffles (not shown) or other baffles to generate a rotational flow of aerosolized air that enters the device 2100. Said rotational airflow may surround the aerosol and may more efficiently carry the aerosol out of the device 2100, while reducing impaction or adhesion of aerosol with the inner walls of the device 2100. Other baffle designs can be used in conjunction or alternatively to allow only smaller particles, with a mass median aerodynamic diameter, MMAD, more ideal for inhalation, to exit the device 2100.

The device 2100 also comprises an electronic drive means 2128 that sends an electric drive signal through signal lines 2129*a* and 2129*b* to the piezo electrical conversion unit 2113 and conductive support unit 2112, of the piezoelectric motor assembly 2112, 2113. A power source 2130, preferably a rechargeable battery with micro-USB power (cord) port or USB power (cord) port 2137, provides the electrical energy for the electronic drive means 2128. The aerosol delivery device 2100 is preferably a rechargeable device with USB, micro-USB, or mini-USB power adapter or cord. The device 2100 may further comprise a digital control unit 2131, with user inputs 2132, and a digital display 2133, such as LCD or LED, and or electroacoustic transducer speaker (not shown). The digital control unit 2131 operates the electronic drive means 2128 through circuit lines 2134*a* and 2134*b*. The digital control unit 2131 may also contain a microprocessor or microelectronic circuit that can perform one or more functions, such as: setting the intensity of the electric drive signal, providing visual and or auditory feedback to the user and or health care worker, providing an alarm function to signal when a treatment is due, a timer function to measure the duration of treatment and or to turn off operation after a certain treatment duration, a counting function to determine the number of treatments, a function to keep track of the airflow resistance settings during treatment, a time/date function to track the treatments of one or more different medicament formulations, along with any other functions obvious to the use of this device. Furthermore, the digital control unit may utilize the port 2137 and or memory card so that data can be interfaced with a computer or respiratory instrument.

The aerosol delivery device 2100 may also contain one or more conductivity sensing leads or panels, touch panels (touch panels) 2136, as an integral component of the mouthpiece that forms a switching circuit with the digital control unit 2131 via circuit leads 2135. Conductivity sensing touch panels receive bioelectricity through a living being in contact with the touch panel 2136 to complete this switching circuit, which may signal the digital control unit 2131 to activate electronic drive means 2128 so that the device 2100 may generate or dispense aerosol only when the user is able to receive such aerosol delivery. Said touch panels 2136 may, therefore, prevent aerosol loss when the user is not able to receive aerosol. The switching circuit may include one or more resistors, transistors, grounds, capacitors, and or any other circuit components necessary for the function of this circuit. Touch panels 2136 may also or instead be pressure sensing panels that detect user contact with the device 2100. Alternatively, airflow sensors and or pressure sensors/pressure transducers, could be used in place of, or in addition to, touch panels 2136, to detect changes in airflow and negative pressure caused by user inhalation. Likewise, airflow sensors and or pressure sensors would detect and or monitor user inhalation and provide such information to the digital control unit 2131 that can interpret the data so as to activate and or regulate aerosol generation via electronic drive means 2128, and or to provide visual and or auditory feedback to the user and or health care worker.

Airflow 2127 and or entrained aerosolized air passes through the device housing 2110 and internal chamber 2105, through an at least one airflow passage therein 2116. This airflow path or passage 2116 can, in some embodiments, be adjustable as well. As shown in FIG. 28, the aerosol delivery device 2100 can include airflow path lever 2125 that can slide and or tilt to change the size, angle, and shape of the airflow passage 2116. Airflow path lever 2125 can also include apertures in it (not shown). Additionally, a biasing member 2126, such as a resilient coil or membrane, can provide resistance to the movement of the airflow path lever 2125 and provide resistance to airflow 2127. The biasing force of biasing member 2126 may be linear or exponential; meaning as the airflow path lever tilts from airflow 2127 pushing into it, resistance to tilting may increase linearly or exponentially with each incremental or continuous movement. As the airflow path lever 2125 tilts with increasing inhalation effort and increasing airflow 2127, it regulates at least one parameter selected from user inhalation resistance, user inhalation duration, user inhalation rate, aerosol delivery efficiency, targeting of aerosol to different user airway regions, or a combination thereof.

It is to be understood that parameters for controlling aerosol generation timing and duration, aerosol generation amount, airflow velocity, airflow volume, airflow restriction, negative pressure, user inhalation resistance, user inhalation duration, user inhalation rate, aerosol delivery efficiency, targeting of aerosol to different user airway regions, physical changes of the device, or a combination thereof may be optionally performed or indicated by the digital control unit 2131, and any microprocessor, electronic chip or circuit thereof, via one or more pre-programmed and or programmable algorithms stored in the device or optionally accessible via wireless or blue-tooth from a software application ("app") on a computer, Smartphone, tablet, or diagnostic device. In certain embodiments, the aerosol delivery device 2100 utilizes "machine learning" of an aerosolizable substance's properties and or a user's breathing pattern to fine-tune and adjust the algorithm(s) of the aerosol delivery device 2100 to optimize performance and aerosol delivery, and in a sense, customize that device to a specific aerosolizable substance and or specific user or patient. In some embodiments, algorithm(s) and or data generated can be stored in the device or sent via wireless internet or blue-tooth from an "app" on a computer, Smartphone, or tablet for users, patients, and their trainers or physicians to monitor the use and progress on the device 2100. Therefore, devices of the present disclosure optionally have wireless and or bluetooth connectivity microchips and hardware (not shown). In other embodiments, wireless connectivity is not present, and instead the device 2100 optionally provides data to an "app" on a computer, Smartphone, or tablet via a USB cable or memory card or thumb drive.

Figure 29:
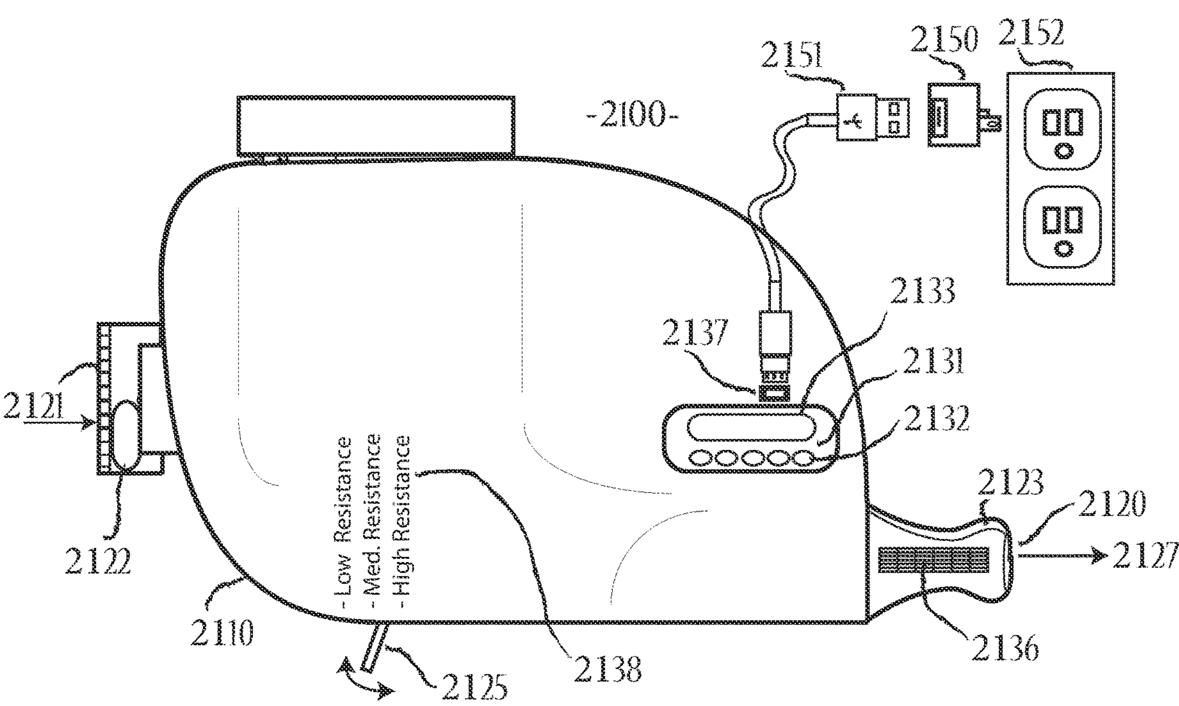
FIG. 29 includes a side view of the aerosol delivery device of FIG. 28, in accordance with an embodiment of the disclosure.

FIG. 29 includes a side view of the aerosol delivery device 2100 of FIG. 28, in accordance with an embodiment of the disclosure. Indicia or calibrated indicia 2138 of airflow resistance settings and or inhalation resistance settings are shown associated with airflow path lever 2125.

User input of turning the dial or calibrated airflow resistance control element 2121 also influences and modulates airflow 2127 and acts on and effects the optional airflow path lever 2125 and its biasing member 2126. To the right of the device 2100 is an alternating current (AC) wall socket outlet 2152, which the device's USB (AC/DC) power adapter 2150 plugs into. A USB charging cable 2151 plugs into USB power adapter 2150 on one end and plugs into micro-USB power (cord) port 2137, or other format of port, of the device 2100 on the other end. The combination of 2150, 2151, 2152, and 2137 can power the aerosol delivery device 2100 directly, or recharge its battery or batteries 2130, and at least in some instances, even when the device 2100 is in use.

In an alternative embodiment of the disclosure, airflow sensors 2136 may also provide feedback of airflow and or breathing pattern data to a digital control unit (or microprocessor) 2131, which can interpret the data and can adjust airflow resistance by sending an electronic signal to an electric motor controlling a calibrated airflow resistance control element, such as that described in the next figure.

In other embodiments, the piezoelectric motor assembly may also serve as, or include, or be accompanied by, or be replaced by, a heat generating element/means to raise the temperature of the air and or aerosolized liquid droplets within the device 2100 to promote reduced particle size and convection. Electrical resistance preferably provides the heat energy for the heat generating means, and so the heat generating element is foremost an electrically resistive heating element. Furthermore, this heat generating element may serve as a vaporizing element to vaporize a liquid or other substance into a condensation aerosol available for inhalation, and may be used with, or instead of, ultrasonic/vibrating mesh nebulization, or be a hybrid among them. Therefore, at least one aerosol generating element (2111, 2112, 2113) may also be or instead be a heating or vaporizing element to produce and deliver aerosols of liquid medicament, e.g., flavored nicotine solutions and *cannabis* oils, etc. Electricity can be used to generate aerosol by vaporizing a medicament formulation with heat from an electrically resistive heating element, electrothermal transducer, or thermo-electrical converter, and allowing that vaporized substance to condense or react in the airflow of the device. The present disclosure provides structures, elements, and methods for vaporization to take place.

Figure 30:
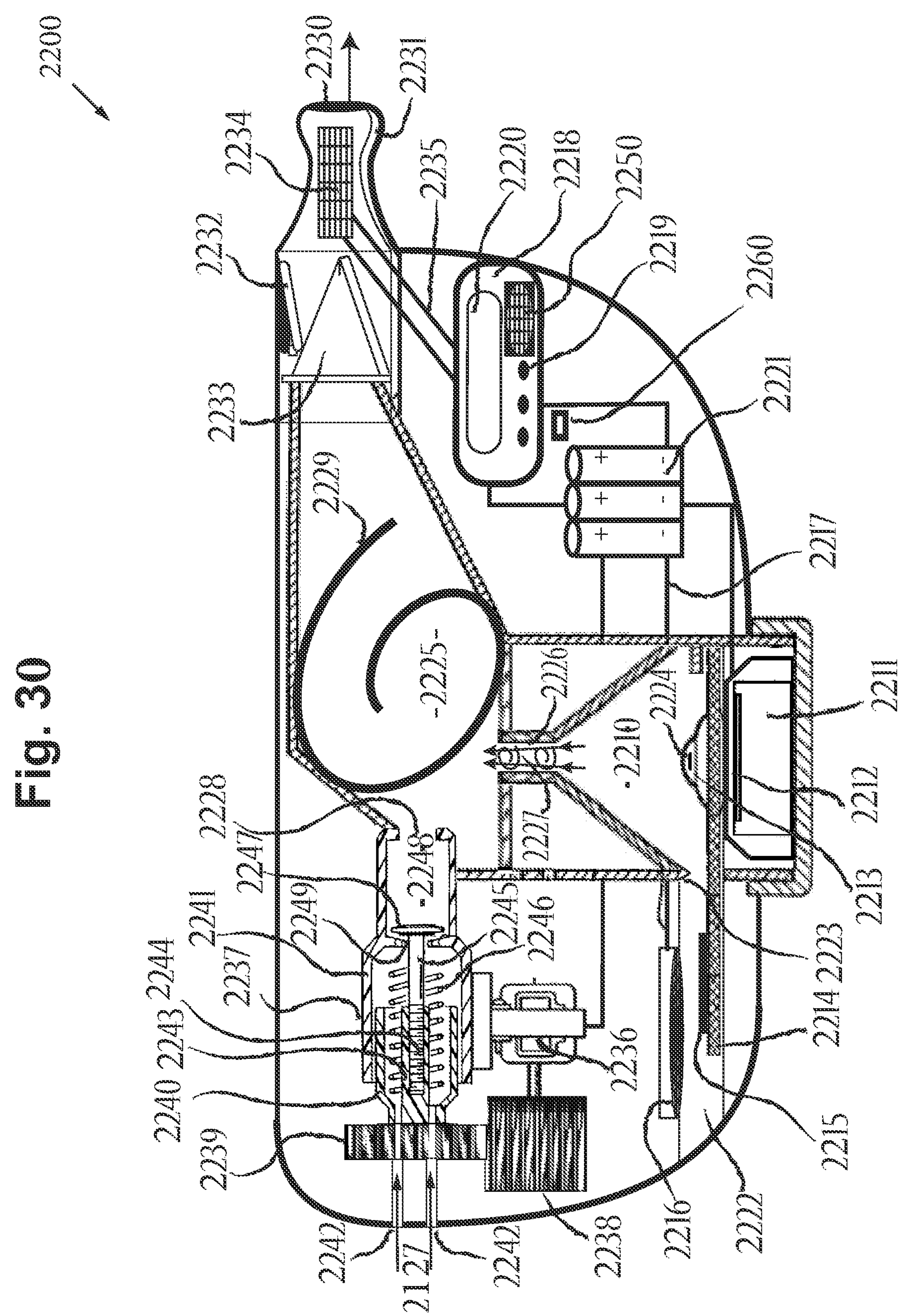
FIG. 30 includes a cross-sectional side view of an alternate aerosol delivery device, in accordance with an embodiment of the disclosure.

FIG. 30 includes a cross-sectional side view of an alternate aerosol delivery device 2200, in accordance with an embodiment of the disclosure. The aerosol delivery device 2200 comprising a horn-shaped, first chamber 2210. An optional piezoelectric transducer 2211 that is made to oscillate, vibrate, while in contact with the proximal end of first chamber 2210, such as to send vibrations to that first chamber 2210. A heating element 2212 can be comprised of an electrically resistive heating support or resistor, and is located in close communication with the proximal end of first chamber 2210, such as to send heat to that first chamber 2210, including sending heat to an aerosolizable substance or medicament. The piezoelectric transducer 2211 and heating element 2212 may be housed together. A (preformed) blister pack 2213, or other aerosolizable substance or formulation cartridge or packaging, filled with a preferably liquid aerosolizable substance or formulation, but also a gel or solid aerosolizable substance or formulation, can be housed on a slidable structure, slide, strip, 2214, that can be inserted into first chamber 2210, such as along or near its proximal end. Slide 2214 can optionally contain a coded tag 2215, such as a bar code, microchip, transmitter, radio-frequency identification tag, or other means, that can be detected and or analyzed by an electronic tag reader 2216. Optional tag reader 2216 is able to detect the presence of the blister pack 2213 and slide 2214. The coded information detected may also include the type of aerosolizable substance or medicament and or also its dosage and or its serial number. If the aerosol delivery device 2200 is to nebulize and or vaporize a non-medicinal substance, such as a flavored nicotine-containing liquid, the coded tag 2215 may not be necessary. However, if the device 2200 is nebulizing and or vaporizing a prescription drug, such as an opioid or cannabinoid or other controlled substance or analogue or derivative, then a coded tag 2215 may provide essential information, such as to monitor use and prevent abuse of the drug products. In some states, cannabinoids or marijuana or marijuana-derived substances may be used medicinally or recreationally, in which case aerosol delivery with this device 2200 would be ideal and optimized. Other ideal drugs for treating symptoms, conditions, and or diseases can include aerosolized diabetic drugs such as aerosolized insulin, aerosolized epinephrine for treating allergic reactions and anaphylaxis/anaphylactic shock, other bronchodilators for treating asthmatic symptoms, aerosolized antibiotics for treating infection, aerosolized analgesics for treating pain, aerosolized prostacyclins and prostacyclin analogues for treating pulmonary arterial hypertension, immunomodulators for treating asthma, and aerosolized chemotherapies for treating cancers including lung cancer. Orphan drug products for treating cystic fibrosis and organ transplant rejection can also be delivered efficaciously with this device. Vaccines and other immunotherapies can also be delivered in this manner. Some aerosolizable substances can be nebulized and vaporized, while other aerosolizable substances may be better suited for vaporization or nebulization due to viscosity or heating degradation. The present disclosure allows for all three conditions to be satisfied and opens the potential to aerosolize virtually all substances.

The tag reader 2216 may send information through an electronic circuit 2217, preferably wired to a digital control unit 2218, with user inputs 2219, and a digital display 2220, such as LCD or LED. The digital control unit 2218 controls the operation of the piezoelectric transducer 2211 and or heating element 2212, using power from one or more batteries or rechargeable batteries 2221. Preferably, a micro or mini-USB power (cord) port or USB power (cord) port 2260 provides the interface for external electrical energy for generating aerosol with this device 2200, and or for recharging batteries 2221. In this case, an alternating current (AC) wall socket outlet 2152, which the device's USB (AC/DC) power adapter 2150 plugs into, would be utilized. Also utilized is a USB charging cable 2151 that plugs into USB power adapter 2150 on one end and plugs into micro-USB power (cord) port 2260, or other format of port, of the device on the other end. The combination of 2150, 2151, 2152, and 2260 can power the aerosol delivery device 2200 directly, or recharge its battery or batteries 2221, and at least in some instances, even when the device 2200 is in use.

The detection and or analysis of the coded medicament information 2215, by the reading device 2216, may allow the digital control unit 2218 to turn the piezoelectric transducer 2211 and or heating element 2212 on for certain durations, and or may determine the desired power and frequency to operate the piezoelectric transducer 2211, and may determine the desired power and temperature to heat the heating element 2212, for proper delivery characteristics of that particular medicament code.

When medicament slide 2214 is inserted into the aerosol delivery device 2200, through the medicament port channel

2222, an optional piercing means or mechanism 2223 can remove or cause openings 2224 on the top of blister package 2213, by which medicament can be released into the first chamber 2210. When activated, heating element 2212 is able to vaporize the medicament substance from medicament slide 2214 by sending thermal energy to the substance by conduction and or convection. In other embodiments, heating element 2212 can be located on medicament slide 2214 as an electrically resistive heating support, such as a metal foil support, which may even be part of blister packaging 2213. As such, an aerosolizable substance or formulation or medicament may be coated on this metal foil support. After vaporization, preferably with minimal degradation products of medicament, the vapor can cool and condense to form a condensation aerosol available for inhalation. As will next be described, this vapor can be efficiently carried to an aerosol holding chamber 2225 where the particles can cool further.

First chamber 2210 is connected to a second chamber 2225 via a narrow orifice or channel 2226. Vibration of the proximal end of first chamber 2210 by the vibrations caused by the optional piezoelectric transducer 2211, sets up pressure variations, as well as standing waves and or acoustic waves, within the first chamber 2110, causing air in the first chamber 2210 to move back and forth through channel 2226, while vortices of air are formed at channel 2226, leading to second chamber 2225. A synthetic jet of air 2227 is thus created by these vortices, resulting in the net flow of air from first chamber 2210 into second chamber 2225. Vapor and condensation aerosol is entrained in this airflow and evacuated from first chamber 2210, and carried to the second chamber 2225, by a synthetic jet 2227 via channel 2226. When the aerosolizable substance is a dry powder, and the heating element 2212 does not vaporize some or all of the powder, such as when the heating element 2212 is not activated or when the heat transfer is less than 100% efficient, piezoelectric transducer 2211 can still vibrate and mix air in the first chamber 2210 to disaggregate the dry powder released from blister pack 2213, to form an aerosol. The aerosolized dry powder is entrained in the air and evacuated from first chamber 2210, and carried to the second chamber 2225, by a synthetic jet 2227 via channel 2226. As such, this aerosol delivery device 2200 can serve as a dry powder inhaler. In most embodiments, the aerosol delivery device 2200 is preferably a vaporizer and or nebulizer. In other words, the device 2200 can be a hybrid between vaporization and nebulization (hybrid vaporizer/nebulizer). In some embodiments, a switch can determine when the aerosol generating element performs vaporization or vibrational nebulization. In other embodiments, the digital control unit 2218 or microprocessor automatically determines the amount of heating or vibrating for vaporization and or nebulization, which may also tie into information about the specific aerosolizable substance inputted by the user or obtained from the coded tag 2215 and tag reader 2216. Only electrical energy, and not compressed air/pressurized gas, produces aerosols with this device by providing kinetic energy to heat or vibrate molecules of aerosolizable substance.

Second chamber 2225 can serve as an aerosol reserve, holding, chamber. Airflow enters device chamber 2225 through inlet passage 2228, where it may be vortexed by the curved interior walls or spiral baffles 2229 of this chamber 2225, before exiting the device 2200 via outlet end 2230. Airflow outlet end 2230 can consist of a user mouthpiece 2231 that contours to the user's lips, allowing for an airtight seal. Said mouthpiece 2231 may optionally contain an exhaust port 2232, comprised of an elastomeric one-way, flap, valve, which vents user exhalation, while optional one-way valve 2233, preferably a duckbill valve, prevents exhalation from entering the interior of the device 2200. The outlet end 2230 may have interchangeable mouthpieces of different sizes to change airflow through it, or may have a mechanism to be turned to adjust airflow by modulating airflow restriction (not shown). Other user interfaces other than a small mouthpiece can be envisioned, including a hose, hose with mouthpiece, facemask, oxygen mask, nosepiece or nasal prong can be used alternatively. The aerosol delivery device 2200 may also contain one or more airflow sensors 2234 that form(s) a switching circuit with the digital control unit 2218 via circuit leads 2235. Detection of user airflow may signal the digital control unit 2218 to activate and or regulate piezoelectric transducer 2211 and or heating element 2212 for aerosol delivery. Airflow sensors may also provide feedback of airflow and or breathing pattern data to a digital control unit, or microprocessor, 2218, which can interpret the data and can adjust airflow resistance by sending an electronic signal to an electric motor 2236, controlling a calibrated airflow resistance control element 2237 by means of gears 2238 and 2239. The acoustic horn shape of this embodiment, along with its associated synthetic jet, is preferred, although one can envision other embodiments where the acoustic horn is not used. The main feature of these embodiments are, however, a calibrated airflow resistance control element 2237 that controls the velocity and or volume of airflow through the device 2200. There exist many ways to achieve this calibrated airflow resistance control element 2237, and one such way is with an inhalation threshold resistance valve assembly that regulates airflow entering chamber 2225 via inlet 2228, thereby effecting the airflow through the device 2127.

The inhalation threshold resistance valve assembly 2237 is comprised of a rotatable cap 2240 with an integrally formed cylindrical wall slidably received through a cylindrical housing 2241. Gear 2239 is connected to, or forms the top of, rotatable cap 2240. Gear 2239, and or the top of rotatable cap 2240, contains one or more air inlet ports 2242 that allow airflow to enter airflow resistance control element 2237, which allows airflow to enter chamber 2225 via inlet 2228, when this inhalation threshold resistance valve assembly 2237 is open. Rotatable cap 2240 also has a tubular guide 2243 extending through it. The tubular guide 2243 has female threads 2244 that is designed to receive the male threads of a thin rod 2245. A load calibrated, coiled spring 2246, or other resilient or biasing member, is positioned inside of the rotatable cap 2240, around the tubular guide 2243 and thin rod 2245. A circular disc 2247, along thin rod 2245, is located within a chamber region 2248, adjacent to reserve chamber 2225, and serves as the actuator piston of inhalation threshold resistance valve assembly 2237. As spring 2246 puts outward pressure on rotatable cap 2240, circular disc 2247 is pulled against the proximal surface of chamber 2248, thereby blocking this chamber's proximal aperture 2249, which in some embodiments can serve as a Venturi or Venturi-like structure or function.

Upon inhalation, when a threshold level of negative pressure, vacuum pressure, is applied on the inhalation threshold resistance valve assembly 2237, the inhalation threshold resistance valve assembly 2237 will open as the spring 2246 compresses and the actuator piston moves away from its resting position. Rotatable cap 2240 is able to slide within cylindrical housing 2241, commensurate with gear 2239 being able to slide along gear 2238. When the inhalation threshold resistance valve assembly 2237 is open, ambient air enters the device 2200 through air inlets 2242, and passes through chamber 2248 and reserve chamber 2225, entraining aerosolized particles, and carrying these particles out of the device 2200 through outlet 2230. The inhalation threshold resistance valve assembly 2237 closes when negative pressure within chamber 2225, and chamber 2248, can no longer overcome the tension of the spring 2246. The inhalation threshold resistance valve assembly 2237 also serves as a calibrated airflow resistance control element. As electric motor 2236 turns gears 2238 and 2239, rotatable cap 2240 is rotated like a dial. When the rotatable cap 2240 is rotated, the distance that the thin rod 2245 screws into the tubular guide 2243 of the rotatable cap 2240 also changes, thereby affecting the space between the rotatable cap 240 and the cylindrical housing 2241, and thus, the compression of the spring 2246. By varying the tension of the spring 2246, one can control inhalation resistance, negative pressure, and the velocity and or volume of airflow through the device 2200, which may allow for aerosol delivery with sustained maximal inspiration/inhalation. The number of partial or full revolutions that the electric motor 2236 must spin in order to turn gears 2238 and 2239, and thus, rotatable cap 2240, necessary to adjust the tension of load calibrated spring 2246, is programmed into the digital control unit 2218. Thus, digital control unit 2218 can automatically adjust airflow resistance settings based on user inputs 2219, or from data signals generated from airflow sensor 2234. Other embodiments may utilize a manual means for adjusting calibrated airflow resistance settings.

The digital control unit 2218 may also contain a microprocessor that can perform one or more functions, such as: providing an alarm function to signal when a treatment is due, a timer function to measure the duration of treatment and or to turn off operation after a certain treatment duration, a counting function to determine the number of treatments, a function to keep track of the airflow resistance settings during treatment, a time/date function to track the treatments of one or more different medicament formulations, the ability to store settings for different medicament formulations, along with any other functions obvious to the use of this device. The digital control unit 2218 may have an electronic speaker 2250 that provides auditory feedback to the user regarding the user's progress and or to adjust the user's inhalation rate or breathing pattern, and or to provide the user with incentive. The electronic speaker may provide human sounding words to provide such auditory feedback, and may also voice aloud device settings and functions. The aerosol delivery device 2200 can train the user on proper inhalation technique for optimized aerosol delivery efficiency, or overcome any incorrect inhalation technique. The digital control unit 2218 may contain a memory card (not shown) so that data can be interfaced with a computer or respiratory instrument.

This embodiment utilizes a medicament strip 2214 with a single medicament blister 2213. One can envision other embodiments where multiple blisters are housed on the strip 2214, or a device 2200 that can hold and use multiple unit dosages of medicament(s), sequentially. Other embodiments can include cartridges. Some embodiments can include at least two different aerosolizable substances or formulation dosages that can be aerosolized separately and or simultaneously with this device 2200. Some of these embodiments have control or selection means to control or select which of these at least two different aerosolizable substances or formulations are to be aerosolized and delivered at any given time or times; selected manually or by digital control. This is desirable when having two or more lifesaving emergency drugs, such as epinephrine and an anticholinergic such as atropine, such as if a soldier is exposed to nerve agent or anaphylaxis causing agent.

It is to be understood that parameters for controlling aerosol generation timing and duration, aerosol generation amount, airflow velocity, airflow volume, airflow restriction, negative pressure, user inhalation resistance, user inhalation duration, user inhalation rate, aerosol delivery efficiency, targeting of aerosol to different user airway regions, physical changes of the device 2200, or a combination thereof may be performed by the digital control unit 2218, and any microprocessor, electronic chip or circuit thereof, via one or more pre-programmed and or programmable algorithms stored in the device 2200 or optionally accessible via wireless or blue-tooth from an software "app" on a computer, Smartphone, tablet, or diagnostic device. In certain embodiments, the aerosol delivery device 2200 utilizes "machine learning" of an aerosolizable substance's properties and or a user's breathing pattern to fine-tune and adjust the algorithm(s) of the aerosol delivery device 2200 to optimize performance and aerosol delivery, and in a sense, customize that device 2200 to a specific aerosolizable substance and or specific user or patient. In some embodiments, algorithm(s) and or data generated can be stored in the device 2200 or sent via wireless internet or blue-tooth from an "app" on a computer, Smartphone, or tablet for users, patients, and their trainers or physicians to monitor the use and progress on the device.

Therefore, devices of the present disclosure optionally have wireless and or blue-tooth connectivity microchips and hardware (not shown).

Figure 31:
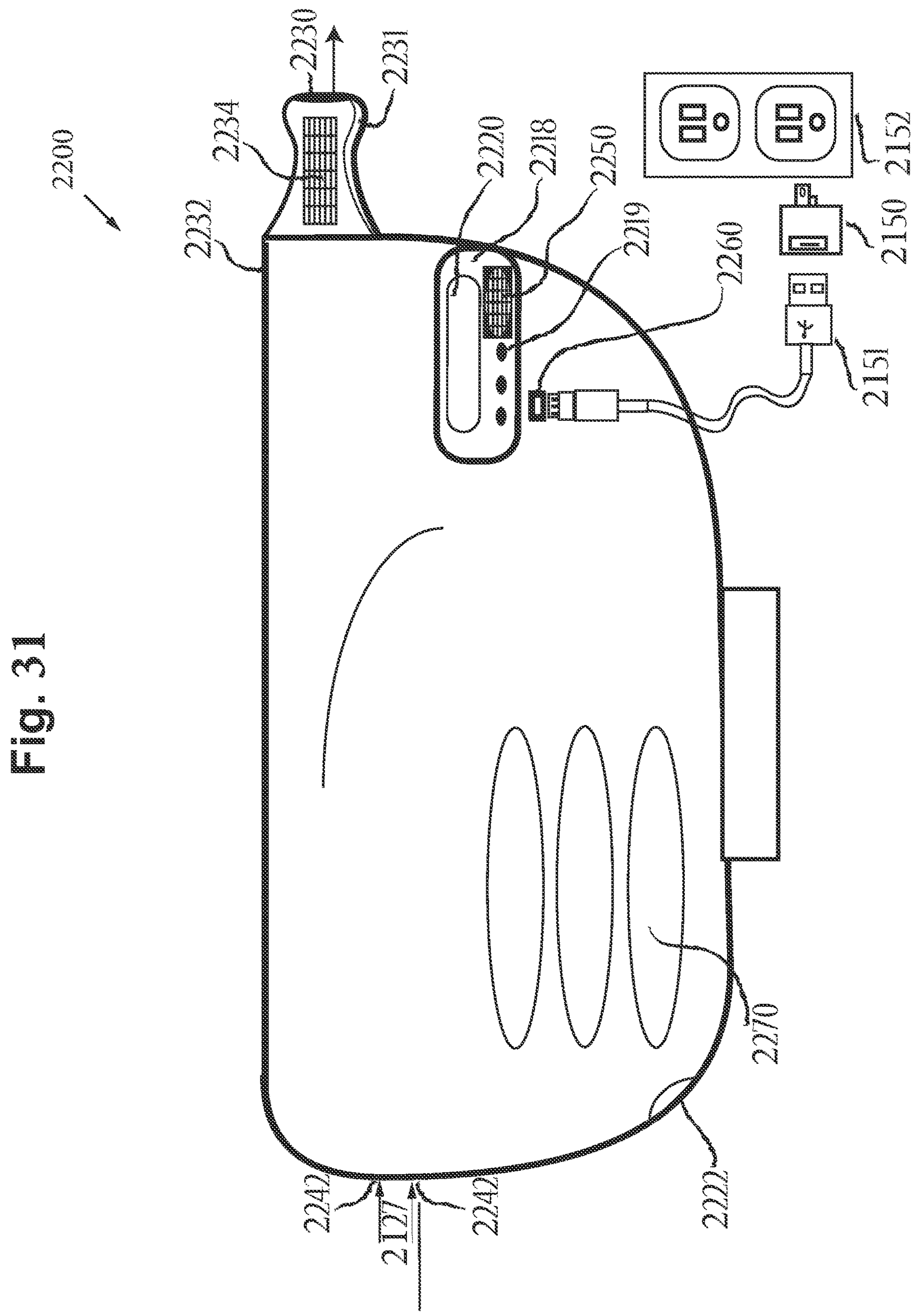
FIG. 31 includes a side view of the aerosol delivery device of FIG. 30, in accordance with an embodiment of the disclosure.

FIG. 31 includes a side view of the aerosol delivery device 2200 of FIG. 30, in accordance with an embodiment of the disclosure. As shown in FIG. 31, the aerosol delivery device 2200 includes hand or finger grips 2270, as well as the power adapter and cord for the device's 2200 port 2260. Medicament port channel 2222 is accessible externally to slide a cartridge or strip of aerosolizable substance into the device 2200. Airflow 2127 enters from the left and travels through the device 2200 and exits to the right.

Other embodiments may rely on one or more solenoid valves under the control of a digital control unit. These other conceivable embodiments are not shown and are not meant to be limiting.

Figures 32A, 32B:
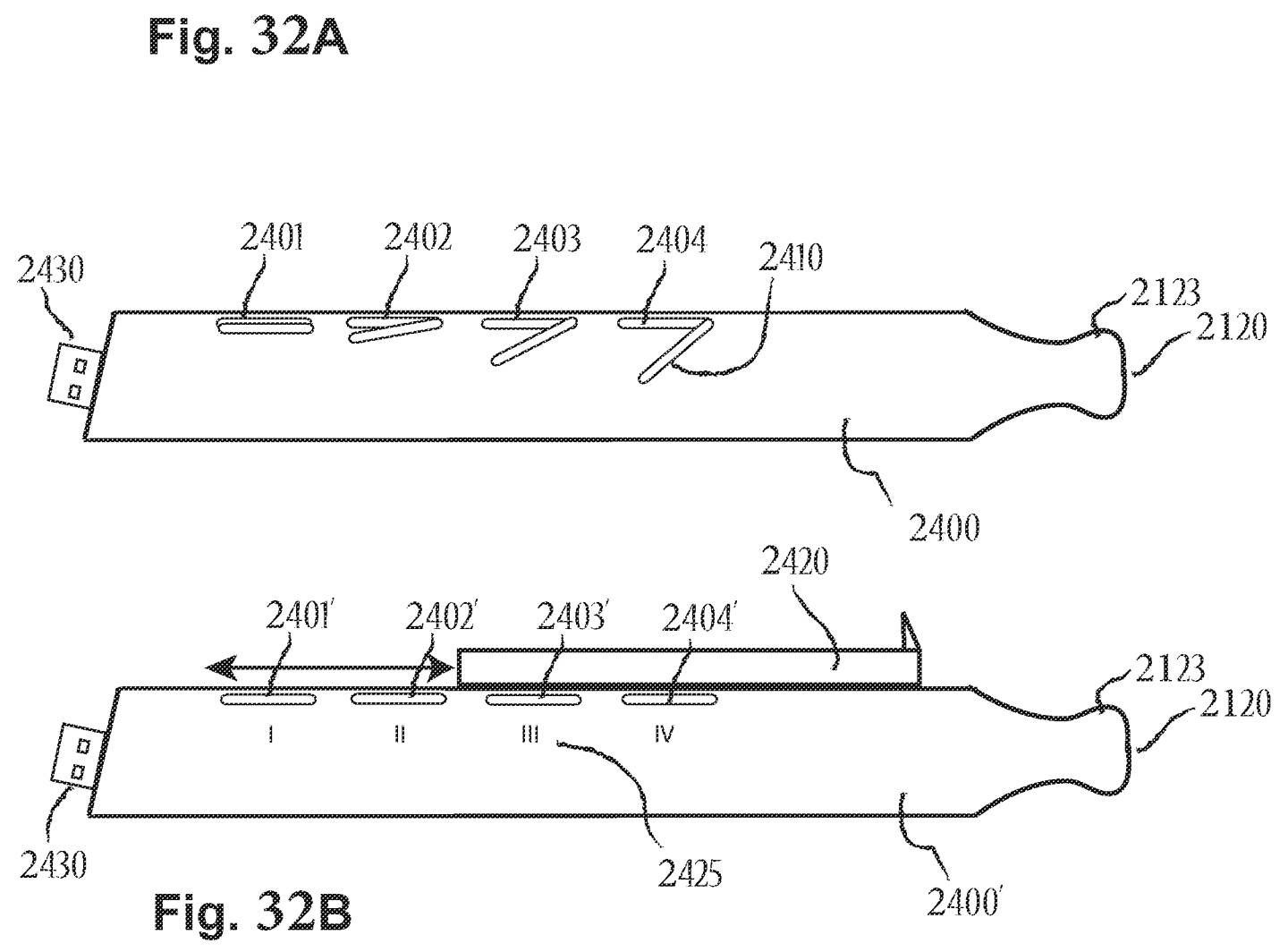

FIG. 32A includes a side view of an aerosol delivery device housing 2400, in accordance with an embodiment of the disclosure. As shown in FIG. 32A, the aerosol delivery device housing 2400 has four ambient air inlets 2401, 2402, 2403, and 2404, each having a resilient biasing member 2410 that covers them by pressing against the air inlets 2401, 2402, 2403, and 2404 in a valve-like manner. When a user inhales through the aerosolized air outlet 2120 via mouthpiece 2123 with significant inhalation effort and negative pressure, different negative pressures above 1 centimeter of water, and preferably above 3 centimeters of water, the resilient biasing members 2410 are gradually and or sequentially pulled away from covering air inlets 2401-2404. The greater the inhalation effort and negative pressure generated by the user which overcomes the thresholds of these valve-like structures, the more the air inlets 2401-2404 are uncovered. The opening of one or more of these air inlets 2401-2404 is a physical change which lets ambient airflow into the housing 2400, which causes the housing 2400 to lose negative pressure inside, which increases the difficulty of the user trying to generate negative pressure. In this configuration, the device automatically in an analog manner adjusts the airflow through the device and user inhalation resistance and other parameters as well. The faster and or stronger the inhalation effort from the user, the more the device adjusts to increase inhalation resistance. The biasing member force of these resilient biasing members 2410 can be selected at the time of manufacture to obtain the desired biasing member force for certain user abilities. Other embodiments can include structures to dial the desired biasing member 2410 force setting for similar valves (not shown).

FIG. 32B includes a side view of an alternate aerosol delivery device housing 2400', in accordance with an embodiment of the disclosure. The alternate aerosol delivery device housing 2400' of FIG. 32B has an outline that is a similar an outline of the aerosol delivery device housing 2400 of FIG. 32A, but with no resilient biasing members 2410 covering ambient air inlets 2401', 2402', 2403', and 2404'. Instead a sliding, calibrated resistance control element 2420 is manually adjusted by the user with the digits of the user's fingers according to calibrating indicia 2425 to cover one or more ambient air inlets 2401', 2402', 2403', and 2404', thus, control the at least one airflow through the device housing 2400' and an at least one parameter selected from user inhalation resistance, user inhalation duration, user inhalation rate, aerosol delivery efficiency, targeting of aerosol to different user airway regions, or a combination thereof. Note that both the aerosol delivery device housing 2400 of FIG. 32A and the alternate aerosol delivery device housing 2400' of FIG. 32B show a male USB fitting 2430 distal to the mouthpiece 2123 end. The mini, micro, or standard male USB fitting 2430 (in other embodiments mini, micro, or standard female USB fitting) supplies electrical power directly to the aerosol generating element or other internal circuitry, or to a rechargeable battery thereof via a power cord and or USB power adapter. In other embodiments, the USB interface may configure the settings of the aerosol generating element (not shown). The rechargeable battery can be internal or external, and in some embodiments, detachable and or replaceable.

Figure 33:
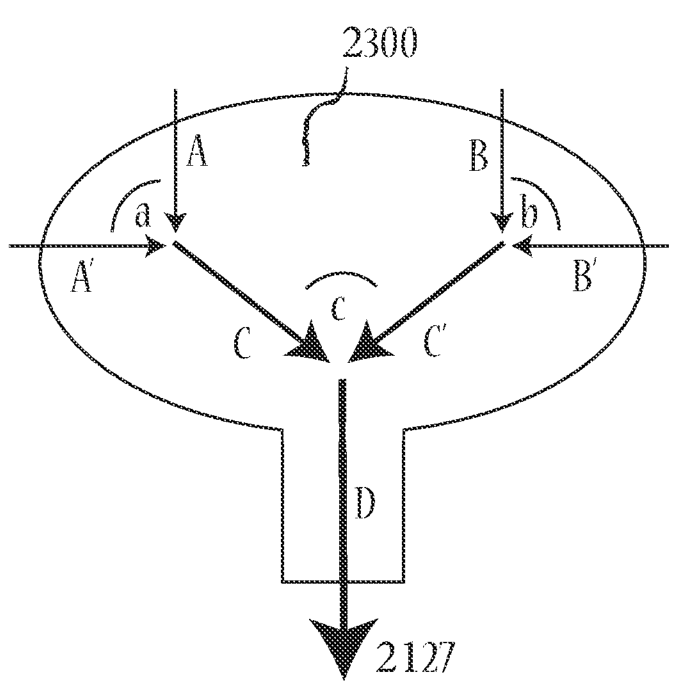
FIG. 33 includes an airflow control diagram of a method for controlling airflow through an aerosol delivery device, in accordance with an embodiment of the disclosure.

FIG. 33 includes an airflow control diagram of a method for controlling airflow through an aerosol delivery device. As shown in FIG. 33, an aerosol chamber 2300 receives aerosol from an aerosol generating element (not shown). Line segment arrows A, A', B, and B' show ambient airflow entering the device, device housing, and or aerosol chamber. Line segment arrows A and A', as well as, B and B' in the current configuration, intersect at oblique right angles to each other to slow their airflow velocity. The resulting airflows, line segment arrows C and C', entrain aerosol and also intersect perpendicularly at right angles to each other. The final resulting aerosolized airflow, line segment arrow D, exits out the aerosol chamber 2300 and or aerosol outlet of the device. All these airflow line segment arrows comprise the overall airflow 2127 through the device. The diagram of FIG. 33 also shows a method of controlling airflow through an aerosol delivery device by having two or more airflows or airflow paths interact or interfere with each other at oblique and or non-oblique angles. The angles of intersection among these different airflow paths, namely angles (a), (b), and (c) in the diagram, can be changed by one or more different means, under manual analog or digital control, such as by tilting or bending one or more of these airflow paths of A, A', B, B', C, and C'. When the angle of incidence between two or more airflows/airflow paths is more than 90 degrees, velocity is decreased more as components of their vectors of momentum cancel each other out more. When the angle of incidence is less than 90 degrees, velocity is not decreased as much or is increased. If airflow paths approach becoming close to parallel to each other in the same direction, velocity between them will be nearly additive. This method employs airflow vector addition and subtraction to control airflow through the device and inhalation parameters experienced by the user. Turbulence and other fluid dynamics of these airflows also come into play. This diagram and method is not mean to be limiting, and instead is intended to broaden the horizons of what is possible through the Applicant's inventive device; aerosol delivery properties and parameters of inhalation of aerosolized airflow can now be controlled in profound ways. The velocity of aerosol discharge and or entrained aerosol airflows can be reduced or manipulated with airflow and or aerosol paths angled toward one another. Alternatively or in addition, airflow control can also include the shunting of one or more airflow paths. These other conceivable embodiments are not shown and are not meant to be limiting.

The embodiments presented and other conceivable embodiments can include a threshold that either lets airflow into the device or aerosol chamber or some other airflow path, and or lets airflow out of the device or aerosol chamber or some other airflow path. When the threshold is overcome, the airflow path opens. It is desirable to have an adjustable airflow resistance and or negative pressure threshold. It may also be desirable to have a threshold associated with inhalation and or exhalation that actuates or activates aerosol generation or aerosol discharge of the device. The present disclosure can accomplish this with structures, functions, properties, and methods amenable to do so.

Increased airflow resistance and or increased negative pressure settings of this disclosure require an increased inhalation effort (negative pressures above 1 cm of water, and preferably above 3 cm of water) and can provide exercise to the muscles involved in respiration. The breathing exercise therapy provided by this device can also help maintain lung elasticity. Some embodiments can have the ability to bypass or remove or nearly remove airflow resistance or negative pressure resistance thresholds.

Embodiments of this disclosure may utilize flow throttling structures, and flow throttling structures that indicate airflow and or inhalation is taking place, and even to what extent. Such flow throttling structures, such as a Venturi, ball, disc, flap, weight, impeller, springs, compressible materials, or moveable baffle can serve as inhalation and or exhalation incentive, and could conceivably take the place of an incentive spirometer if calibrated with indicia and can be visualized.

Other embodiments can be adapted to provide positive expiratory pressure (PEP) therapy, such as with an exhalation threshold resistance valve or PEP valve.

Some embodiments can include a vibratable/oscillatable aperture mesh/membrane, to atomize/nebulize aerosol from a liquid substance, such as when said liquid comes in contact with/passes through the mesh, the source of vibration/oscillation being chosen from vibratory means chosen from the class of electro-mechanical vibratory means including, but not limited to, piezoelectric elements, including piezoelectric transducers, piezoelectric pumps, and piezoelectric motors, the vibratory mesh element including regions of one or more different curvatures and pores of one or more different sizes, oscillations including bending oscillations, such as of the vibratable mesh. Oscillations can be adapted to occur at ultrasonic frequencies.

Some embodiments are adapted to force a liquid through at least one small orifice, such as part of a spray nozzle, ejection actuator, or aperture mesh, to cause aerosolization of that liquid, the means for moving the liquid is chosen from physical means chosen from the class of mechanical/electro-mechanical means including, but not limited to, pumps, such as electric pumps, hydraulic pumps, and piezoelectric pumps, pistons, injectors, piezoelectric elements, piezo-inkjets, thermal inkjets, thermal bubble jets, synthetic jets, solenoids, and valves.

Some embodiments are adapted to control the activity of at least one aerosol generating element, chosen from among aerosol generating elements, including, but not limited to, spray nozzles, ejection actuators, aperture meshes, vibratable plates, and heating/vaporizing elements.

The settings of most embodiments are adapted to be adjustable and adjusted by any physical means, including, but not limited to, rotatable means, slidable means, manual means, mechanical means, electro-mechanical means, including electric motors, analog control means, digital control means, and microprocessor control means.

Some embodiments include an aerosol delivery device with an at least one controller/microprocessor adapted to adjust airflow resistance settings, such as by electric motorized means, the controller/microprocessor adapted to adjust the airflow resistance settings based on input received from at least one electronic sensor, being chosen from the class of electronic sensors, including, but not limited to, pressure transducers, piezoelectric sensors, and other airflow sensors, such sensors adapted to provide the controller/microprocessor with at least some user or patient information chosen from the class of breathing information, including, but not limited to, inhaled air volume, exhaled air volume, inhaled airflow rate, exhaled airflow rate, breathing cycle patterns, and other lung function parameters of spirometry, such as tidal volume, forced vital capacity, and lung capacity, in this manner, the device is able to adjust to the properties of the user, such as for optimized aerosol delivery, the device is adapted to display these measured parameters allowing the device to serve as a pulmonary diagnostic tool/instrument.

Some embodiments include an aerosol delivery device with an at least one controller/microprocessor adapted to modulate the operation of at least one aerosol generating element, the controller adapted to modulate the operation of the at least one aerosol generating element based on input received from at least one electronic sensor, being chosen from the class of electronic sensors, including, but not limited to, conductivity sensing leads, pressure transducers, piezoelectric sensors, and other airflow sensors, such sensors adapted to provide the controller/microprocessor with at least some user or patient information chosen from the class of breathing information, including, but not limited to, inhaled air volume, exhaled air volume, inhaled airflow rate, exhaled airflow rate, breathing cycle patterns, and other lung function parameters of spirometry, such as tidal volume, forced vital capacity, and lung capacity, in this manner, the device is able to adjust to the properties of the user, such as for optimized aerosol delivery, the device also allows aerosol generation to be breath/touch activated and synchronized with portions of the breathing cycle.

Some embodiments are adapted to modulate aerosol particle size, such as by modulating the size and number of nozzle/mesh orifices and or oscillations, and or as well as temperature.

Some embodiments are adapted to modulate aerosol particle size by modulating the operation of at least one aerosol generating element, including, but not limited to, its frequency and intensity, aerosol generating elements are chosen from among sites of aerosol generation, including, but not limited to, spray nozzles, ejection actuators, aperture meshes, vibratable plates, and vaporizing elements.

Some embodiments include a heating element that raises the temperature of the air and aerosol within the device, such as above that of ambient air, said heating element adapted to help evaporate aerosol droplets to reduce particle size, said heating element also produce convection currents that are adapted to help move aerosolized air, the activity and temperature of the heating element adapted to be controlled by electronic means as the heating element is adapted to be an electrically resistive heating element.

Some embodiments can include a valved aerosol holding chamber to retain aerosol within the device until/between periods of user inhalation, the chamber/region also being valved to prevent user exhalation from entering far into the interior of the device, valves chosen from fluid regulating devices chosen from the class of valves including, but not limited to, elastomeric valves, one-way valves, flap valves, duckbill vales, pistons, and threshold valves.

Some embodiments include vaporization means to vaporize a therapeutic substance to produce a condensation aerosol available for inhalation, vaporization means chosen from the class of vaporization elements including, but not limited to, electrically resistive heating elements, electrostatic chargers, elements producing thermal radiation, elements that transfer thermal energy by conduction, elements that transfer thermal energy by convection, elements releasing exothermic energy from chemical reactions, laser producing elements, and elements producing electromagnetic radiation, such as microwaves, radio frequency waves, and infrared waves.

Some embodiments include means to electronically store data, algorithms, and or programs, the electronically stored data is chosen from the types of electronic data including, but not limited to data records, such as time, date, time and or date of treatment, treatment duration, airflow resistance settings, flow rate, flow volume, number of dosages used and unused, dosage amounts, medicament information, such as name and serial number, breathing pattern information, user's progress, device program information, such as device temperature settings, frequency settings, airflow settings, timing settings, aerosolization settings for a particular type of medicament, and other user settings, such as alarm settings and password protection, said electronic data is adapted to be stored and accessed from an Electrically Erasable Programmable Read-Only Memory, EEPROM, and flash memory chips, and or USB ports or other ports.

Most embodiments will conserve the aerosolizable substance or formulation by incorporating a pump or drive system or aerosol generating element that is breath-activated, and may be turned on and off depending on the stage in the user's breathing cycle. The breathing cycle includes the stages of inhalation, pause, and exhalation.

The purpose is for the device to be responsive to inhalation, that it may activate the pump, drive, or aerosol generating element during inhalation, and inactivate the pump, drive, or aerosol generating element when inhalation is no longer detected, i.e., during exhalation, or with a timer.

The disclosure describes an aerosol delivery device having a structure comprising a housing, an at least one ambient/unaerosolized air inlet, an at least one aerosolized air outlet, and an at least one airflow passage therein the device or housing and or extending at least partially there between the at least one ambient/unaerosolized air inlet and the at least one aerosolized air outlet. The aerosol delivery device further comprises an at least one aerosol generating element that produces an aerosol from an at least one aerosolizable substance or formulation with the use of electrical energy and without the use of compressed/pressurized gas. The aerosol delivery device further has an at least one airflow through its housing produced by a user inhaling from the aerosol delivery device and entraining the aerosol when generated; wherein the at least one airflow is controllable in velocity, volume, or a combination thereof as the at least one ambient/unaerosolized air inlet, the at least one aerosolized air outlet, the at least one airflow passage, or a combination thereof undergoes an at least one physical change selected from changes in size, angle, shape, biasing resistance to flow, number of apertures, shunting of airflow, or a combination thereof. The at least one physical change is modulated by user/digital input to control the at least one airflow and to regulate an at least one parameter selected from user inhalation resistance, user inhalation duration, user inhalation rate, aerosol delivery efficiency, targeting of aerosol to different user airway regions, or a combination thereof.

In preferred embodiments, the user/digital input is selected from user inhalation, user touch, user speech/sound, user programming, user selection, or a combination thereof.

In preferred embodiments, the aerosol delivery device further comprises at least two physical change settings when the at least one physical change is modulated by user/digital input.

In preferred embodiments, the aerosol delivery device further comprises marked/digitized indicia, preferably calibrated indicia, adapted to be presented to the user and further representing the at least one parameter selected from user inhalation resistance, user inhalation duration, user inhalation rate, aerosol delivery efficiency, targeting of aerosol to different user airway regions, or a combination thereof.

In preferred embodiments, the aerosol delivery device further comprises an at least one airflow sensor, pressure sensor, or a combination thereof.

In preferred embodiments, the aerosol delivery device further comprises an at least one airflow indicator, pressure indicator, or a combination thereof.

The aerosol delivery device generally comprises an at least one airflow valve, pressure valve, or a combination thereof.

In preferred embodiments, the aerosol delivery device further comprises an at least one aerosolizable substance or formulation or liposomal formulation, said at least one aerosolizable substance or formulation preferably comprises epinephrine, bronchodilator, anticholinergic, nicotine, cannabinoid, opioid, insulin, antibiotic, prostacyclin, interleukin, cytokine, vaccine, immunosuppressant, immunomodulator, immunotherapy, chemotherapy, or combination, analogue, or derivative thereof.

In preferred embodiments the aerosol delivery device further comprises an at least one holding/storage area, chamber, reservoir, or combination thereof for the at least one aerosolizable substance or formulation.

In most embodiments, the aerosol delivery device further comprises an at least one power button/switch.

In some embodiments, the aerosol delivery device further comprises an at least one airflow filter.

In some embodiments of the aerosol delivery device, the at least one airflow through the device housing produced by the user inhaling from the aerosol delivery device interacts with at least one additional airflow through the device housing produced by the user inhaling from said aerosol delivery device so that these airflows meet in at least partially counterposing directions to at least partially negatively interfere with each other; the resulting at least partial negative interference is adapted to change/control or reduce the velocity and or trajectory of at least one of these airflows.

In some embodiments of the aerosol delivery device, the at least one airflow through the device housing produced by the user inhaling from the aerosol delivery device interacts with at least one additional airflow through the device housing produced by the user inhaling from the aerosol delivery device so that these airflows meet in at least somewhat parallel directions to at least partially positively interfere with each other; the resulting at least partial positive interference adapted to enhance the velocity and trajectory of at least one of these airflows; and in some embodiments serves as a "turbo boost" to aerosol entrainment and delivery.

In some embodiments of the aerosol delivery device, an at least one angle of incidence between at least two of the at least one airflow through the device housing produced by the user inhaling from the aerosol delivery device is modulated by user/digital input to control the at least one airflow.

In some embodiments of the aerosol delivery device, an at least one angle of incidence between at least two of the at least one airflow through the device housing produced by the user inhaling from the aerosol delivery device is modulated automatically by airflow, user inhalation rate, user inhalation force, airflow sensor relay feedback or a combination thereof.

In some embodiments of the aerosol delivery device, an at least one angle of incidence between at least two of the at least one airflow through the device housing produced by the user inhaling from the aerosol delivery device is modulated to limit/restrict airflow, airflow velocity, airflow volume, or a combination thereof.

In some embodiments of the aerosol delivery device, an at least one angle of incidence between at least two of the at least one airflow through the device housing produced by the user inhaling from the aerosol delivery device is modulated to control/change airflow, airflow velocity, airflow volume, or a combination thereof.

Most embodiments of the aerosol delivery device further comprising an at least one dial, switch, valve, lever, or a combination thereof to control the at least one airflow through the device and or aerosol chamber.

Some embodiments of the aerosol delivery device further comprise at least two aerosol generating settings to vary the amount and or properties of aerosol generated by the at least one aerosol generating element.

Some embodiments of the aerosol delivery device further comprise at least two aerosol generating settings to vary the amount and or properties of aerosol generated by the at least one aerosol generating element; the selection of the at least two aerosol generating settings determined automatically by airflow, user inhalation rate, user inhalation force, or a combination thereof.

Some embodiments of the aerosol delivery device further comprise at least two aerosol generating settings to vary the amount and or properties of aerosol generated by the at least one aerosol generating element; the selection of the at least two aerosol generating settings determined automatically by airflow, user inhalation rate, user inhalation force, type of said aerosolizable substance/formulation, or a combination thereof, by a relay/feedback from an at least one airflow sensor, pressure sensor, (substance ID) reader, or a combination thereof.

Some embodiments of the aerosol delivery device are further adapted to provide for a sustained maximal inhalation when a user or patient is able to sustain for a period of inhalation a negative pressure, airflow rate, or a combination thereof that is at least as great as the negative pressure threshold setting, airflow rate threshold setting, or a combination thereof selected by the user/digital input.

Some embodiments of the aerosol delivery device are further adapted to provide strength training of the muscles involved in respiration and help maintain lung elasticity.

Some embodiments of the aerosol delivery device are further adapted to provide incentive inhalation feedback to the user; the incentive inhalation feedback is selected from visual incentive signals, auditory incentive signals, vibrations, or a combination thereof.

Preferred embodiments of the aerosol delivery device are further adapted to only allow ambient/unaerosolized air to enter when the user is inhaling or inhaling sufficiently or inhaling above a threshold from the aerosol delivery device.

Preferred embodiments of the aerosol delivery device have aerosol generation that is activated/actuated and coordinated with the breathing cycle so that the aerosolizable substance or formulation is conserved until/between periods of user inhalation.

Some embodiments of the aerosol delivery device are further adapted to provide proper breathing technique training for optimized aerosol delivery.

Preferred embodiments of the aerosol delivery device are further adapted to limit/constrain airflow, airflow velocity, airflow volume, airflow rate, user inhalation rate, user generated negative pressure, or a combination thereof to a range conducive for aerosol delivery efficiency, accuracy and precision, and limiting or preventing deviation; limiting or preventing intra-user and or inter-user variability when using said aerosol delivery device.

Preferred embodiments of the aerosol delivery device are further adapted to selectively target aerosols to one or more different airway regions; one or more different airway regions comprising the upper airways, upper respiratory tract, nasal cavity, pharynx, larynx, lower airways, lower respiratory tract, trachea, bronchi, lungs, bronchioles, deep lung, alveoli where systemic exchange takes place, or a combination thereof.

Different embodiments of the aerosol delivery device are further adapted to receive electrical energy from an electrical wall socket/outlet, battery, rechargeable battery, or a combination thereof to power said at least one aerosol generating element.

Most embodiments with at least one rechargeable battery are further adapted to receive electrical energy to recharge the at least one associated battery, such as a lithium battery (a non-limiting example) that powers the at least one aerosol generating element. The electrical energy is received via an at least one power adapter, AC/DC power adapter, AC power connector, AC adapter inlet/socket, AC adapter outlet, AC power adapter, AC adapter power cord, AC power cord, DC power connectors, DC adapter inlet/socket, DC adapter outlet, DC power adapter, DC adapter power cord, DC power cord, male USB fitting, female USB fitting, USB adapter inlet/socket, USB adapter outlet, USB power adapter, USB power cord, USB cord, male micro-USB fitting, female micro-USB fitting, micro-USB adapter inlet/socket, micro-USB adapter outlet, micro-USB power adapter, micro-USB power cord, micro-USB cord, male mini-USB fitting, female mini-USB fitting, mini-USB adapter inlet/socket, mini-USB adapter outlet, mini-USB power adapter, mini-USB power cord, mini-USB cord, fuel cell, micro-turbine, wireless power transfer source, inductive coupling receiver, capacitive coupling receiver, charging pad/surface, or a combination or derivative thereof.

In preferred embodiments, the at least one ambient/unaerosolized air inlet, the at least one aerosolized air out, and the at least one airflow passage there between/therein are structurally associated with an at least one aerosol chamber of the aerosol delivery device. Some embodiments of the device can have at least two aerosol chambers.

The aerosol delivery device is not associated with nor having compressed/pressurized gas.

In some embodiments, the aerosol delivery device comprises at least two different aerosolizable substances or formulations (or dosages thereof) and is able to aerosolize these at least two different aerosolizable substances or formulations separately, sequentially, or simultaneously. The selection of aerosolization of one or both of these two different aerosolizable substances or formulations (or dosages thereof) can be selected by user/digital input, such as providing signal to an at least one aerosol generating element and or blister strip, packaging, vial, reservoir, or cartridge that contains or releases said at least one aerosolizable substance or formulation (or dosage thereof).

The disclosure is also an aerosol delivery device having a structure comprising a housing, an at least one air inlet, an at least one aerosolized air outlet, and an at least one airflow passage there between/therein. The aerosol delivery device further comprises an at least one aerosol generating element producing an aerosol from an at least one aerosolizable substance or formulation with the use of electrical energy to produce vaporizing heat, vibration, or a combination thereof, without the use of compressed/pressurized gas. The aerosol delivery device further has an at least one airflow through its housing produced by a user inhaling from the aerosol delivery device, preferably its mouthpiece, and entraining the aerosol when generated.

The aerosol delivery device further has an at least one rechargeable battery that at least powers the at least one aerosol generating element. The at least one rechargeable battery receives electrical energy via an at least one power adapter, AC/DC power adapter, AC power connector, AC adapter inlet/socket, AC adapter outlet, AC power adapter, AC adapter power cord, AC power cord, DC power connectors, DC adapter inlet/socket, DC adapter outlet, DC power adapter, DC adapter power cord, DC power cord, male USB fitting, female USB fitting, USB adapter inlet/socket, USB adapter outlet, USB power adapter, USB power cord, USB cord, male micro-USB fitting, female micro-USB fitting, micro-USB adapter inlet/socket, micro-USB adapter outlet, micro-USB power adapter, micro-USB power cord, micro-USB cord, male mini-USB fitting, female mini-USB fitting, mini-USB adapter inlet/socket, mini-USB adapter outlet, mini-USB power adapter, mini-USB power cord, mini-USB cord, fuel cell, micro-turbine, wireless power transfer source, inductive coupling receiver, capacitive coupling receiver, charging pad/surface, or a combination or derivative thereof.

The disclosure is also an aerosol delivery device having a structure comprising a housing, an at least one air inlet, an at least one aerosolized air outlet, preferably with user interface such as a mouthpiece, and an at least one airflow passage there between/therein. The aerosol delivery device further comprises an at least one aerosol generating element producing an aerosol from an at least one aerosolizable substance or formulation with the use of electrical energy and without the use of compressed/pressurized gas. The aerosol delivery device further has an at least one airflow through its housing produced by a user inhaling from the aerosol delivery device and entraining the aerosol when generated. The aerosol delivery device further has an adjustable airflow restriction of the at least one airflow as the at least one air inlet, the at least one aerosolized air outlet, the at least one airflow passage, or a combination thereof undergoes an at least one physical change selected from changes in size, angle, shape, biasing resistance to flow, number of apertures, shunting of airflow, or a combination thereof; said at least one physical change is modulated by user/digital input to control the adjustable airflow restriction and to regulate an at least one parameter selected from user inhalation resistance, user inhalation duration, user inhalation rate, aerosol delivery efficiency, targeting of aerosol to different user airway regions, or a combination thereof.

The disclosure is also an aerosol delivery device having a structure comprising a housing, an at least one air inlet, an at least one aerosolized air outlet with user interface, and an at least one airflow passage there between/therein. The aerosol delivery device further comprises an at least one aerosol generating element producing an aerosol from an at least one aerosolizable substance or formulation with the use of electrical energy and without the use of compressed/pressurized gas. The aerosol delivery device further has an at least one airflow through the housing produced by a user inhaling from the aerosol delivery device and entraining aerosol when generated. The aerosol delivery device further has an at least one negative pressure within the device housing produced by a user inhaling from the aerosol delivery device; wherein the at least one negative pressure is adjustable as said at least one air inlet, said at least one aerosolized air outlet, said at least one airflow passage, or a combination thereof undergoes an at least one physical change selected from changes in size, angle, shape, biasing resistance to flow, number of apertures, shunting of airflow, or a combination thereof; said at least one physical change is modulated by user/digital input to control the at least one negative pressure and to regulate an at least one parameter selected from user inhalation resistance, user inhalation duration, user inhalation rate, aerosol delivery efficiency, targeting of aerosol to different user airway regions, or a combination thereof.

For patients with adequate lung function that can achieve greater inhalation effort, the different airflow resistance settings and or different negative pressure settings of this novel aerosol delivery device can have profound effects on aerosol delivery dynamics. Aerosol generation and aerosol delivery occur when enough negative pressure builds within the device to cause actuation. After building up the necessary negative pressure required for valve actuation, aerosol is generated at the precise moment that the valve opens to allow a rapid stream of ambient air into the device for entraining and efficiently carrying out this aerosol as a bolus.

Choosing different settings can allow this bolus to be sustained as a stream over different lengths of inhalation time corresponding to different airflow resistance settings and or different negative pressures that can be sustained and selected by the user or patient. Moreover, by having actuation of aerosolization and aerosol entrainment associated with different airflow resistance settings and or different negative pressure settings, this novel aerosol delivery device can be used to selectively target aerosols to one or more different airway regions. In effect, aerosol actuation, entrainment, and delivery occur when one or more different airways are optimally expanded with the desired pressure for enhanced drug targeting and delivery efficiency. The aerosol delivery device is thus adapted to selectively target aerosols to one or more different airway regions by selecting different negative pressure threshold settings of actuation of aerosolization. The one or more different airway regions are chosen from the regions, including, but not limited to, the upper airways, upper respiratory tract, nasal cavity, pharynx, larynx, lower airways, lower respiratory tract, trachea, bronchi, lungs, bronchioles, deep lung, and alveoli where systemic exchange takes place.

More pharmaceuticals are being made available for inhalation. This includes pharmaceuticals that can be delivered to the systemic circulation via the pulmonary route, such as insulin. As an improved drug delivery device, embodiments of the present disclosure can improve the delivery dynamics and targeting of these drugs. Selective targeting of aerosols to one or more different airway regions can aid in the targeting of aerosolized chemotherapies against lung cancer, including targeting an airway region having a tumor. Selective targeting of aerosols to one or more different airway regions can also have profound lifesaving and medical military applications, including biodefense to counter bioterrorism, by coating upper airways with antibiotics against anthrax or other infectious agents, or by providing anticholinergic agents to the systemic circulation via alveoli as an antidote to nerve agent exposure. Embodiments of the present disclosure also have the potential to enhance the deliverability of drug candidates in development, which has the potential to reduce drug development costs. Therefore, embodiments of the present disclosure fulfill important unmet other needs, and has applications that transcend beyond medication delivery to asthma, COPD, and cystic fibrosis patients that have trouble breathing, and opens the way for treating countless other patients, including those with the ability to generate greater negative pressures.

Devices of the present disclosure are able to deliver aerosols of various substances that include, but are not limited to: unformulated active pharmaceutical ingredient, formulated active pharmaceutical ingredient, pharmaceutical inactive or excipient ingredient, non-biological materials, biological materials, plant material or extracts, animal material or extracts, cellular material or extracts, cultured cell line material or extracts, cells, stem cells, bacterial material or extracts, fungal material or extracts, viral material or extracts, peptides, polypeptides, recombinant proteins, glycoproteins, sugars, monosaccharides, disaccharides, and polysaccharides, lipids, fatty acids and prostaglandins, prostacyclins and prostacyclin analogues, cholesterol, lipoproteins, vesicles, liposomes, nutrients/supplements, holistic substances, antibodies/immunoglobulins and/or fragments thereof, immunosuppressants, immunotherapies, water, water soluble substances, antipsychotics, water insoluble substances, vitamins, coenzymes, enzymes, substrates, inhibitors, hormones, steroids, amino acids, neurotransmitters, cell signaling molecules, antibiotics, NSAIDs, cellular receptors and or receptor fragments, ion channels/ion channel fragments, ligands/ligand fragments, single stranded/double stranded nucleotides, deoxyribonucleic acids and/or ribonucleic acids, small interfering RNA, siRNA, transcription factors, transcription inhibitors, translation factors, translation inhibitors, vaccines, antihistamines, anti-inflammatory substances, cytotoxic substances, anti-toxins, anti-venoms, anticoagulants, vasodilators, bronchodilators, stimulants, anti-depressants, analgesics, anesthetics, therapeutic gases, including, but not limited to nitric oxide, nitrous oxide, hydrogen sulfide, carbon monoxide, carbon dioxide, nitrogen, cyclopropane, helium, and oxygen, diatomic molecules and gases, electrolytes, ionic substances, non-ionic substances, minerals, salts, hydrates, anhydrates, naturally occurring non-organic molecules or compounds, synthetic/modified non-organic molecules or compounds, naturally occurring organic molecules or compounds, synthetic/modified organic molecules or compounds, medical/diagnostic probes/tracers, fluorescent substances, magnetic substances, radioisotopes or radioactive substances, nanoparticles, from any phase of any of these aforementioned materials, solid phases, liquid phases, gaseous phases, polymers of any of these aforementioned materials, precursors of any of these aforementioned materials, derivatives of any of these aforementioned materials, enantiomers of any of these aforementioned materials, stereoisomers of any of these aforementioned materials, hybrid molecules of any of these aforementioned materials, combinations of any of these aforementioned materials, suspensions, mixtures/solutions of any of these aforementioned materials.

Examples of pharmaceutical aerosols that can be delivered by the embodiments of the present disclosure include, but are not limited to: acebutolol, acetaminophen, adrenaline (epinephrine), alprazolam, amantadine, amiloride, amitriptyline, amoxicillin, anticholinergic agent, apomorphine diacetate, apomorphine hydrochloride, atropine, azatadine, betahistine, brompheniramine, bumetanide, buprenorphine, bupropion hydrochloride, butalbital, butorphanol, carbinoxamine maleate, celecoxib, chlordiazepoxide, chlorpheniramine, chlorzoxazone, ciclesonide, ciclosporin, citalopram, clomipramine, clonazepam, clozapine, codeine, cyclobenzaprine, cyproheptadine, dapsone, dextran sulfate, diazepam, diclofenac ethyl ester, diflunisal, disopyramide, doxepin, estradiol, ephedrine, estazolam, ethacrynic acid, fenfluramine, fenoprofen, flecainide, flunitrazepam, galanthamine, granisetron, haloperidol, hydromorphone, hydroxychloroquine, hyoscyamine, ibuprofen, imipramine, indomethacin ethyl ester, indomethacin methyl ester, insulin, interleukin, isocarboxazid, ketamine, ketoprofen, ketoprofen ethyl ester, ketoprofen methyl ester, ketorolac ethyl ester, ketorolac methyl ester, ketotifen, lamotrigine, lidocaine, loperamide, loratadine, loxapine, maprotiline, memantine, meperidine, metaproterenol, methoxsalen, metoprolol, mexiletine HCl, midazolam, mirtazapine, morphine, nalbuphine, naloxone, naproxen, naratriptan, nicotine, norepinephrine, nortriptyline, olanzapine, orphenadrine, oxycodone, paroxetine, pergolide, phenytoin, pindolol, piribedil, pramipexole, procainamide, prochloperazine, propafenone, propranolol, pyrilamine, quetiapine, quinidine, racepinephrine, rizatriptan, ropinirole, sertraline, selegiline, sildenafil, spironolactone, tacrine, tadalafil, terbutaline, testosterone, thalidomide, theophylline, tocainide, toremifene, trazodone, triazolam, trifluoperazine, valproic acid, venlafaxine, vitamin E, zaleplon, zotepine, amoxapine, atenolol, benztropine, caffeine, doxylamine, estradiol 17-acetate, flurazepam, flurbiprofen, hydroxyzine, ibutilide, indomethacin norcholine ester, ketorolac norcholine ester, melatonin, metoclopramide, nabumetone, perphenazine, protriptyline HCl, quinine, triamterene, trimipramine, zonisamide, bergapten, chlorpromazine, colchicine, diltiazem, donepezil, eletriptan, estradiol-3,17-diacetate, efavirenz, esmolol, fentanyl, flunisolide, fluoxetine, hyoscyamine, indomethacin, isotretinoin, linezolid, meclizine, paracoxib, pioglitazone, rofecoxib, sumatriptan, tetrahydrocannabinol, tolterodine, tramadol, tranylcypromine, trimipramine maleate, valdecoxib, vardenafil, verapamil, zolmitriptan, zolpidem, zopiclone, bromazepam, buspirone, cinnarizine, dipyridamole, naltrexone, sotalol, telmisartan, temazepam, albuterol, apomorphine hydrochloride diacetate, carbinoxamine, clonidine, diphenhydramine, thambutol, fluticasone proprionate, fluconazole, lovastatin, lorazepam N,O-diacetyl, methadone, nefazodone, oxybutynin, promazine, promethazine, sibutramine, tamoxifen, tolfenamic acid, aripiprazole, astemizole, benazepril, clemastine, estradiol 17-heptanoate, fluphenazine, protriptyline, ethambutal, frovatriptan, pyrilamine maleate, scopolamine, tacrolimus, triamcinolene acetonide, epinephrine, and any analogues, derivatives, and combinations thereof.

Antibiotic active pharmaceutical ingredient examples for aerosolization with this device, include, but are not limited to: polyketide antibiotics; macrolide antibiotics, including, but not limited to, clarithromycin, erthythromycin, azithromycin, dirithromycin, roxithromycin, telithromycin, carbomycin A, josamycin, kitasamycin, midecamycin, oleandomycin, solithromycin, spiramycin, troleandomycin; beta-lactam antibiotics; penicillin drugs including, but not limited to amoxicillin, ampicillin, talampicillin, bacampicillin, lenampicillin, mezlocillin, sultamicillin, temocillin; cephem/cephalosporin antibiotics including, but not limited to, cefaclor, cefadroxil, cefalexin, cefpodoxime proxetil, cefixime, cefdinir, ceftibuten, cefotiam hexetyl, cefetamet pivoxil, cefuroxime axetil; penem antibiotics including, but not limited to, faropenem, ritipenem; monobactam antibiotics; sulfonamide antibiotics; lincosamide antibiotics including, but not limited to, lincomycin or clindamycin; aminoglycoside antibiotics including, but not limited to amikacin, tobramycin, paromomycin; tetracycline antibiotics including, but not limited to, tetracycline, minocycline, doxycycline; quinolone antibiotics including, but not limited to, ofloxacin, levofloxacin, norfloxacin, enoxacin, ciprofloxacin, lomefloxacin, tosufloxacin, fleroxacin, sparfloxacin, temafloxacin, nadifloxacin, grepafloxacin, baloflaxacin, prulifloxacin, pazufloxacin; nitroimidazole antibiotics including, but not limited to, metronidazole, tinidazole; nitrofuran antibiotics including, but not limited to, nitrofurantoin, furazolidone, nifurtoinol; rifamycin antibiotics including, but not limited to, rifampicin, rifabutin, rifapentine, rifaximin; glycopeptide antibiotics including, but not limited to vancomycin, ramoplanin; and any salts, solvates, polymorphs, racemic mixtures, enantiomers, derivatives, mixtures and combinations thereof.

Other embodiments of aerosol delivery devices within the scope of the present disclosure include motorized or electronic controlled adjustable negative pressure threshold valves of actuation, which employ the use of solenoid valves and pressure sensors and the necessary circuitry, buttons, and power elements to accomplish this. Even further conceivable aerosol delivery device embodiments can include a moveable seal that exists in a position that allows aerosol delivery to occur until moved out of position by actuation of the valve during inhalation, so that aerosolization does not occur during inhalation, but occurs during exhalation. These other conceivable embodiments are not shown and are not meant to be limiting.

There are methods for using the aerosol delivery device disclosed in the present disclosure, as well as, methods to produce the desired aerosolized therapies and aerosol delivery dynamics when using the present disclosure.

As to the manner of usage and operation of the present disclosure, the same should be apparent from the above description. Accordingly, no further discussion relating to the manner of usage and operation will be provided.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. An aerosol delivery device comprising:

an airflow inlet;

a mouthpiece region having an aerosol outlet, wherein the mouthpiece region is removably attached to the aerosol delivery device;

an airflow path from the airflow inlet to the aerosol outlet;

a receptacle configured to receive a cartridge, wherein the cartridge includes an aerosolizable substance and a vapor element, the aerosolizable substance at least partially surrounds the vapor element, and the vapor element includes an electrically-resistive heater configured to, when activated, vaporize a portion of the aerosolizable substance to produce an aerosol;

an internal battery to provide power;

a controller coupled to the internal battery to receive the power and configured to, in response to each inhalation, activate the vapor element to release a respective dose of the aerosol of the aerosolizable substance; and a connector, when connected, configured to receive power from an external source to recharge the internal battery, wherein the connector is positioned at an end of the aerosol delivery device opposite the aerosol outlet, wherein the airflow inlet is located between the mouthpiece region and the connector, the aerosol delivery device has an overall elongated shape of non-circular cross-section, the aerosol delivery device includes six faces, the aerosol outlet is located at a first face of the six faces, a second face is opposite the first face, and a third face, a fourth face, a fifth face, and a sixth face extend between the first face and the second face, the third face is opposite the fourth face and the fifth face is opposite the sixth face, and the controller and the internal battery are disposed in a first space between the third face and the fourth face and in a second space between the fifth face and the sixth face.

2. The aerosol delivery device of claim 1, wherein the controller is configured to transfer, send or receive data or instructions between an external electronic device, computer or smart phone.

3. The aerosol delivery device of claim 2, wherein the data or the instructions include information to authorize a user or use, information to lockout unauthorized users or use, a password, user data, medicament information, dosage counting, time/date memory, dosage usage history, serial number, instructions used by the controller to regulate heating temperatures, power, a duration of heating, period, of the vapor element, or any combination thereof.

4. The aerosol delivery device of claim 2, further comprising a microchip or memory chip configured to store at least some of the data or the instructions.

5. The aerosol delivery device of claim 1, wherein the connector includes a USB connector, a USB port, a micro USB connector, a micro USB port, an adaptor, or a derivative thereof.

6. The aerosol delivery device of claim 1, wherein the airflow path extends through the cartridge.

7. The aerosol delivery device of claim 1, further comprising a sensor configured to detect an inhalation and provide a signal to the controller, the signal indicating detection of the inhalation.

8. The aerosol delivery device of claim 1, wherein the controller is configured to illuminate an indicator light when in use.

9. The aerosol delivery device of claim 1, further comprising an electrical contact configured to provide electrical communication between the controller and the cartridge.

10. The aerosol delivery device of claim 1, wherein the aerosolizable substance includes at least one of a cannabinoid, tetrahydrocannabinol, a tetrahydrocannabinol salt, a tetrahydrocannabinol analogue, a tetrahydrocannabinol derivative, a tetrahydrocannabinol extract, or any combination thereof.

11. The aerosol delivery device of claim 1, wherein the aerosolizable substance includes at least one of nicotine, a nicotine salt, a nicotine analogue, a nicotine derivative, a nicotine extract, or any combination thereof.

12. The aerosol delivery device of claim 1, wherein the controller is configured to illuminate an indicator light to signal when data or instructions are being transferred.

13. The aerosol delivery device of claim 1, wherein the cartridge is configured to be replaceable.

14. The aerosol delivery device of claim 1, wherein the cartridge is configured to be refillable with the aerosolizable substance.

15. The aerosol delivery device of claim 1, further comprising a circuit board configured to include the controller.

16. The aerosol delivery device of claim 1, wherein the external source to recharge the internal battery includes an external device or a power adapter.

17. The aerosol delivery device of claim 1, further comprising a sensor configured to detect an inhalation duration, an inhalation intensity, or a combination thereof, wherein the controller is configured to receive detection of the inhalation duration, the inhalation intensity, or the combination thereof from the sensor.

18. The aerosol delivery device of claim 17, wherein the sensor includes at least one of an airflow sensor, a piezoelectric sensor, or a pressure sensor.

19. The aerosol delivery device of claim 18, further comprising an indicator light, wherein the controller is configured to cause the indicator light to illuminate in response to detection of the inhalation duration, the inhalation intensity, or the combination thereof.

20. The aerosol delivery device of claim 1, further comprising an indicator light, wherein the controller is configured to cause the indicator light to illuminate in response to detection of a level of electrical power of the internal battery, recharging of the internal battery, the internal battery falling below an available power threshold, or any combination thereof.

21. The aerosol delivery device of claim 1, further comprising an indicator light, wherein the controller is configured to cause the indicator light to illuminate in response to detection that a temperature of the vapor element is equal to or greater than a temperature setting.

22. The aerosol delivery device of claim 1, further comprising an indicator light, wherein the controller is further configured to cause the indicator light to illuminate in response to detection that vaporization is taking place.

23. The aerosol delivery device of claim 1, wherein the controller is configured to store a temperature setting associated with the vapor element, wherein the temperature setting indicates a temperature to heat the aerosolizable substance.

24. The aerosol delivery device of claim 1, wherein the first space is a same space as the second space.

25. The aerosol delivery device of claim 1, wherein the aerosolizable substance and the vapor element are additionally disposed in the first space between the third face and the fourth face and in the second space between the fifth face and the sixth face.

26. The aerosol delivery device of claim 1, wherein the third face and the fourth face have a larger surface area than the fifth face and the sixth face and the airflow inlet is at least partially defined by the third face.

27. An aerosol delivery device, comprising:

a mouthpiece having an airflow outlet;

an airflow path from an airflow inlet to the airflow outlet;

a cartridge including an aerosolizable substance and a vapor element, the aerosolizable substance at least partially surrounding the vapor element and the vapor element including an electrically-resistive heater configured to vaporize of a portion of the aerosolizable substance to provide a condensation aerosol;

a housing configured to receive the cartridge;

an internal power source configured to provide electrical power;

a controller coupled to the internal power source to receive the electrical power and configured to cause the vapor element of the cartridge to vaporize the portion of the aerosolizable substance and provide the condensation aerosol into the airflow path; and a connector configured to receive power from an external source to recharge the internal power source, wherein the airflow inlet is located between the mouthpiece and the connector, the aerosol delivery device has six faces, during inhalation of the aerosol delivery device, the airflow outlet is located at a first face of the six faces and a second face of the six faces is opposite the first face, a remaining four faces of the six faces extend between the first face and the second face, the remaining four faces of the six faces include a third face opposite a fourth face and a fifth face opposite a sixth face, and the controller and the internal power source are disposed in a first space between the third face and the fourth face and in a second space between the fifth face and the sixth face.

28. An aerosol delivery device, comprising:

a plurality of external surfaces including a front face, a rear face opposite the front face, a first side face between the front face and the rear face, a second side face opposite the first side face, a downstream end face, and an upstream end face opposite the downstream end face, the front face and the rear face having a larger surface area than the first side face and the second side face;

a mouthpiece having an airflow outlet;

an airflow path extending from an airflow inlet to the airflow outlet;

an internal power source configured to provide electrical power;

a cartridge including an aerosolizable substance and a vapor element, the aerosolizable substance at least partially surrounding the vapor element and the vapor element configured to receive the electrical power from the internal power source to heat the aerosolizable substance;

a housing configured to receive the cartridge;

a controller coupled to the internal power source to receive the electrical power and configured to cause the vapor element of the cartridge to vaporize a portion of the aerosolizable substance and provide an aerosol into the airflow path; and a connector configured to receive power from an external source to recharge the internal power source, wherein the airflow inlet is located between the mouthpiece and the connector, the airflow path extends through the cartridge and is at least partially defined by the front face and the airflow outlet, during inhalation of the aerosol delivery device, the airflow outlet is located at the downstream end face of the plurality of external surfaces, and the controller and the internal power source are disposed in a first space between the front face and the rear face and in a second space between the first side face and the second side face.

29. An aerosol generating device, comprising:

a plurality of external surfaces including a front face, a rear face opposite the front face, a first side face between the front face and the rear face, a second side face opposite the first side face, a downstream end face, and an upstream end face opposite the downstream end face, the front face and the rear face having a larger surface area than the first side face and the second side face;

a mouthpiece having an airflow outlet;

an interface configured to receive power from an external source to recharge an internal power source; and a cartridge including an aerosolizable substance and a vapor element, the aerosolizable substance at least partially surrounding the vapor element, the vapor element configured to receive power from the internal power source to heat the aerosolizable substance, and at least one external face of the cartridge configured to form a portion of at least one surface of the plurality of external surfaces, wherein an airflow path extends through the cartridge from an airflow inlet to the airflow outlet, and the internal power source is disposed in a first space between the front face and the rear face and in a second space between the first side face and the second side face.

* * * * *